(12) United States Patent
Mulligan et al.

(10) Patent No.: US 12,201,405 B2
(45) Date of Patent: Jan. 21, 2025

(54) ASSESSING EFFECTIVENESS OF CPR

(71) Applicants: Flashback Technologies, Inc., Boulder, CO (US); The Regents of the University of Colorado, a body corporate, Denver, CO (US)

(72) Inventors: Isobel Jane Mulligan, Niwot, CO (US); Gregory Zlatko Grudic, Niwot, CO (US); Steven L. Moulton, Littleton, CO (US)

(73) Assignees: Flashback Technologies, Inc., Boulder, CO (US); The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/885,891

(22) Filed: Oct. 16, 2015

(65) Prior Publication Data
US 2016/0038043 A1      Feb. 11, 2016

Related U.S. Application Data

(63) Continuation-in-part of application No. 14/542,426, filed on Nov. 14, 2014, now Pat. No. 11,478,190, and
(Continued)

(51) Int. Cl.
*A61B 5/02* (2006.01)
*A61B 5/00* (2006.01)
(Continued)

(52) U.S. Cl.
CPC ...... *A61B 5/02042* (2013.01); *A61B 5/02028* (2013.01); *A61B 5/0205* (2013.01);
(Continued)

(58) Field of Classification Search
CPC ............ A61B 2562/0219; A61B 5/002; A61B 5/02028; A61B 5/02042; A61B 5/0205
See application file for complete search history.

(56) References Cited

U.S. PATENT DOCUMENTS

| 4,930,517 A | 6/1990 | Cohen et al. |
| 5,074,310 A | 12/1991 | Mick |

(Continued)

FOREIGN PATENT DOCUMENTS

| CA | 2871608 | 2/2021 |
| EP | 3468457 | 4/2019 |

(Continued)

OTHER PUBLICATIONS

U.S. Appl. No. 14/542,426, Final Office Action dated Sep. 26, 2016, 25 pages.
(Continued)

*Primary Examiner* — Tse W Chen
*Assistant Examiner* — Michael A Catina
(74) *Attorney, Agent, or Firm* — Nicholas Pfeifer; Smith & Hopen, P. A.

(57) ABSTRACT

Novel tools and techniques are provided for assessing, predicting and/or effectiveness of cardiopulmonary resuscitation ("CPR"), in some cases, noninvasively. In various embodiments, tools and techniques are provided for implementing rapid estimation of a patient's compensatory reserve index ("CRI") before, during, and after CPR is performed, and using the CRI and variations in CRI values to determine, in some instances, in real-time, the effectiveness of CPR that is performed.

35 Claims, 19 Drawing Sheets

Related U.S. Application Data a continuation-in-part of application No. 14/542,423, filed on Nov. 14, 2014, now Pat. No. 11,395,594, and a continuation-in-part of application No. 14/535,171, filed on Nov. 6, 2014, now Pat. No. 11,382,571, and a continuation-in-part of application No. 13/554,483, filed on Jul. 20, 2012, now Pat. No. 9,757,041, which is a continuation-in-part of application No. 13/041,006, filed on Mar. 4, 2011, now abandoned, which is a continuation-in-part of application No. 13/028,140, filed on Feb. 15, 2011, now Pat. No. 8,512,260, which is a continuation-in-part of application No. PCT/US2009/062119, filed on Oct. 26, 2009.

(60) Provisional application No. 62/064,809, filed on Oct. 16, 2014, provisional application No. 62/064,816, filed on Oct. 16, 2014, provisional application No. 61/905,727, filed on Nov. 18, 2013, provisional application No. 61/904,436, filed on Nov. 14, 2013, provisional application No. 61/900,980, filed on Nov. 6, 2013, provisional application No. 61/614,426, filed on Mar. 22, 2012, provisional application No. 61/510,792, filed on Jul. 22, 2011, provisional application No. 61/310,583, filed on Mar. 4, 2010, provisional application No. 61/305,110, filed on Feb. 16, 2010, provisional application No. 61/252,978, filed on Oct. 19, 2009, provisional application No. 61/166,499, filed on Apr. 3, 2009, provisional application No. 61/166,472, filed on Apr. 3, 2009, provisional application No. 61/166,486, filed on Apr. 3, 2009, provisional application No. 61/109,490, filed on Oct. 29, 2008.

(51) Int. Cl.
| | | |
|---|---|---|
| *A61B 5/0205* | (2006.01) | |
| *A61B 5/021* | (2006.01) | |
| *A61H 31/00* | (2006.01) | |
| *G16H 50/20* | (2018.01) | |
| *G16H 50/50* | (2018.01) | |
| *A61B 5/022* | (2006.01) | |
| *A61B 5/029* | (2006.01) | |
| *A61B 5/03* | (2006.01) | |
| *A61B 5/1455* | (2006.01) | |
| *A61B 5/318* | (2021.01) | |
| *A61B 5/369* | (2021.01) | |
| *A61B 5/398* | (2021.01) | |
| *A61B 7/04* | (2006.01) | |
| *A61M 1/16* | (2006.01) | |
| *G16H 40/20* | (2018.01) | |
| *G16H 40/63* | (2018.01) | |

(52) U.S. Cl.
CPC ........ *A61B 5/02108* (2013.01); *A61B 5/4848* (2013.01); *A61B 5/4875* (2013.01); *A61B 5/7275* (2013.01); *A61H 31/00* (2013.01); *G16H 50/20* (2018.01); *G16H 50/50* (2018.01); *A61B 5/002* (2013.01); *A61B 5/02241* (2013.01); *A61B 5/029* (2013.01); *A61B 5/031* (2013.01); *A61B 5/14551* (2013.01); *A61B 5/318* (2021.01); *A61B 5/369* (2021.01); *A61B 5/398* (2021.01); *A61B 5/4836* (2013.01); *A61B 5/6826* (2013.01); *A61B 5/7246* (2013.01); *A61B 5/7267* (2013.01); *A61B 5/742* (2013.01); *A61B 7/04* (2013.01); *A61B 2562/0219* (2013.01); *A61M 1/1613* (2014.02); *G16H 40/20* (2018.01); *G16H 40/63* (2018.01)

(56) References Cited

U.S. PATENT DOCUMENTS

| | | | |
|---|---|---|---|
| 5,619,990 | A * | 4/1997 | Kanai .................. G06F 19/3431 600/300 |
| 5,853,364 | A | 12/1998 | Baker, Jr. et al. |
| 5,865,168 | A | 2/1999 | Isaza |
| 5,967,981 | A | 10/1999 | Watrous |
| 5,984,893 | A | 11/1999 | Ward |
| 6,083,172 | A | 7/2000 | Baker, Jr. et al. |
| 6,094,592 | A | 7/2000 | Yorkey et al. |
| 6,206,830 | B1 | 3/2001 | Diab et al. |
| 6,248,080 | B1 | 6/2001 | Miesel |
| 6,338,713 | B1 | 1/2002 | Chamoun et al. |
| 6,371,921 | B1 | 4/2002 | Caro et al. |
| 6,398,728 | B1 | 6/2002 | Bardy |
| 6,409,675 | B1 | 6/2002 | Turcott |
| 6,411,833 | B1 | 6/2002 | Baker, Jr. et al. |
| 6,553,991 | B1 | 4/2003 | Isaza |
| 6,556,852 | B1 | 4/2003 | Schulze |
| 6,557,553 | B1 | 5/2003 | Borrello |
| 6,558,336 | B2 | 5/2003 | Collins |
| 6,589,189 | B2 | 7/2003 | Meyerson et al. |
| 6,591,122 | B2 | 7/2003 | Schmitt |
| 6,606,509 | B2 | 8/2003 | Schmitt |
| 6,675,031 | B1 | 1/2004 | Porges et al. |
| 6,721,584 | B2 | 4/2004 | Baker, Jr. et al. |
| 6,739,337 | B2 | 5/2004 | Isaza |
| 6,852,083 | B2 | 2/2005 | Caro et al. |
| 7,160,250 | B2 | 1/2007 | Lemaire |
| 7,231,245 | B2 | 6/2007 | Greenwald et al. |
| 7,285,100 | B2 | 10/2007 | Lemaire |
| 7,455,643 | B1 | 11/2008 | Li et al. |
| 7,547,283 | B2 | 6/2009 | Mourad et al. |
| 7,496,393 | B2 | 11/2009 | Diab et al. |
| 7,647,185 | B2 | 1/2010 | Tarassenko et al. |
| 7,654,964 | B1 | 2/2010 | Kroll et al. |
| 7,668,579 | B2 | 2/2010 | Lynn |
| 7,678,507 | B2 | 3/2010 | Berkow et al. |
| 7,720,516 | B2 | 5/2010 | Chin et al. |
| 7,865,224 | B2 | 1/2011 | Baker, Jr. et al. |
| 7,873,497 | B2 | 1/2011 | Weber et al. |
| 7,887,502 | B2 | 2/2011 | Ross et al. |
| 7,931,559 | B2 | 4/2011 | Baker, Jr. et al. |
| 7,957,780 | B2 | 6/2011 | Lamego et al. |
| 7,976,472 | B2 | 7/2011 | Kiani |
| 8,019,400 | B2 | 9/2011 | Diab et al. |
| 8,463,346 | B2 | 6/2013 | Kuhn et al. |
| 8,512,260 | B2 | 8/2013 | Grudic et al. |
| 8,641,635 | B2 | 2/2014 | Melker et al. |
| 9,603,534 | B2 | 3/2017 | Gabbay et al. |
| 9,757,041 | B2 | 12/2017 | Grudic et al. |
| 10,226,194 | B2 | 3/2019 | Grudic et al. |
| 2001/0027335 | A1 | 10/2001 | Meyerson et al. |
| 2003/0060690 | A1 | 3/2003 | Jelliffe et al. |
| 2003/0125612 | A1 | 7/2003 | Fox et al. |
| 2003/0130570 | A1 | 7/2003 | Krivitski et al. |
| 2003/0176931 | A1 | 9/2003 | Pednault et al. |
| 2003/0200189 | A1 | 10/2003 | Meng et al. |
| 2003/0212678 | A1 | 11/2003 | Bloom et al. |
| 2004/0215244 | A1* | 10/2004 | Marcovecchio .......... A61N 1/39 607/5 |
| 2004/0242972 | A1 | 12/2004 | Adak et al. |
| 2004/0267145 | A1 | 12/2004 | David et al. |
| 2005/0015009 | A1 | 1/2005 | Mourad et al. |
| 2005/0209516 | A1 | 9/2005 | Fraden |
| 2005/0228298 | A1 | 10/2005 | Banet et al. |
| 2006/0058691 | A1 | 3/2006 | Kiani |
| 2006/0106743 | A1 | 5/2006 | Horvitz |
| 2006/0161403 | A1 | 7/2006 | Jiang et al. |
| 2006/0166176 | A1 | 7/2006 | Lakin et al. |
| 2006/0178585 | A1 | 8/2006 | Sharrock |
| 2006/0195041 | A1 | 8/2006 | Lynn et al. |
| 2006/0253016 | A1 | 11/2006 | Baker, Jr. et al. |
| 2007/0015972 | A1 | 1/2007 | Wang et al. |
| 2007/0032732 | A1 | 2/2007 | Shelley et al. |
| 2007/0099239 | A1 | 5/2007 | Tabibiazar et al. |
| 2007/0112275 | A1 | 5/2007 | Cooke et al. |

(56) References Cited

U.S. PATENT DOCUMENTS

| | | |
|---|---|---|
| 2007/0213619 A1 | 9/2007 | Linder |
| 2008/0039731 A1 | 2/2008 | McCombie et al. |
| 2008/0045845 A1 | 2/2008 | Pfeiffer et al. |
| 2008/0067132 A1 | 3/2008 | Ross et al. |
| 2008/0077023 A1 | 3/2008 | Campbell et al. |
| 2008/0097173 A1 | 4/2008 | Soyemi et al. |
| 2008/0133434 A1 | 6/2008 | Asar et al. |
| 2008/0146890 A1 | 6/2008 | LeBoeuf et al. |
| 2008/0146892 A1 | 6/2008 | LeBoeuf et al. |
| 2008/0154814 A1 | 6/2008 | Chaudhury et al. |
| 2008/0234607 A1 | 9/2008 | Hunter-Jones et al. |
| 2008/0294217 A1 | 11/2008 | Lian et al. |
| 2009/0005703 A1 | 1/2009 | Fasciano |
| 2009/0036754 A1 | 2/2009 | Pons et al. |
| 2009/0069647 A1 | 3/2009 | McNames et al. |
| 2009/0112106 A1 | 3/2009 | Zhang |
| 2009/0143656 A1 | 6/2009 | Manwaring et al. |
| 2009/0149724 A1 | 6/2009 | Mark et al. |
| 2009/0149751 A1 | 6/2009 | Mourad et al. |
| 2009/0204162 A1 | 8/2009 | Addison et al. |
| 2009/0264776 A1 | 10/2009 | Vardy |
| 2009/0272678 A1 | 11/2009 | Sornmo et al. |
| 2009/0281434 A1* | 11/2009 | Messerges ............... A61B 5/02 600/485 |
| 2009/0287105 A1 | 11/2009 | Hirsch |
| 2009/0292198 A1 | 11/2009 | Kleiven et al. |
| 2009/0043222 A1 | 12/2009 | Chetham |
| 2010/0016739 A1 | 1/2010 | Shelley et al. |
| 2010/0041962 A1 | 2/2010 | Causevic et al. |
| 2010/0081942 A1* | 4/2010 | Huiku .................. A61B 5/7275 600/483 |
| 2010/0094158 A1 | 4/2010 | Solem et al. |
| 2010/0160795 A1 | 6/2010 | Banet et al. |
| 2010/0191128 A1 | 7/2010 | Shelley et al. |
| 2010/0204589 A1 | 8/2010 | Swoboda et al. |
| 2010/0249559 A1 | 9/2010 | Lovejoy |
| 2011/0077532 A1 | 3/2011 | Kim et al. |
| 2011/0112799 A1 | 5/2011 | Weber et al. |
| 2011/0152651 A1 | 6/2011 | Berkow |
| 2011/0160549 A1 | 6/2011 | Saroka et al. |
| 2011/0172545 A1 | 7/2011 | Grudic et al. |
| 2011/0201962 A1 | 8/2011 | Grudic et al. |
| 2011/0282169 A1 | 8/2011 | Grudic et al. |
| 2011/0237914 A1 | 9/2011 | Lamego et al. |
| 2012/0123232 A1 | 5/2012 | Najarian et al. |
| 2012/0136224 A1 | 5/2012 | Najarian et al. |
| 2012/0184840 A1 | 7/2012 | Najarian et al. |
| 2012/0245439 A1 | 9/2012 | André et al. |
| 2012/0269420 A1 | 10/2012 | Najarian et al. |
| 2012/0296219 A1* | 11/2012 | Chon ................. A61B 5/02042 600/479 |
| 2012/0330117 A1 | 12/2012 | Grudic et al. |
| 2013/0041268 A1 | 2/2013 | Rimoldi et al. |
| 2013/0218056 A1 | 8/2013 | Aelen et al. |
| 2013/0245397 A1 | 9/2013 | Grudic et al. |
| 2013/0261468 A1 | 10/2013 | Semler et al. |
| 2013/0343585 A1 | 12/2013 | Bennett et al. |
| 2014/0073938 A1 | 3/2014 | Rodriguez-Llorente et al. |
| 2014/0107437 A1 | 4/2014 | Pinsky |
| 2014/0236053 A1 | 8/2014 | Walker et al. |
| 2015/0065826 A1 | 3/2015 | Mulligan et al. |
| 2015/0073723 A1 | 3/2015 | Mulligan et al. |
| 2015/0141769 A1 | 5/2015 | Mulligan et al. |
| 2016/0015284 A1 | 1/2016 | Grudic et al. |
| 2016/0038042 A1 | 2/2016 | Mulligan et al. |
| 2016/0162786 A1 | 6/2016 | Grudic et al. |
| 2016/0354039 A1 | 12/2016 | Soto et al. |
| 2016/0374625 A1 | 12/2016 | Mulligan et al. |
| 2017/0007139 A9 | 1/2017 | Grudic et al. |
| 2017/0215016 A1 | 7/2017 | Dohmen et al. |
| 2017/0258329 A1 | 9/2017 | Marsh |
| 2017/0303799 A1 | 10/2017 | Grudic et al. |
| 2017/0347177 A1 | 11/2017 | Masaki |
| 2018/0214028 A1 | 8/2018 | Zhang et al. |
| 2020/0205734 A1 | 7/2020 | Mulligan et al. |
| 2020/0205747 A1 | 7/2020 | Mulligan et al. |

FOREIGN PATENT DOCUMENTS

| | | |
|---|---|---|
| WO | WO 2003-077854 A2 | 9/2003 |
| WO | WO 2003-091421 A3 | 11/2003 |
| WO | WO-2005-055825 A1 | 6/2005 |
| WO | WO-2005-112756 A1 | 12/2005 |
| WO | WO-2007-011565 A1 | 1/2007 |
| WO | WO 2007-098957 A1 | 9/2007 |
| WO | WO 2007-117570 A2 | 10/2007 |
| WO | WO 2007-149533 A2 | 12/2007 |
| WO | WO 2010-009735 A2 | 1/2010 |
| WO | WO 2010-053743 A1 | 5/2010 |
| WO | WO 2010-117572 A2 | 10/2010 |
| WO | WO-2011-002904 A2 | 1/2011 |
| WO | WO 2011-050066 A2 | 4/2011 |
| WO | WO 2011-103102 A1 | 8/2011 |
| WO | WO 2011-109734 A1 | 9/2011 |
| WO | WO 2012-054880 A2 | 4/2012 |
| WO | WO 2012-166568 A3 | 12/2012 |
| WO | WO 2013-016212 A1 | 1/2013 |
| WO | WO 2014-149981 A1 | 9/2014 |
| WO | WO-2015-042484 A1 | 3/2015 |
| WO | WO 2015-069940 A1 | 5/2015 |
| WO | WO 2015-073909 A1 | 5/2015 |
| WO | WO 2015-073910 A1 | 5/2015 |
| WO | WO-2016-061542 A1 | 4/2016 |
| WO | WO-2016-061545 A1 | 4/2016 |
| WO | WO-2017-044868 A1 | 3/2017 |
| WO | WO-2017-218431 A1 | 12/2017 |

OTHER PUBLICATIONS

Intravenous Therapy (Wikipedia) Accessed on: Sep. 27, 2016, 12 pages.

U.S. Appl. No. 13/554,483, Final Office Action dated Oct. 7, 2016, 28 pages.

International Search Report and Written Opinion prepared by the U.S. Patent and Trademark Office as International Searching Authority for PCT International Patent Application No. PCT/US09/62119, mailed Feb. 3, 2010, 5 pages.

International Preliminary Report on Patentability prepared by the International Bureau for PCT/US2009/062119, mailed May 12, 2011, 6 pages.

Decision to Grant, Apr. 23, 2015 for EP 09825222.4, 3 pages.

European Search Report, Jun. 15, 2012 for EP 09825222.4, 10 pages.

Procopio et al (2008) Intelligent Robots And Systems IEEE/RSJ International Conference, pp. 620-627, "Learning in 1-14 dynamic environments with Ensemble Selection for autonomous outdoor robot navigation".

Shoemaker, et al (2001) CHEST, 120(2):528-538, "Outcome Prediction of Emergency Patients by Noninvasive Hemodynamic Monitoring".

Supplemental European Search Report, Jul. 3, 2012 for EP 09825222.4, 1 page.

U.S. Appl. No. 13/126,727, NonFinal Office Action dated Sep. 11, 2014; 58 pages.

U.S. Appl. No. 13/028,140, NonFinal Office Action dated Nov. 13, 2012; 27 pages.

U.S. Appl. No. 13/028,140, Notice of Allowance dated Feb. 22, 2013; 22 pages.

U.S. Appl. No. 13/889,513, NonFinal Office Action mailed Jun. 15, 2015, 27 pages.

International Preliminary Report on Patentability prepared by the International Bureau for PCT/US11/24938, mailed Aug. 30, 2012, 7 pages.

International Search Report and Written Opinion prepared by the U.S. Patent and Trademark Office as International Searching Authority for PCT International Patent Application No. PCT/US2011/24938, mailed Jun. 7, 2011, 13 pages.

(56) References Cited

OTHER PUBLICATIONS

Supplemental European Search Report, Jun. 21, 2013 for EP 11745124.5, 7 pages.
U.S. Appl. No. 13/041,006, NonFinal Office Action dated May 23, 2014; 27 pages.
U.S. Appl. No. 13/041,006, NonFinal Office Action dated Dec. 22, 2014; 14 pages.
International Preliminary Report on Patentability prepared by the International Bureau for PCT/US11/27237, mailed Sep. 13, 2012, 10 pages.
International Search Report and Written Opinion prepared by the U.S. Patent and Trademark Office as International Searching Authority for PCT International Patent Application No. PCT/US2011/027237, mailed May 27, 2011, 16 pages.
Cooke et al. (2004) Journal of Applied Physiology 96(4):1249-1261, "Lower body negative pressure as a model to study progression to acute hemorrhagic shock in humans".
Extended European Search Report, Oct. 18, 2013 for EP11751440.6, 7 pages.
Lambert et al. (2007) ACTA Anesthesiologica Scandinavica 51(4):415-425, "Does a positive 1-27 end-expiratory pressure-induced reduction in stroke volume indicate preload responsiveness? An experimental study".
Ryan et al. (2008) Journal f Applied Physiology 104(5):1402-1409, "Breathing through an inspiratory threshold device improves stroke volume during central hypovolemia in humans".
Supplemental Extended European Search Report, Nov. 6, 2013 for EP11751440.6, 8 pages.
International Preliminary Report on Patentability prepared by the International Bureau for PCT International Patent Application No. PCT/US12/047659, mailed Feb. 6, 2014, 10 pages.
International Search Report and Written Opinion prepared by the U.S. International Searching Authority for PCT International Patent Application No. PCT/US12/047659, mailed Oct. 12, 2012, 16 pages.
Extended European Search Report for EP 12816832.5, mailed Oct. 6, 2014, 9 pages.
International Search Report and Written Opinion prepared by the Korean Intellectual Property Office as International Searching Authority for PCT International Patent Application No. PCT/US2014/064413, mailed Feb. 12, 2015, 13 pages.
International Search Report and Written Opinion prepared by the Korean Intellectual Property Office as International Searching Authority for PCT International Patent Application No. PCT/US2014/065818, mailed Feb. 26, 2015, 14 pages.
International Search Report and Written Opinion prepared by the Korean Intellectual Property Office as International Searching Authority for PCT International Patent Application No. PCT/US2014/065820, mailed Feb. 26, 2015, 14 pages.
Berkow (Aug. 2010) Intelomed, Inc., "CVInsight," 14 pages.
Berkow (Jan. 2012) 510(K) Summary, "CVInsight," 9 pages.
Najarian (2012) VCU School of Engineering ResearchReport, vol. 5, p. 3.
U.S. Appl. No. 13/126,727, Final Rejection dated Aug. 27, 2015; 33 pages.
U.S. Appl. No. 13/041,006, Final Rejection dated Sep. 15, 2015; 19 pages.
Canadian Patent Application No. 2,775,675, NonFinalOA dated Dec. 9, 2015; 3 pages.
International Search Report and Written Opinion prepared by the Korean Intellectual Property Office as International Searching Authority for PCT International Patent Application No. PCT/US2015/056078, mailed Jan. 25, 2016, 11 pages.
International Search Report and Written Opinion prepared by the Korean Intellectual Property Office as International Searching Authority for PCT International Patent Application No. PCT/US2015/56074, mailed Jan. 29, 2016, 13 pages.

Convertino, Victor, "Estimation of individual-specific progression to impending cardiovascular instability using arterial waveforms," Journal of Applied Physiology, Oct. 15, 2013, vol. 115, No. 8, pp. 1196-1202.
U.S. Appl. No. 14/542,426, Non-Final Office Action dated Feb. 26, 2016; 25 pages.
U.S. Appl. No. 13/554,483, Non-Final Office Action dated Mar. 22, 2016; 41 pages.
EP11751440.6, Office Action 94(3) dated Feb. 24, 2016, 5 pages.
U.S. Appl. No. 13/041,006, Non-final Office Action dated Apr. 22, 2016, 15 pages.
International Preliminary Report on Patentability prepared by the International Bureau for PCT International Patent Application No. PCT/US14/064413, mailed May 19, 2016, 10 pages.
International Preliminary Report on Patentability prepared by the International Bureau for PCT International Patent Application No. PCT/US14/65818, mailed May 26, 2016, 11 pages.
International Preliminary Report on Patentability prepared by the International Bureau for PCT International Patent Application No. PCT/US14/65820, mailed May 26, 2016, 11 pages.
International Preliminary Report on Patentability prepared by the International Bureau for PCT/US15/56074, mailed Apr. 27, 2017, 10 pages.
International Preliminary Report on Patentability prepared by the International Bureau for PCT/US15/56078, mailed Apr. 27, 2017, 7 pages.
Extended European Search Report for EP14862697.1, dated Jun. 14, 2017; 8 pages.
U.S. Appl. No. 14/885,888, Final Office Action dated Jul. 27, 2017, 29 pages.
EP 11745124.5, Office Action 94(3) dated Jul. 31, 2017, 6 pages.
Kotsiantis (2007) Department of Computer Science and Technology, "Supervised Matchine Learning: A Review of Classification Techniques," 20 pages.
Wu et al, (2009) World Congress on Computer Science and Information Enginerring, "Time Series Mining Approach for Noninvasive Intracranial Pressure Assessment: an Investigation of Different Regularization Techniques," 5 pages.
Extended European Search Report, Jun. 7, 2017 for EP14862921.5, 8 pages.
Extended European Search Report, Jun. 20, 2017 for EP14859538.2, 8 pages.
International Search Report and Written Opinion prepared by the Korean Intellectual Property Office as International Searching Authority for PCT International Patent Application No. PCT/US2017/037067, mailed Aug. 18, 2017, 21 pages.
International Search Report and Written Opinion prepared by the Korean Intellectual Property Office as International Searching Authority for PCT International Patent Application No. PCT/US2016/051130, mailed Dec. 8, 2016, 14 pages.
U.S. Appl. No. 14/535,171, NonFinalOA dated Dec. 16, 2016, 37 pages.
U.S. Appl. No. 14/885,888, NonFinalOA dated Dec. 16, 2016, 35 pages.
Nadler et al. 2014, Shock 42(2): 93-98, "The Value of Noninvasive Measurement of the Compensatory Reserve Index in Monitoring and Triage of Patients Experiencing Minimal Blood Loss".
Nadler et al. 2017, Annals of Medicine and Surgery, "The approximated cardiovascular reserve index complies with haemorrhage related hemodynamic deterioration pattern: A swine exsanguination model" 7 pages.
Canadian Patent Application No. 2,775,675, NonFinalOA dated Nov. 9, 2016; 4 pages.
U.S. Appl. No. 13/041,006, NonFinalOA dated Mar. 7, 2017, 21 pages.
U.S. Appl. No. 13/554,483, Notice of Allowance dated Mar. 7, 2017, 39 pages.
U.S. Appl. No. 13/889,513, Final Rejection dated Apr. 11, 2017; 51 pages.
Schmidt et al. (1997) Stroke, "Noninvasive Prediction of Intracranial Pressure Curves Using Transcranial Doppler Ultrasonography and Blood Pressure Curves," 22 pages.

(56) References Cited

OTHER PUBLICATIONS

U.S. Appl. No. 14/542,426, Non-Final Office Action dated May 5, 2017; 17 pages.
U.S. Appl. No. 14/542,423, NonFinal Office Action dated May 8, 2017; 35 pages.
U.S. Appl. No. 14/535,171, Final Office Action dated Nov. 16, 2017, 30 pages.
U.S. Appl. No. 13/889,513, NonFinal Office Action dated Dec. 1, 2017, 51 pages.
U.S. Appl. No. 14/867,938, NonFinal Office Action dated Dec. 8, 2017, 27 pages.
U.S. Appl. No. 13/041,006, NonFinal Office Action dated Dec. 15, 2017, 21 pages.
Canadian Patent Application No. 2,775,675, NonFinalOA dated Sep. 27, 2017; 4 pages.
U.S. Appl. No. 14/542,426, Non-Final Office Action dated Feb. 1, 2018, 19 pages.
U.S. Appl. No. 14/542,423, NonFinal Office Action dated Feb. 5, 2018, 24 pages.
Canadian Patent Application No. 2,871,608, NonFinalOA dated Jan. 25, 2018; 5 pages.
U.S. Appl. No. 14/885,888, NonFinal Office Action dated Mar. 15, 2018, 11 pages.
International Preliminary Report on Patentability prepared by the International Bureau for PCT/US2009/062119, mailed Mar. 22, 2018, 9 pages.
U.S. Appl. No. 15/649,411, NonFinalOA dated Apr. 5, 2018, 23 pages.
Extended European Search Report for EP15850241.9, dated Apr. 5, 2018; 8 pages.
U.S. Appl. No. 15/007,489, NonFinal Office Action dated Jun. 13, 2018; 48 pages.
U.S. Patent Application No. 14/535,1711, NonFinalOA dated Aug. 9, 2018, 23 pages.
U.S. Appl. No. 14/867,938, Notice of Allowance dated Sep. 6, 2018; 17 pages.
U.S. Appl. No. 13/889,513, Final Office Action dated Sep. 20, 2018, 25 pages.
U.S. Appl. No. 14/542,426, Final Office Action dated Sep. 27, 2018, 11 pages.
U.S. Appl. No. 14/885,888, Final Office Action dated Sep. 28, 2018, 7 pages.
U.S. Appl. No. 13/041,006, Final Office Action dated Oct. 3, 2018, 9 pages U.S. Appl. No. 15/261,661, NonFinal Office Action dated Oct. 12, 2018, 38 pages.
Canadian Patent Application No. 2,871,608, NonFinalOA dated Nov. 22, 2018, 3 pages.
European Patent Application No. 12816832.5, NonFinalOA dated Oct. 12, 2018, 4 pages.
International Preliminary Report on Patentability prepared by the International Bureau for PCT International Patent Application No. PCT/US2017/037067, mailed Dec. 27, 2018, 13 pages.
U.S. Appl. No. 14/542,423, NonFinal Office Action dated Dec. 28, 2018, 18 pages.
Extended European Search Report for EP16845202.7, dated Feb. 1, 2019; 6 pages.
Moulton et al. (2013) Trauma Acute Care Surg 75(6):1053-1059, "Running on empty? The Compensatory Reserve Index".
Poh et al. (2014) Experimental Physiology, 1421-1426, "Respiratory Pump Contributes to Increased Physiological Reserve for Compensation During Simulated Haemorrhage".
EPO Communication pursuant to Rules 161(2) and 162 EPC dated Feb. 1, 2019, 4 pages.
Extended European Search Report Written Opinion for EP16845202.7, dated Mar. 11, 2019, 8 pages.
EPO Communication pursuant to Rule 70(2) and 70(a)(2) EPC, dated Mar. 13, 2019, 1 page.
U.S. Appl. No. 15/007,489, Final Office Action dated Mar. 20, 2019, 36 pages.
U.S. Appl. No. 15/649,411, Non-Final OA dated Apr. 2, 2019, 24 pages.
U.S. Appl. No. 13/041,006, Non-Final OA dated Apr. 4, 2019, 15 pages.
U.S. Appl. No. 14/542,426, Non-Final OA dated Apr. 5, 2019, 9 pages.
U.S. Appl. No. 15/261,661, Final OA dated Apr. 5, 2019, 19 pages.
U.S. Appl. No. 13/889,513, Restriction Requirement dated Apr. 12, 2019, 9 pages.
U.S. Appl. No. 14/885,888, Non-Final Office Action dated May 15, 2019, 21 pages.
U.S. Appl. No. 14/535,171, Final OA dated Jul. 3, 2019, 20 pages.
U.S. Appl. No. 14/542,423, Non-Final Office Action dated Jul. 9, 2019, 17 pages.
U.S. Appl. No. 15/620,701, Non-Final Office Action dated Aug. 12, 2019, 27 pages.
Japan Patent Application No. 2017-539521 Office Action, dated Sep. 5, 2019, 7 pages.
EP Application No. 15850241.9, EP Examination Report, dated Oct. 14, 2019, 6 pages.
U.S. Appl. No. 16/726,334, filed Dec. 24, 2019 by Mulligan et al. and entitled "Device-Based Maneuver and Activity State-Based Physiologic Status Monitoring," 89 pages.
U.S. Appl. No. 16/726,337, filed Dec. 24, 2019 by Mulligan et al. and entitled "Ear-Based Physiological State Monitoring" 78 pages.
U.S. Appl. No. 15/649,411, Final OA dated Dec. 23, 2019, 19 pages.
U.S. Appl. No. 14/885,888, Final Office Action dated Jan. 2, 2020, 2019, 21 pages.
U.S. Appl. No. 14/542,426, Final OA dated Dec. 20, 2019, 19 pages.
U.S. Appl. No. 15/261,661, Non-Final Rejection dated Jan. 16, 2020, 20 pages.
U.S. Appl. No. 14/535,171, Non-Final Rejection dated Jan. 23, 2020, 20 pages.
U.S. Appl. No. 13/041,006, Final Rejection dated Jan. 27, 2020; 10 pages.
U.S. Appl. No. 13/889,513, Non-Final OA, mailed on Jan. 28, 2020, 27 pages.
U.S. Appl. No. 14/542,423, Final Office Action dated May 18, 2020, 21 pages.
U.S. Appl. No. 13/041,006, Final Rejection, dated Jan. 7, 2021; 30 pages.
U.S. Appl. No. 14/885,888, Final Office Action dated Mar. 30, 2021, 25 pages.
U.S. Appl. No. 13/889,513, Notice of Abandonment, dated Sep. 25, 2020, 2 pages.
U.S. Appl. No. 14/535,171, Non-Final Office Action dated Oct. 5, 2020, 21 pages.
U.S. Appl. No. 14/542,423, Non-Final Office Action dated Oct. 6, 2020, 21 pages.
U.S. Appl. No. 15/620,701, Non-Final Office Action dated Oct. 21, 2020, 20 pages.
U.S. Appl. No. 13/041,006, Non-Final Rejection dated Jun. 12, 2020; 29 pages.
U.S. Appl. No. 15/620,701, Final Office Action dated Jun. 22, 2020, 25 pages.
EPO Communication pursuant to Rules 71(3) dated Jun. 23, 2020, 57 pages.
U.S. Appl. No. 15/649,411, Non-Final Office Action, dated Jul. 29, 11 pages.
U.S. Appl. No. 14/885,888, Non-Final Office Action dated Aug. 6, 2020, 2019, 21 pages.
U.S. Appl. No. 14/542,426, Non-Final Office Action dated Aug. 6, 2020, 2019, 19 pages.
U.S. Appl. No. 15/261,661, Non-Final Rejection dated Sep. 3, 2020, 22 pages.
U.S. Appl. No. 16/726,337, Final Office Action dated Sep. 7, 2021, 68 pages.
U.S. Appl. No. 15/620,701, Final Office Action dated Oct. 26, 2021, 22 pages.
U.S. Appl. No. 16/726,337, Non-Final Office Action dated May 17, 2021; 79 pages.
U.S. Appl. No. 15/261,661, Final Office Action dated May 19, 2021, 25 pages.

(56) References Cited

OTHER PUBLICATIONS

U.S. Appl. No. 14/535,171, Final Office Action dated May 19, 2021, 22 pages.
U.S. Appl. No. 14/542,423, Final Office Action dated May 19, 2021, 21 pages.
U.S. Appl. No. 15/649,411, Non-Final Office Action, dated May 19, 2021, 21 pages.
U.S. Appl. No. 14/542,426, Final Office Action dated Jun. 1, 2021, 20 pages.
U.S. Appl. No. 15/620,701, Non-Final Office Action dated Jun. 6, 2021, 22 pages.
U.S. Appl. No. 13/041,006, Non-Final Office Action dated Jul. 16, 2021; 32 pages.
U.S. Appl. No. 14/885,888, Non-Final Office Action, dated Dec. 24, 2021, 28 pages.
U.S. Appl. No. 13/041,006, Final Office Action, dated Jan. 27, 2022; 32 pages.
U.S. Appl. No. 15/649,411, Notice of Allowance, dated Feb. 2, 2022, 30 pages.
U.S. Appl. No. 14/535,171, Notice of Allowance, dated Feb. 9, 2022, 30 pages.
U.S. Appl. No. 15/261,661, Notice of Allowance, dated Mar. 10, 2022; 48 pages.
U.S. Appl. No. 14/542,423, Notice of Allowance, dated Mar. 16, 2022; 29 pages.

* cited by examiner

ASSESSING EFFECTIVENESS OF CPR

CROSS-REFERENCE TO RELATED APPLICATIONS

This application claims the benefit, under 35 U.S.C. § 119 (e), of the following provisional applications: provisional U.S. Patent Application No. 62/064,816, filed Oct. 16, 2014 by Mulligan et al. and entitled "Assessing the Effectiveness of CPR" (referred to hereinafter as the "'816 Application"), and provisional U.S. Patent Application No. 62/064,809, filed Oct. 16, 2014 by Mulligan et al. and entitled "Rapid Detection of Bleeding During Fluid Resuscitation" (referred to hereinafter as the "'809 Application"), both of which are incorporated herein by reference. This application may be related to co-pending U.S. patent application Ser. No. 14/885,888 filed on a date even herewith by Mulligan et al. and entitled "Rapid Detection of Bleeding Before, During, and After Fluid Resuscitation", which claims priority to the '809 and the '816 Applications.

This application may be related to the following applications: U.S. patent application Ser. No. 14/542,423, filed Nov. 14, 2014 by Mulligan et al. and entitled "Noninvasive Monitoring for Fluid Resuscitation" (referred to hereinafter as the "'423 Application"), which claims priority to provisional U.S. Patent Application No. 61/904,436, filed Nov. 14, 2013 by Mulligan et al. and entitled "Noninvasive Monitoring for Fluid Resuscitation" (referred to hereinafter as the "'436 Application"); and U.S. patent application Ser. No. 14/542,426, filed Nov. 14, 2014 by Mulligan et al. and entitled "Noninvasive Hydration Monitoring" (referred to hereinafter as the "'426 Application"), which claims priority to provisional U.S. Patent Application No. 61/905,727, filed Nov. 18, 2013 by Mulligan et al. and entitled "Noninvasive Hydration Monitoring" (referred to hereinafter as the "'727 Application"), all of which are incorporated herein by reference.

This application may be related to U.S. patent application Ser. No. 14/535,171, filed Nov. 6, 2014 by Mulligan et al. and entitled, "Noninvasive Predictive and/or Estimative Blood Pressure Monitoring" (referred to hereinafter as the "'171 Application"), which claims priority to provisional U.S. Patent Application No. 61/900,980, filed Nov. 6, 2013 by Mulligan et al. and entitled "Noninvasive Predictive and/or Estimative Blood Pressure Monitoring" (referred to hereinafter as the "'980 Application"), both of which are incorporated herein by reference.

This application may be related to U.S. patent application Ser. No. 13/554,483, filed Jul. 20, 2012 by Grudic et al. and entitled, "Hemodynamic Reserve Monitor and Hemodialysis Control" (referred to hereinafter as the "'483 Application"), which claims priority to provisional U.S. Patent Application No. 61/510,792, filed Jul. 22, 2011 by Grudic et al. and entitled "Cardiovascular Reserve Monitor" (referred to hereinafter as the "'792 Application"), and provisional U.S. Patent Application No. 61/614,426, filed Mar. 22, 2012 by Grudic et al. and entitled "Hemodynamic Reserve Monitor and Hemodialysis Control" (referred to hereinafter as the "'426 Application"), all of which are hereby incorporated by reference.

The '483 application is also a continuation-in-part of U.S. patent application Ser. No. 13/041,006, filed Mar. 4, 2011 by Grudic et al. and entitled "Active Physical Perturbations to Enhance Intelligent Medical Monitoring", referred to hereinafter as the "'006 application"), which claims priority to provisional U.S. Patent Application No. 61/310,583, filed Mar. 4, 2010, by Grudic and entitled "Active Physical Perturbations to Enhance Intelligent Medical Monitoring", referred to hereinafter as the "'583 application"), both of which are hereby incorporated by reference. The '006 application is a continuation-in-part of U.S. patent application Ser. No. 13/028,140 (the "'140 application," now U.S. Pat. No. 8,512,260), filed Feb. 15, 2011 by Grudic et al. and entitled "Statistical, Noninvasive Measurement of Intracranial Pressure" which claims priority to provisional U.S. Patent Application No. 61/305,110, filed Feb. 16, 2010, by Moulton et al. and entitled "Statistical, Noninvasive Method for Predicting Intracranial Pressure", referred to hereinafter as the "'110 application"), both of which are hereby incorporated by reference.

The '140 application is a continuation in part of International Application No. PCT/US2009/062119 (the "'119 application"), filed Oct. 26, 2009 by Grudic et al. and entitled "Long Term Active Learning from Large Continually Changing Data Sets", which claims priority to provisional U.S. Patent Application No. 61/252,978 filed Oct. 19, 2009, provisional U.S. Patent Application Nos. 61/166,499, 61/166,486, and 61/166,472, filed Apr. 3, 2009, and provisional U.S. Patent Application No. 61/109,490, filed Oct. 29, 2008, each of which is hereby incorporated by reference.

The respective disclosures of these applications/patents (collectively, the "Related Applications"), which are commonly assigned, are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under grant number 0535269 awarded by the National Science Foundation; grant number FA8650-07-C-7702 awarded by the Air Force Research Laboratory; and grant numbers W81XWH-09-C-1060 and W81XWH-09-1-0750 awarded by Army Medical Research Material and Command. The government has certain rights in the invention.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, tools and techniques for medical monitoring, and more particularly, to tools and techniques that can provide assessment of effectiveness of CPR before, during, and after performance of CPR, in some cases, in real-time.

BACKGROUND

Cardiopulmonary Resuscitation ("CPR") can be an effective technique to continue circulatory function during a cardiac arrest. Several variables, however, including without limitation the caregiver's technique and the patient's condition, can affect the effectiveness of the therapy, and it can be difficult to determine whether CPR is effectively serving its purpose.

Thus, there is a need for an automated, noninvasive device that can provide feedback to a caregiver on the effectiveness of CPR in a particular situation, in some instances, in real-time.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Overview

Figure 1A:
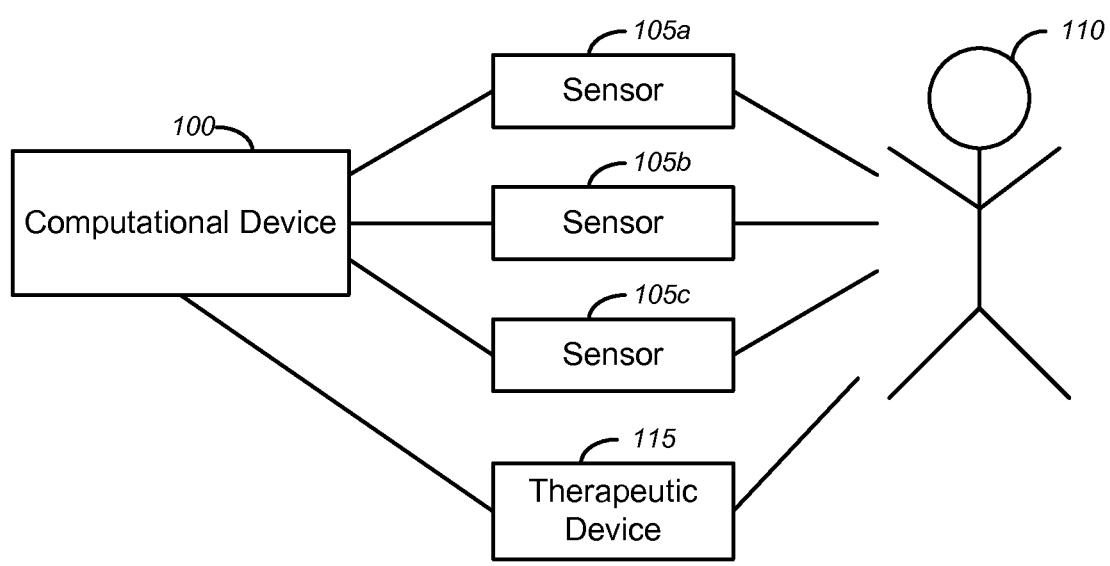
FIG. 1A is a schematic diagram illustrating a system for estimating compensatory reserve, in accordance with various embodiments.

Various embodiments can assess and provide feedback on the effectiveness of CPR (e.g., whether the CPR is effectively delivering oxygenated blood to the patient's tissues, in particular the brain). In an aspect, such assessment can be performed noninvasively. In some embodiments, the assessment can be based on a calculation (or estimation) of a patient's compensatory reserve index ("CRI," also referred to herein and in the Related Applications as "cardiac reserve index" or "hemodynamic reserve index" ("HDRI")). In other cases, the assessments might be based on raw waveform data (e.g., PPG waveform data) captured by a sensor on the patient (such as the sensors described in the Related Applications, for example). In further cases, a combination of waveform data and calculated/estimated CRI can be used to assess effectiveness of CPR efforts.

In other aspects, such functionality can be provided by and/or integrated with systems and devices (such as a cardiac reserve monitor), tool, techniques, methods, and software described in the Related Applications, including in particular the '483 application. For example, various operations described in accordance with the methods disclosed by the Related Applications can be employed in a method of assessing effectiveness of resuscitation and/or calculating an amount of fluid needed for effective resuscitation. Similarly, such techniques can be performed by the systems and/or embodied by the software products described in the Related Applications.

An embodiment can include a system that comprises one or more sensors placed on the patient and a computer system (such as those described in the Related Applications) that performs a method for using sensor data for estimating and predicting (in real-time, after every heartbeat, or as the information is needed) one or more of the relevant parameters outlined above. Other embodiments can comprise the computer system programmed to perform such a method, an apparatus comprising instructions to program a computer to perform such a method, and/or such a method itself.

A sensor may include but is not limited to any of the following: a noninvasive blood pressure sensor such as the Nexfin (BMEYE, B.V.) or Finometer (Finapres Medical Systems B.V.); invasive arterial blood pressure, using an arterial catheter; invasive central venous pressure; invasive or noninvasive intracranial pressure monitor; EEG (electroencephalograph); cardiac monitor (EKG); transcranial Doppler sensor; transthoracic impedance plethysmography; pulse oximetry; a sensor generating a photoplethysmograph (PPG) waveform; near infrared spectroscopy; electronic stethoscope; and/or the like.

The '816 application describes several exemplary embodiments, but various embodiments are not limited to those described in the '816 application. For example, FIG. 1 of the '816 application illustrates an exemplary sensor that can be used to collect waveform data for analysis, but other sensors could be used as well. Similarly, the '816 application describes several techniques for assessing the effectiveness of CPR on a patient. Many such techniques depend on an estimate of a patient's CRI, which can be calculated using the techniques described in the '483 application. It should be appreciated, however, that other embodiments of assessing the effectiveness of CPR and/or of estimating CRI can be employed in various embodiments.

Thus, in one aspect, a method can include receiving data from such a sensor and analyzing such data using techniques including, but not limited to, analyzing the data using models described in the Related Applications. Merely by way of example, a model might be constructed using test subject data from a study, such as the LBNP study, which can be used to predict or estimate a CRI (or HDRI) value, as described in the Related Applications, and in particular in the '483 application. From this calculated value of CRI (or, in some embodiments, from the waveform data itself, alone or in combination with the CRI value), various embodiments can assess and provide feedback on the effectiveness of CPR, for example, using the techniques described in the '816 application.

For example, in one embodiment, a method might comprise capturing waveform data from a patient with the sensor before, during, and/or after CPR is performed and/or calculating a CRI value for the patient at these times. In some cases, the variation in CRI values obtained during the procedure can be used to assess the effectiveness of CPR. For instance, the standard deviation of the CRI values during the recording and/or the difference in CRI values before, during, and/or after performance of CPR can be used to estimate or assess the effectiveness of CPR, as detailed in the '816 application.

Some embodiments further provide feedback on the effectiveness of CPR. For example, one embodiment might provide feedback in the form of a classification (such as "very good," "good," or "poor") of the effectiveness of CPR. Other embodiments might provide feedback indicating a number within a range (e.g., between 0 to 100) indicating the effectiveness of the CPR.

The following detailed description illustrates a few exemplary embodiments in further detail to enable one of skill in the art to practice such embodiments. The described examples are provided for illustrative purposes and are not intended to limit the scope of the invention. For the purposes of this disclosure, it should be recognized that a node could be "virtual" or supported on a hypervisor or Host system, or could be a physical node or network device within a network. In most cases, the figures illustrate bridging a virtual path and possibly a node (virtual machine) across the path or between two physical nodes. However, it should be understood that the "swapping" of paths via orchestration can occur in any combination of physical and/or virtual nodes, physical and/or virtual links, or the like.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

In an aspect, a system might be provided that comprises one or more sensors to obtain physiological data from a patient and a computer system in communication with the one or more sensors. The computer system might comprise one or more processors and a non-transitory computer readable medium in communication with the one or more processors. The computer readable medium might have encoded thereon a set of instructions executable by the one or more processors to cause the computer system to receive the physiological data from the one or more sensors, analyze the physiological data, assess effectiveness of a cardiopulmonary resuscitation ("CPR") procedure on the patient, and display, on a display device, an indication of the effectiveness of the CPR procedure on the patient.

In another aspect, a method might be provided that comprises monitoring, with one or more sensors, physiological data of a patient, analyzing, with a computer system, the physiological data, and assessing effectiveness of a cardiopulmonary resuscitation ("CPR") procedure on the patient, based at least in part on the analyzed physiological data. The method might further comprise displaying, on a display device, an indication of the effectiveness of the CPR procedure on the patient.

In some instances, one or more of monitoring the physiological data, analyzing the physiological data, assessing effectiveness of the CPR procedure on the patient, or displaying the indication of the effectiveness of the CPR procedure on the patient are performed in real-time. In some cases, assessing effectiveness of a CPR procedure on the patient might comprise assessing the effectiveness of the CPR procedure on the patient, based on one or more values of compensatory reserve index ("CRI") estimated based on the received physiological data. According to some embodiments, the one or more values of CRI are estimated based on physiological data that are at least one of received before, received during, or received after the CPR procedure.

In some embodiments, the one or more values of CRI might comprise a plurality of values of CRI. In some cases, assessing effectiveness of a CPR procedure on the patient might comprise assessing the effectiveness of the CPR procedure on the patient based at least in part on one or more of an average value of CRI over a particular period of time, a standard deviation of at least some of the plurality of values of CRI, a skewness of at least some of the plurality of values of CRI, a rate of change of at least some of the plurality of values of CRI, a rate of rate change of at least some of the plurality of values of CRI, and/or a difference between at least some of the plurality of values of CRI. In some instances, the indication is selected from a plurality of categories including "very good," "good," and "poor." According to some embodiments, the indication is a number on a scale from 0 to 100. In some embodiments, a value of 0 might indicate that the CPR procedure is ineffectively performed, while a value of 100 might indicate that the CPR procedure is effectively performed.

In some cases, estimating a CRI of the patient comprises estimating a CRI by comparing the physiological data to a model constructed using the following formula:

$$CRI(t) = 1 - \frac{BLV(t)}{BLV_{HDD}},$$

where CRI(t) is the compensatory reserve at time t, BLV(t) is an intravascular volume loss of a test subject at time t, and $BLV_{HDD}$ is an intravascular volume loss at a point of hemodynamic decompensation of the test subject. In some embodiments, the physiological data comprises waveform data and wherein estimating the CRI comprises comparing the waveform data with one or more sample waveforms generated by exposing one or more test subjects to state of hemodynamic decompensation or near hemodynamic decompensation, or a series of states progressing towards hemodynamic decompensation, and monitoring physiological data of the test subjects.

In some instances, the physiological data might comprise waveform data, and estimating the CRI might comprise comparing the waveform data with a plurality of sample waveforms, each of the sample waveforms corresponding to a different value of the CRI to produce a similarity coefficient expressing a similarity between the waveform data and each of the sample waveforms, normalizing the similarity coefficients for each of the sample waveforms, and summing the normalized similarity coefficients to produce an estimated CRI value for the patient.

According to some embodiments, assessing effectiveness of CPR is based on a fixed time history of monitoring the physiological data of the patient. Alternatively, assessing effectiveness of CPR is based on a dynamic time history of monitoring the physiological data of the patient. In some instances, at least one of the one or more sensors is selected from the group consisting of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, and an electronic stethoscope.

Merely by way of example, in some embodiments, physiological data might comprise at least one of blood pressure waveform data, plethysmograph waveform data, or photoplethysmograph (PPG) waveform data.

In some cases, analyzing the physiological data might comprise analyzing the physiological data against a pre-existing model. In some embodiments, the method might further comprise generating the pre-existing model prior to analyzing the physiological data. In some instances, generating the pre-existing model might comprise receiving data pertaining to one or more physiological parameters of a test subject to obtain a plurality of physiological data sets, directly measuring one or more physiological states of the test subject with a reference sensor to obtain a plurality of physiological state measurements, and correlating the received data with the physiological state measurements of the test subject. According to some embodiments, the one or more physiological states comprises reduced circulatory system volume.

In some instances, the method might further comprise inducing the physiological state of reduced circulatory system volume in the test subject. In some cases, inducing the physiological state comprise at least one of subjecting the test subject to lower body negative pressure ("LBNP"), subjecting the test subject to dehydration, and/or the like. In some embodiments, the one or more physiological states might comprise at least one of a state of cardiovascular collapse or near-cardiovascular collapse, a state of euvolemia, a state of hypervolemia, a state of dehydration, and/or the like.

According to some embodiments, correlating the received data with the physiological state measurements of the test subject might comprise identifying a most predictive set of signals $S_k$ out of a set of signals $s_1, s_2, \ldots, s_D$ for each of one or more outcomes $o_k$, autonomously learning a set of probabilistic predictive models $\hat{o}_k = M_k(S_k)$, and repeating the operation of autonomously learning incrementally from data that contains examples of values of signals $s_1, s_2, \ldots, s_D$ and corresponding outcomes $o_1, o_2, \ldots, o_K$. Here, the most-predictive set of signals $S_k$ corresponds to a first data set representing a first physiological parameter, and each of the one or more outcomes $o_k$ represents a physiological state measurement, while $\hat{o}_k$ is a prediction of outcome $o_k$ derived from a model $M_k$ that uses as inputs values obtained from the set of signals $S_k$.

In yet another aspect, an apparatus might be provided that comprises a non-transitory computer readable medium that has encoded thereon a set of instructions executable by one or more computers to cause the apparatus to receive physiological data from one or more sensors, analyze the physiological data, assess effectiveness of a cardiopulmonary resuscitation ("CPR") procedure on the patient, and display, on a display device, an indication of the effectiveness of the CPR procedure on the patient.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Compensatory Reserve Index ("CRI")

Various embodiments can assess the effectiveness of fluid intake hydration, where effectiveness can be defined, but not limited to, as leading to a better hydration state or maintain an optimal hydration state. In one aspect, optimal hydration might be defined as a fluid state that maximized some performance index/measure, perhaps indicated by the patient's compensatory reserve index ("CRI," also referred to herein and in the Related Applications as "cardiac reserve index" or "hemodynamic reserve index" ("HDRI"), all of which should be considered synonymous for purposes of this disclosure). (While the term, "patient," is used herein for convenience, that descriptor should not be considered limiting, because various embodiments can be employed both in a clinical setting and outside any clinical setting, such as by an athlete before, during, or after an athletic contest or training, a person during daily activities, a soldier on the battlefield, etc. Thus, the term, "patient," as used herein, should be interpreted broadly and should be considered to be synonymous with "person.") In other cases, the assessments might be based on raw waveform data (e.g., PPG waveform data) captured by a sensor on the patent (such as the sensors described below and the Related Applications, for example). In further cases, a combination of waveform data and calculated/estimated CRI can be used to calculate the effectiveness of hydration and/or the amount of fluid needed for effective hydration. In other aspects, such functionality can be provided by and/or integrated with systems, devices (such as a cardiac reserve monitor and/or wrist-worn sensor device), tools, techniques, methods, and software described below and in the Related Applications.

For example, one set of embodiments provides methods. An exemplary method might comprise monitoring, with one or more sensors, physiological data of a patient. The method might further comprise analyzing, with a computer system, the physiological data. Many different types of physiological data can be monitored and/or analyzed by various embodiments, including without limitation, blood pressure waveform data, plethysmograph waveform data, photoplethysmograph ("PPG") waveform data (such as that generated by a pulse oximeter), and/or the like. In an aspect of some embodiments, analyzing the physiological data might comprise analyzing the data against a pre-existing model. In some cases, the method can further comprise assessing the effectiveness of hydration efforts, and/or displaying (e.g., on a display device) an assessment of the effectiveness of the hydration efforts. Such an assessment can include, without limitation, an estimate of the effectiveness at a current time, a prediction of the effectiveness at some point in the future, an estimate and/or prediction of a volume of fluid necessary for effective hydration, an estimate of the probability a patient requires fluids, etc.

An apparatus, in accordance with yet another set of embodiments, might comprise a computer readable medium having encoded thereon a set of instructions executable by one or more computers to perform one or more operations. In some embodiments, the set of instructions might comprise instructions for performing some or all of the operations of methods provided by certain embodiments.

A system, in accordance with yet another set of embodiments, might comprise one or more processors and a computer readable medium in communication with the one or more processors. The computer readable medium might have encoded thereon a set of instructions executable by the computer system to perform one or more operations, such as the set of instructions described above, to name one example. In some embodiments, the system might further comprise one or more sensors and/or a therapeutic device, either or both of which might be in communication with the processor and/or might be controlled by the processor. Such sensors can include, but are not limited to, a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, and/or an electronic stethoscope.

CRI for Determining Effectiveness of CPR

A set of embodiments provides methods, systems, and software that can be used, in many cases noninvasively, to quickly and accurately assess CPR effectiveness in resuscitating a patient in cardiac arrest (e.g., before, during, and/or after CPR is performed). Such an assessment can include, without limitation, an estimate of the effectiveness at a current time, a prediction of the effectiveness at some point in the future, an estimate and/or prediction of a volume of fluid necessary for effective hydration, an estimate of the probability a patient requires fluids, an estimate and/or assessment of CPR effectiveness (e.g., before, during, and/or after resuscitation), etc. In a particular set of embodiments, a device, which can be worn on the patient's body, can include one or more sensors that monitor a patient's physiological parameters. The device (or a computer in communication with the device) can analyze the data captured by the sensors and compare such data with a model (which can be generated in accordance with other embodiments) to assess the effectiveness of hydration, as described in further detail in the '426 application, and/or to assess CPR effectiveness (e.g., before, during, and/or after resuscitation).

Different embodiments can measure a number of different physiological parameters from the patient, and the analysis of those parameters can vary according to which parameters are measured (and which, according to the generated model, are found to be most predictive of the effectiveness of hydration, including the probability of the need for hydration and/or the volume of fluids needed, or most predictive of blood loss). In some cases, the parameters themselves (e.g., continuous waveform data captured by a photoplethysmograph) can be analyzed against the model to make assessments of hydration effectiveness or assessments of CPR effectiveness (e.g., before, during, and/or after resuscitation). In other cases, physiological parameters can be derived from the captured data, and these parameters can be used Merely by way of example, as described further below and the '483 application (already incorporated by reference), direct physiological data (captured by sensors) can be used to estimate a value of CRI, and this value of CRI can be used to assess the effectiveness of hydration and/or to assess effectiveness of CPR (e.g., before, during, and/or after resuscitation). In yet other cases, the derived CRI values and raw sensor data can be used together to perform such assessments.

For example, the '483 application describes a compensatory reserve monitor (also described as a cardiac reserve monitor or hemodynamic reserve monitor) that is able to estimate the compensatory reserve of a patient. In an aspect, this monitor quickly, accurately and/or in real-time can determine the effectiveness of CPR that is being performed or was performed on a patient. In another aspect, the device can simultaneously monitor the patient's compensatory reserve by tracking the patient's CRI, to appropriately and effectively guide hydration and ongoing patient care. The same device (or a similar device) can also include advanced functionality to assess the effectiveness of hydration, based on the monitored CRI values, as explained in further detail in the '426 application, and/or to rapidly assess CPR effectiveness (e.g., before, during, and/or after resuscitation).

CRI is a hemodynamic parameter that is indicative of the individual-specific proportion of intravascular fluid reserve remaining before the onset of hemodynamic decompensation. CRI has values that range from 1 to 0, where values near 1 are associated with normovolemia (normal circulatory volume) and values near 0 are associated with the individual specific circulatory volume at which hemodynamic decompensation occurs.

The mathematical formula of CRI, at some time "t" is given by the following equation:

$$CRI(t) = 1 - \frac{BLV(t)}{BLV_{HDD}} \quad \text{(Eq. 1)}$$

Where BLV(t) is the intravascular volume loss ("BLV," also referred to as "blood loss volume" in the Related Applications) of a person at time "t," and $BLV_{HDD}$ is the intravascular volume loss of a person when they enter hemodynamic decompensation ("HDD"). Hemodynamic decompensation is generally defined as occurring when the systolic blood pressure falls below 70 mmHg. This level of intravascular volume loss is individual specific and will vary from subject to subject.

Lower body negative pressure (LBNP) in some linear or nonlinear relationship λ with intravascular volume loss:

$$BLV = \lambda \cdot LBNP \quad (Eq. 2)$$

can be used in order to estimate the CRI for an individual undergoing a LBNP experiment as follows:

$$CRI = 1 - \frac{BLV(t)}{BLV_{HDD}} \approx 1 - \frac{\lambda \cdot LBNP(t)}{\lambda \cdot LBNP_{HDD}} = 1 - \frac{LBNP(t)}{LBNP_{HDD}} \quad (Eq. 3)$$

Where LBNP (t) is the LBNP level that the individual is experiencing at time "t," and, $LBNP_{HDD}$ is the LNPB level that the individual will enter hemodynamic decompensation.

Using either CRI data, raw (or otherwise processed) sensor data, or both, various embodiments can assess the effectiveness of hydration. In one embodiment, the assessment of CPR effectiveness ("$CPR_{eff}$") can be expressed as a value between 0 and 1; when $CPR_{eff}=100$, CPR effectiveness is certain, when $CPR_{eff}=0$, CPR ineffectiveness is certain, and when $CPR_{eff}$ is a value between 100 and 0, the value is indicative of higher or lower relative effectiveness of CPR, perhaps due to ongoing cardiopulmonary issues before, during, and/or after resuscitation. (Of course, other embodiments can scale the value of $CPR_{eff}$ differently). In an aspect of some embodiments, a general expression for the estimate of as follows:

$$CPR_{eff} = f_{CPR_{eff}}(CRI_t, FV_t, S_t) \quad (Eq. 4)$$

Where $CPR_{eff}$ is a measure or an estimate of effectiveness of CPR, $f_{CPR_{eff}}(CRI_t, FV_t, S_t)$ is an algorithm embodied by a model generated empirically, e.g., using the techniques described with respect to FIG. 4 below, and/or in the Related Applications, $CRI_t$ is a time history of CRI values (which can range from a single CRI value to many hours of CRI values), $FV_t$ is a time history of fluid volume being given to the patient (which can range from a single value to many hours of values), and $S_t$ is a time history of raw sensor values, such as physiological data measured by the sensors, as described elsewhere herein (which can range from one value to many hours of values).

The functional form of Eq. 4 is similar to but not limited to the form of the CRI model in the sense that time histories of ($CRI_t$, $FV_t$, $S_t$) data gathered from human subjects at various levels of $CPR_{eff}$ are compared to time histories of ($CRI_t$, $FV_t$, $S_t$) for the current patient being monitored. The estimated $CPR_{eff}$ for the current patient is then that which is the closest in ($CRI_t$, $FV_t$, $S_t$) space to the previously gathered data.

While Eq. 4 is the general expression for $CPR_{eff}$, various embodiments might use subsets of the parameters considered in Eq. 4. For instance, in one embodiment, a model might consider only the volume of fluid and CRI data, without accounting for raw sensor input. In that case, $CPR_{eff}$ can be calculated as follows:

$$CPR_{eff} = f_{CPR_{eff}}(CRI_t, FV_t) \quad (Eq. 5)$$

Similarly, some models might estimate $CPR_{eff}$ based on sensor data, rather than first estimating CRI, in which case, $CPR_{eff}$ can be expressed thusly:

$$CPR_{eff} = f_{CPR_{eff}}(FV_t, S_t) \quad (Eq. 6)$$

The choice of parameters to use in modeling $CPR_{eff}$ is discretionary, and it can depend on what parameters are shown (e.g., using the techniques of FIG. 4, below) to result in the best prediction of $CPR_{eff}$.

In another aspect, the effectiveness of hydration can be assessed by estimating or predicting the volume, V, of fluid necessary for effective hydration of the patient. This volume, V, can indicate a volume of fluid needed for full hydration if therapy has not yet begun, and/or it can indicate a volume remaining for fully effective hydration if therapy is underway. Like $CPR_{eff}$, the value of V can be estimated/predicted using the modeling techniques described herein and in the Related Applications. In a general case, V can be expressed as the following:

$$V = f_V(CRI_t, FV_t, S_t) \quad (Eq. 7)$$

where V is an estimated volume of fluid needed by a patient need to prevent over or under hydration, $f_V(CRI_t, FV_t, S_t)$ is an algorithm embodied by a model generated empirically, e.g., using the techniques described with respect to FIG. 4 below, and/or in the Related Applications, $CRI_t$ is a time history of CRI values, $FV_t$ is a time history of fluid volume being given to the patient, and $S_t$ is a time history of physiological data received from the one or more sensors.

As with the estimate of $CPR_{eff}$, various embodiments can employ subsets of the parameters used in the general expression of Eq.7. Thus, different embodiments might calculate V as follows:

$$V = f_V(CRI_t, FV_t) \quad (Eq. 8)$$

or $$V = f_V(FV_t, S_t) \quad (Eq. 9)$$

Yet another way of assessing effectiveness of hydration (which can even include assessing the need for hydration) is estimating the probability $P_f$ that the patient requires fluids; this probability can estimate the likelihood that the patient requires hydration if therapy has not been initiated, and/or, if hydration therapy is underway, the probability can estimate the likelihood that further hydration is necessary. The value of this probability, which can be expressed, e.g., as a percentage, as a decimal value between 0 and 1, etc. can be estimated using the following expression:

$$P_f = f_{P_f}(CRI_t, S_t) \quad (Eq. 10)$$

where $P_f$ is the estimated probability that the patient requires fluid, $f_{P_f}(CRI_t, S_t)$ is a relationship derived based on empirical study, $CRI_t$ is a time history of CRI values, and $S_t$ is a time history of physiological data received from the one or more sensors. Once again, this general expression can be employed, in various embodiments, using subsets of the parameters in the general expression, such as the following:

$$P_f = f_{P_f}(CRI_t) \quad (Eq. 11)$$

or $$P_f = f_{P_f}(S_t) \quad (Eq. 12)$$

Figure 2A:
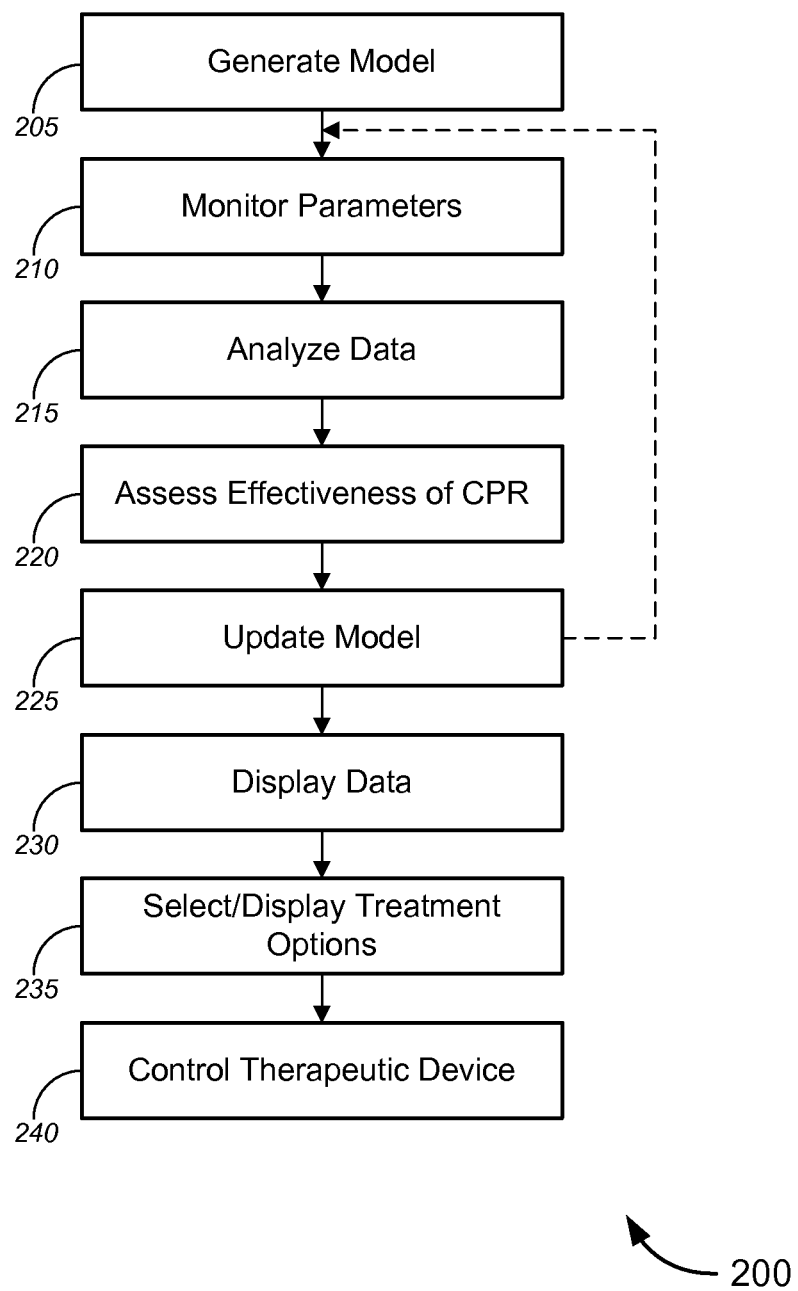
FIG. 2A is a process flow diagram illustrating a method of assessing effectiveness of CPR, in accordance with various embodiments.
Figure 2B:
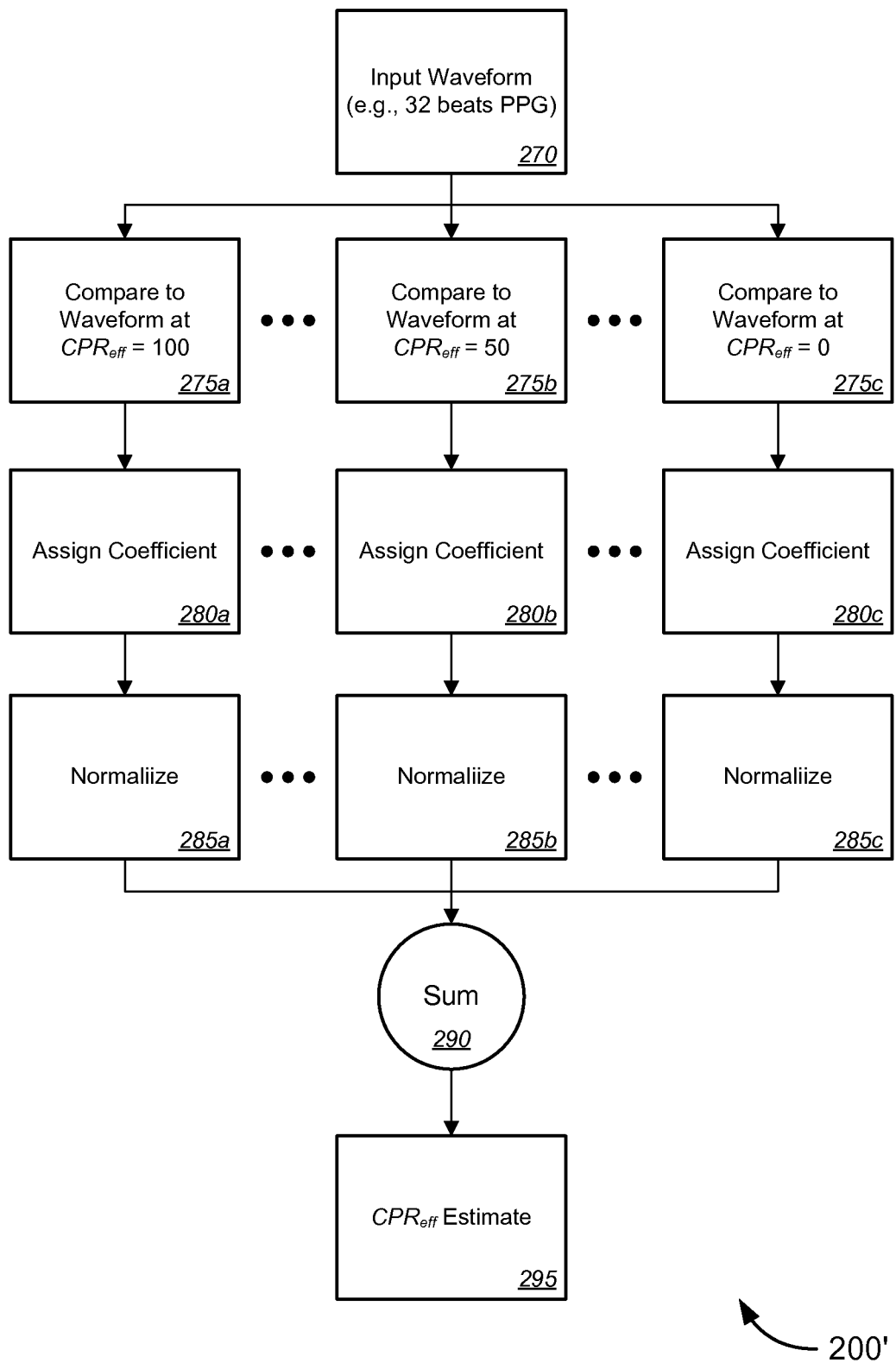
FIG. 2B illustrates a technique for assessing effectiveness of CPR, in accordance with various embodiments.

In the estimate of any of $CPR_{eff}$, V, or $P_f$, the function $f$ expresses a relationship that is derived based on empirical study. In a set of embodiments, for example, various sensor data can be collected from test subjects before, during, and/or after hydration efforts, during hemorrhaging, or under other conditions that might simulate such situations. This sensor data can be analyzed to develop models, using techniques similar to those of FIG. 4 below, which can then be used to estimate various assessments of hydration effectiveness, using, e.g., the methods described below with respect to FIGS. 2 and 3.

A measure of CRI, $CPR_{eff}$, V, and/or $P_f$ can be useful in a variety of clinical settings, including but not limited to: 1)

acute blood loss volume due to injury or surgery; 2) acute circulatory volume loss due to hemodialysis (also called intradialytic hypotension); and 3) acute circulatory volume loss due to various causes of dehydration (e.g. reduced fluid intake, vomiting, dehydration, etc.). A change in CRI can also herald other conditions, including without limitation changes in blood pressure, general fatigue, overheating and certain types of illnesses. Accordingly, the tools and techniques for estimating and/or predicting CRI can have a variety of applications in a clinical setting, including without limitation diagnosing such conditions.

Moreover, measures of CRI, $CPR_{eff}$, V, and/or $P_f$ can have applicability outside the clinical setting. For example, an athlete can be monitored (e.g., using a wrist-wearable hydration monitor) before, during, or after competition or training to ensure optimal performance (and overall health and recovery). In other situations, a person concerned about overall wellbeing can employ a similar hydration monitor to ensure that he or she is getting enough (but not too much) fluid, ill infants or adults can be monitored while ill to ensure that symptoms (e.g., vomiting, diarrhea) do not result in dehydration, and the like. Similarly, soldiers in the field (particularly in harsh conditions) can be monitored to ensure optimal operational readiness.

In various embodiments, a hydration monitor, compensatory reserve monitor, a wrist-wearable sensor device, and/or another integrated system can include, but is not limited to, some or all of the following functionality, as described in further detail herein and in the Related Applications:

A. Estimating and/or displaying intravascular volume loss to hemodynamic decompensation (or cardiovascular collapse).

B. Estimating, predicting and/or displaying a patient's compensatory reserve as an index that is proportional to an approximate measure of intravascular volume loss to CV collapse, recognizing that each patient has a unique reserve capacity.

C. Estimating, predicting and/or displaying a patient's compensatory reserve as an index with a normative value at euvolemia (for example, CRI=1), representing a state in which the patient is normovolemic; a minimum value (for example, CRI=0) which implies no circulatory reserve and that the patient is experiencing CV collapse; and/or an excess value (for example, CRI>1) representing a state in which the patient is hypervolemic; the patient's normalized compensatory reserve can be displayed on a continuum between the minimum and maximum values (perhaps labeled by different symbols and/or colors depending on where the patient falls on the continuum).

D. Determining and/or displaying a probability that bleeding or intravascular volume loss has occurred.

E. Displaying an indicator that intravascular volume loss has occurred and/or is ongoing; as well as other measures of reserve, such as trend lines.

F. Estimating a patient's current blood pressure and/or predicting a patient's future blood pressure.

G. Estimating the current effectiveness of fluid resuscitation efforts.

H. Predicting the future effectiveness of fluid resuscitation efforts.

I. Estimating and/or predicting a volume of fluid necessary for effective resuscitation.

J. Estimating a probability that a patient needs fluids.

K. Estimating a hydration state of a patient or user.

L. Predicting a future hydration state of a patient or user.

M. Estimate and/or predicting a volume of fluid intake necessary for adequate hydration of a patient or user.

N. Estimating a probability that a patient is dehydrated.

In various embodiments, CRI, $CPR_{eff}$, V, and/or $P_f$ estimates can be (i) based on a fixed time history of patient monitoring (for example a 30 second or 30 heart beat window); (ii) based on a dynamic time history of patient monitoring (for example monitoring for 200 minutes, the system may use all sensor information gathered during that time to refine and improve CRI estimates, hydration effectiveness assessments, etc.); (iii) based on either establishing baseline estimates when the patient is normovolemic (no volume loss has occurred); and/or (iv) based on NO baselines estimates when patient is normovolemic.

Certain embodiments can also recommend treatment options, based on the analysis of the patient's condition (including the estimated/predicted blood pressure, probability of bleeding, state of dehydration, and/or the patient's estimated and/or predicted CRI). Treatment options can include, without limitation, such things as optimizing hemodynamics, ventilator adjustments, IV fluid adjustments (e.g., controlling the flow rate of an IV pump or the drip rate of an IV drip), transfusion of blood or blood products, infusion of volume expanders, medication changes, changes in patient position and surgical therapy.

As one example, certain embodiments can be used to control an IV drip, IV pump, or rapid infuser. For instance, an embodiment might estimate the probability that a patient requires fluids and activate such a device in response to that estimate (or instruct a clinician to attach such a device to the patient and activate the device). The system might then monitor the progress of the hydration effort (through continual or periodic assessment of the effectiveness of hydration) and increase/decrease drip or flow rates accordingly.

As another example, certain embodiments can be used as an input for a hemodialysis procedure. For example, certain embodiments can predict how much intravascular (blood) volume can be safely removed from a patient during a hemodialysis process. For example, an embodiment might provide instructions to a human operator of a hemodialysis machine, based on estimates or predictions of the patient's CRI. Additionally and/or alternatively, such embodiments can be used to continuously self-adjust the ultra-filtration rate of the hemodialysis equipment, thereby completely avoiding intradialytic hypotension and its associated morbidity.

As yet another example, certain embodiments can be used to estimate and/or predict a dehydration state (and/or the amount of dehydration) in an individual (e.g., a trauma patient, an athlete, an elder living at home, etc.) and/or to provide treatment (either by providing recommendations to treating personnel or by directly controlling appropriate therapeutic equipment). For instance, if an analytical model indicates a relationship between CRI (and/or any other physiological phenomena that can be measured and/or estimated using the techniques described herein and in the Related Applications) and dehydration state, an embodiment can apply that model, using the techniques described herein, to estimate a dehydration state of the patient.

Specific Exemplary Embodiments

Figure 10:
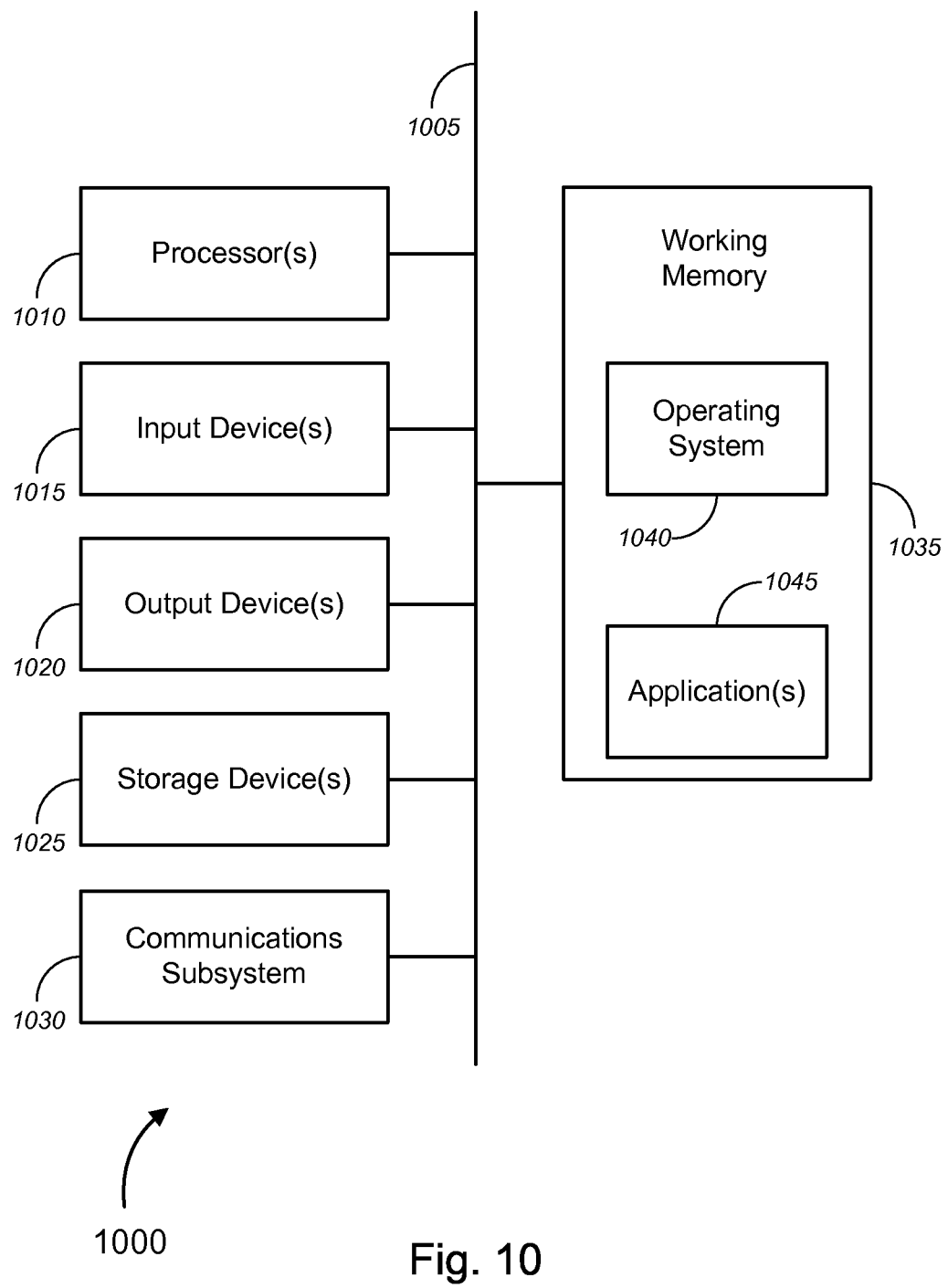
FIG. 10 is a generalized schematic diagram illustrating a computer system, in accordance with various embodiments.

We now turn to the embodiments as illustrated by the drawings. FIGS. 1-10 illustrate some of the features of the method, system, and apparatus for implementing rapid assessment of CPR before, during, and after resuscitation, as referred to above. FIGS. 1-9 illustrate some of the specific (although non-limiting) exemplary features of the method, system, and apparatus for implementing rapid assessment of CPR before, during, and after resuscitation, while FIG. 10 illustrates exemplary system and hardware implementation. The methods, systems, and apparatuses illustrated by FIGS. 1-10 refer to examples of different embodiments that include various components and steps, which can be considered alternatives or which can be used in conjunction with one another in the various embodiments. The description of the illustrated methods, systems, and apparatuses shown in FIGS. 1-10 is provided for purposes of illustration and should not be considered to limit the scope of the different embodiments.

With reference to the figures, FIG. 1A provides a general overview of a system provided by certain embodiments. The system includes a computer system or computational device 100 in communication with one or more sensors 105, which are configured to obtain physiological data from the subject (e.g., animal or human test subject or patient) 110. In one embodiment, the computer system 100 comprises a Lenovo THINKPAD X200, 4 GB of RAM with Microsoft WINDOWS 7 operating system and is programmed with software to execute the computational methods outlined herein. The computational methods can be implemented in MATLAB 2009b and C++ programming languages. A more general example of a computer system 100 that can be used in some embodiments is described in further detail below. Even more generally, however, the computer system 100 can be any system of one or more computers that are capable of performing the techniques described herein. In a particular embodiment, for example, the computer system 100 is capable of reading values from the physiological sensors 105, generating models of physiological state from those sensors, and/or employing such models to make individual-specific estimations, predictions, or other diagnoses, displaying the results, recommending and/or implementing a therapeutic treatment as a result of the analysis, and/or archiving (learning) these results for use in future, model building and predictions.

The sensors 105 can be any of a variety of sensors (including without limitation those described herein) for obtaining physiological data from the subject. An exemplary sensor suite might include a Finometer sensor for obtaining a noninvasive continuous blood pressure waveform, a pulse oximeter sensor, an Analog to Digital Board (National Instruments USB-9215A 16-Bit, 4 channel) for connecting the sensors (either the pulse oximeter and/or the finometer) to the computer system 100. More generally, in an embodiment one or more sensors 105 might obtain, e.g., using one or more of the techniques described herein, continuous physiological waveform data, such as continuous blood pressure. Input from the sensors 105 can constitute continuous data signals and/or outcomes that can be used to generate, and/or can be applied to, a predictive model as described below.

In some cases, the structure or system might include a therapeutic device 115 (also referred to herein as a "physiological assistive device"), which can be controlled by the computer system 100 to administer therapeutic treatment, in accordance with the recommendations developed by analysis of a patient's physiological data. In a particular embodiment, the therapeutic device might comprise hemodialysis equipment (also referred to as a hemodialysis machine), which can be controlled by the computer system 100 based on the estimated CRI of the patient, as described in further detail below. Further examples of therapeutic devices in other embodiments can include a cardiac assist device, a ventilator, an automatic implantable cardioverter defibrillator ("AICD"), pacemakers, an extracorporeal membrane oxygenation circuit, a positive airway pressure ("PAP") device (including without limitation a continuous positive airway pressure ("cPAP") device or the like), an anesthesia machine, an integrated critical care system, a medical robot, intravenous and/or intra-arterial pumps that can provide fluids and/or therapeutic compounds (e.g., through intravenous injection), intravenous drips, a rapid infuser, a heating/cooling blanket, and/or the like.

Figure 1B:
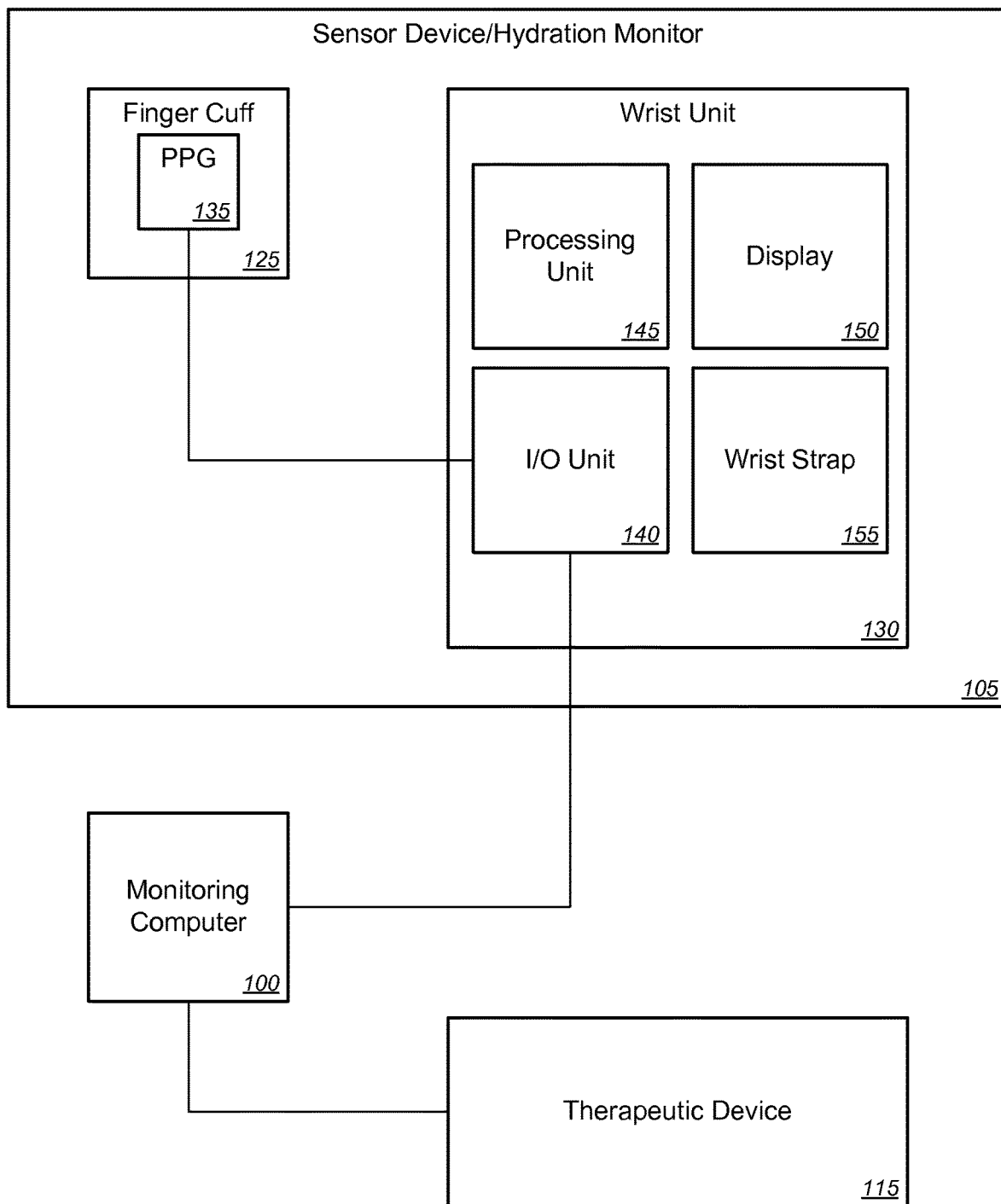
FIG. 1B is a schematic diagram illustrating a sensor system that can be worn on a patient's body, in accordance with various embodiments.

FIG. 1B illustrates in more detail an exemplary sensor device 105, which can be used in the system 100 described above. (It should be noted, of course, that the depicted sensor device 105 of FIG. 1B is not intended to be limiting, and different embodiments can employ any sensor that captures suitable data, including, without limitation, sensors described elsewhere in this disclosure and in the Related Applications.) The illustrated sensor device 105 is designed to be worn on a patient's wrist and therefore can be used both in clinical settings and in the field (e.g., on any person for whom monitoring might be beneficial, for a variety of reasons, including without limitation assessment of blood pressure and/or hydration during athletic competition or training, daily activities, military training or action, etc.). In one aspect, the sensor device 105 can serve as an integrated hydration monitor, which can assess hydration as described herein, display an indication of the assessment, recommend therapeutic action based on the assessment, or the like, in a form factor that can be worn during athletic events and/or daily activities.

Hence, the exemplary sensor 105 device (hydration monitor) includes a finger cuff 125 and a wrist unit 130. The finger cuff 125 includes a fingertip sensor 135 (in this case, a PPG sensor) that captures data based on physiological conditions of the patient, such as PPG waveform data. The sensor 135 communicates with an input/output unit 140 of the wrist unit 130 to provide output from the sensor 135 to a processing unit 145 of the wrist unit 130. Such communication can be wired (e.g., via a standard—such as USB—or proprietary connector on the wrist unit 130) and/or wireless (e.g., via Bluetooth, such as Bluetooth Low Energy ("BTLE"), near field connection ("NFC"), WiFi, or any other suitable radio technology).

In different embodiments, the processing unit 145 can have different types of functionality. For example, in some cases, the processing unit 145 might simply act to store and/or organize data prior to transmitting the data through the I/O unit 140 to a monitoring computer 100, which might perform data analysis, to control a therapeutic device 115, etc. In other cases, however, the processing unit 145 might act as a specialized computer (e.g., with some or all of the components described in connection with FIG. 9, below and/or some or all of the functionality ascribed to the computer 100 of FIGS. 1A and 1B), such that the processing unit 145 can perform data analysis onboard, e.g., to estimate and/or predict a patient's current and/or future blood pressure. As such, the wrist unit 105 might include a display, which can display any output described herein, including, without limitation, estimated and/or predicted values (e.g., of CRI, blood pressure, hydration status, etc.), data captured by the sensor (e.g., heart rate, pulse ox, etc.), and/or the like.

In some cases, the wrist unit 130 might include a wrist strap 155 that allows the unit to be worn on the wrist, similar to a wrist watch. Of course, other options are available to facilitate transportation of the sensor device 105 with a patent. More generally, the sensor device 105 might not include all of the components described above, and/or various components might be combined and/or reorganized;

once again, the embodiment illustrated by FIG. 1B should be considered only illustrative, and not limiting, in nature.

FIGS. 2A, 2B, 3A, 3B, 4, and 5 illustrate methods and screen displays in accordance with various embodiments. While the methods of FIGS. 2A, 2B, 3A, 3B, 4, and 5 are illustrated, for ease of description, as different methods, it should be appreciated that the various techniques and procedures of these methods can be combined in any suitable fashion, and that, in some embodiments, the methods depicted by FIGS. 2A, 2B, 3A, 3B, 4, and 5 can be considered interoperable and/or as portions of a single method. Similarly, while the techniques and procedures are depicted and/or described in a certain order for purposes of illustration, it should be appreciated that certain procedures may be reordered and/or omitted within the scope of various embodiments. Moreover, while the methods illustrated by FIGS. 2A, 2B, 3A, 3B, 4, and 5 can be implemented by (and, in some cases, are described below with respect to) the computer system 100 of FIG. 1 (or other components of the system, such as the sensor 105 of FIGS. 1A and 1B), these methods may also be implemented using any suitable hardware implementation. Similarly, while the computer system 100 of FIG. 1 (and/or other components of such a system) can operate according to the methods illustrated by FIGS. 2A, 2B, 3A, 3B, 4, and 5 (e.g., by executing instructions embodied on a computer readable medium), the system 100 can also operate according to other modes of operation and/or perform other suitable procedures.

Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

By way of non-limiting example, various embodiments can comprise a method for using sensor data to assess effectiveness of CPR for a patient under cardiac arrest. FIG. 2 illustrates an exemplary method 200 in accordance with various embodiments. The method 200 might comprise generating a model, e.g., with a computer system, against which patient data can be analyzed to estimate and/or predict various physiological states (block 205). In a general sense, generating the model can comprise receiving data pertaining to a plurality of more physiological parameters of a test subject to obtain a plurality of physiological data sets. Such data can include PPG waveform data to name one example, and/or any other type of sensor data including, without limitation, data captured by other sensors described herein and in the Related Applications.

Generating a model can further comprise directly measuring one or more physiological states of the test subject with a reference sensor to obtain a plurality of physiological state measurements. The one or more physiological states can include, without limitation, states of various volumes of blood loss and/or fluid resuscitation, various states of hydration and/or dehydration, and/or various cardiopulmonary states, or the like. (In other embodiments, different states can include a state of hypervolemia, a state of euvolemia, and/or a state of cardiovascular collapse (or near-cardiovascular collapse), and/or can include states that have been simulated, e.g., through use of an LBNP apparatus). Other physiological states that can be used to generate a model are described elsewhere herein and in the Related Applications.

Generating the model can further comprise correlating the physiological state(s) with the measured physiological parameters. There are a variety of techniques for generating a model in accordance with different embodiments, using these general functions. One exemplary technique for generating a model of a generic physiological state is described below with respect to FIG. 4, below, which provides a technique using a machine-learning algorithm to optimize the correlation between measured physiological parameters (such as PPG waveform data, to name one example) and physical states (e.g., various blood volume states, including states where a known volume of blood loss has occurred and/or a known volume of fluid resuscitation has been administered, various states of hydration and/or dehydration, various cardiopulmonary states, etc.). It should be appreciated, however, that any suitable technique or model may be employed in accordance with various embodiments.

A number of physiological states can be modeled, and a number of different conditions can be imposed on test subjects as part of the model generation. For example, physiological states that can be induced (or monitored when naturally occurring) in test subjects include, without limitation, reduced circulatory system volume, known volume of blood loss, specified amounts of fluids added to blood volume, dehydration, cardiovascular collapse or near-cardiovascular collapse, cardiopulmonary collapse or near-cardiopulmonary collapse, euvolemia, hypervolemia, low blood pressure, high blood pressure, normal blood pressure, and/or the like.

Merely by way of example, in one set of embodiments, a number of physiological parameters of a plurality of test subjects might be measured. In some cases, a subject might undergo varying, measured levels of blood loss (either real or simulated) or intravenous fluid addition. Using the method described below with respect to FIG. 4 (or other, similar techniques, many of which are described in the Related Applications), the system can determine which sensor information most effectively differentiates between subjects at different blood loss/addition volume levels.

Additionally and/or alternatively to using direct (e.g., raw) sensor data to build such models, some embodiments might construct a model based on data that is derived from sensor data. Merely by way of example, one such model might use, as input values, CRI values of test subjects in different states of cardiac arrest or different cardiopulmonary states. Accordingly, the process of generating a model might first comprise building a model of CRI, and then, from that model, building a model of CPR effectiveness. (In other cases, a hybrid model might consider both raw sensor data and CRI data.)

A CRI model can be generated in different ways. For example, in some cases, one or more test subjects might be subjected to LBNP. In an exemplary case, LBNP data is collected from human subjects being exposed to progressively lower levels of LBNP, until hemodynamic decompensation, at which time LBNP is released and the subject recovers. Each level of LBNP represents an additional amount of blood loss. During these tests, physiological data (including, without limitation, waveform data, such as continuous non-invasive blood pressure data) can be collected before, during, and/or after the application of the LBNP. As noted above, a relationship (as expressed by Equation 2) can be identified between LBNP and intravascular volume loss, and this relationship can be used to estimate CRI. Hence, LBNP studies form a framework (methodology) for the development of the hemodynamic parameter referred to herein as CRI and can be used to generate models of this parameter.

More generally, several different techniques that induce a physiological state of reduced volume in the circulatory system, e.g., to a point of cardiovascular collapse (hemodynamic decompensation) or to a point near cardiovascular collapse, can be used to generate such a model. LBNP can be used to induce this condition, as noted above. In some cases, such as in a study described below, dehydration can be used to induce this condition as well. Other techniques are possible as well. Similarly, data collected from a subject in a state of euvolemia, dehydration, hypervolemia, and/or other states might be used to generate a CRI model in different embodiments.

At block 210, the method 200 comprises monitoring, with one or more sensors, physiological data of a patient. As noted above, a variety of physical parameters can be monitored, invasively and/or non-invasively, depending on the nature of the anticipated physiological state of the patient. In an aspect, monitoring the one or more physical parameters might comprise receiving, e.g., from a physiological sensor, continuous waveform data, which can be sampled as necessary. Such data can include, without limitation, plethysmograph waveform data, PPG waveform data (such as that generated by a pulse oximeter), and/or the like.

The method 200 might further comprise analyzing, with a computer system (e.g., a monitoring computer 100 and/or a processing unit 135 of a sensor unit, as described above), the physiological data (block 215). In some cases, the physiological data is analyzed against a pre-existing model (which might be generated as described above and which in turn, can be updated based on the analysis, as described in further detail below and in the Related Applications).

Merely by way of example, in some cases, sensor data can be analyzed directly against a generated model to assess the effectiveness of hydration (which can include estimating current values, and/or predicting future values for any or all of $CPR_{eff}$, V, and/or $P_f$, as expressed above. For example, the sensor data can be compared to determine similarities with models that estimate and/or predict any of these values. Merely by way of example, an input waveform captured by a sensor from a patient might be compared with sample waveforms generated by models for each of these values.

For example, the technique 200' provides one method for deriving an estimate of $CPR_{eff}$ in accordance with some embodiments. It should be noted that the technique 200' is presented as an example only, and that while this technique 200' estimates $CPR_{eff}$ from raw sensor data, similar techniques can be used to estimate or predict $CPR_{eff}$, V, and/or $P_f$ from raw sensor data, CRI data, and/or a combination of both. For example, one model might produce a first estimate of $CPR_{eff}$ from raw sensor data, produce a second estimate of $CPR_{eff}$ from estimated CRI values, and then combine those estimates (in either weighted or unweighted fashion) to produce a hybrid $CPR_{eff}$ estimate.

The illustrated technique 200' comprises sampling waveform data (e.g., any of the data described herein and in the Related Applications, including without limitation arterial waveform data, such as continuous PPG waveforms and/or continuous noninvasive blood pressure waveforms) for a specified period, such as 32 heartbeats (block 270). That sample is compared with a plurality of waveforms of reference data corresponding to $CPR_{eff}$ values (block 275), which in this case range from 0 to 100 using the scale described above (but alternatively might use any appropriate scale). These reference waveforms are derived as part of the model developed using the algorithms described in this and the Related Applications, might be the result of experimental data, and/or the like. In effect, these reference waveforms reflect the relationship $f$ from Eq. 6, above.

According to the technique 200', the sample might be compared with waveforms corresponding to a $CPR_{eff}=100$ (block 275a), $CPR_{eff}=50$ (block 275b), and $CPR_{eff}=0$ (block 275c), as illustrated. (As illustrated by the ellipses in FIG. 2B, any number of sample waveforms can be used for the comparison; for example, if there is a nonlinear relationship between the measured sensor data and the $CPR_{eff}$ values, more sample waveforms might provide for a better comparison.) From the comparison, a similarity coefficient is calculated (e.g., using a least squares or similar analysis) to express the similarity between the sampled waveform and each of the reference waveforms (block 280). These similarity coefficients can be normalized (if appropriate) (block 285), and the normalized coefficients can be summed (block 290) to produce an estimated $CPR_{eff}$ value of the patient (block 295).

In other cases, similar techniques can be used to analyze data against a model based on parameters derived from direct sensor measurements. (In one aspect, such operations can be iterative in nature, by generating the derived parameters—such as CRI, to name one example—by analyzing the sensor data against a first model, and then analyzing the derived parameters against a second model.

Figure 3A:
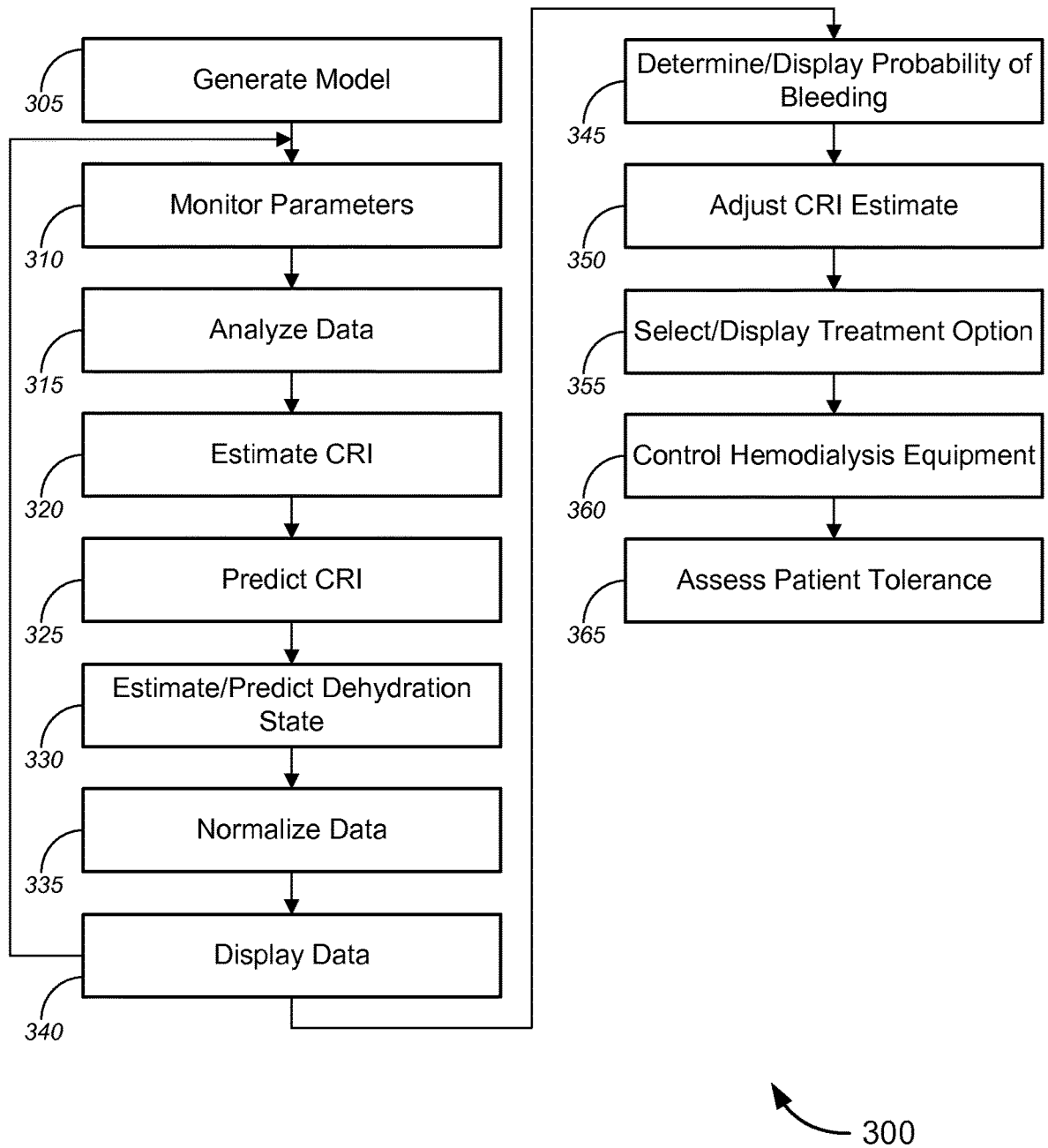
FIG. 3A is a process flow diagram illustrating a method estimating a patient's compensatory reserve and/or dehydration state, in accordance with various embodiments.

For example, FIG. 3A illustrates a method 300 of calculating a patient's CRI, which can be used (in some embodiments) as a parameter that can be analyzed to assess the effectiveness of hydration (including the probability that fluids are needed and/or the estimated volume of fluid necessary for effective hydration) and/or to assess effectiveness of CPR (e.g., before, during, and/or after resuscitation). The method 300 includes generating a model of CRI (block 305), monitoring physiological parameters (310) and analyzing the monitored physical parameters (block 315), using techniques such as those described above and in the '483 application, for example.

Based on this analysis, the method 300, in an exemplary embodiment, includes estimating, with the computer system, a compensatory reserve of the patient, based on analysis of the physiological data (block 320). In some cases, the method might further comprise predicting, with the computer system, the compensatory reserve of the patient at one or more time points in the future, based on analysis of the physiological data (block 325). The operations to predict a future value of a parameter can be similar to those for estimating a current value; in the prediction context, however, the applied model might correlate measured data in a test subject with subsequent values of the diagnostic parameter, rather than contemporaneous values. It is worth noting, of course, that in some embodiments, the same model can be used to both estimate a current value and predict future values of a physiological parameter.

The estimated and/or predicted compensatory reserve of the patient can be based on several factors. Merely by way of example, in some cases, the estimated/predicted compensatory reserve can be based on a fixed time history of monitoring the physiological data of the patient and/or a dynamic time history of monitoring the physiological data of the patient. In other cases, the estimated/predicted compensatory reserve can be based on a baseline estimate of the patient's compensatory reserve established when the patient is euvolemic. In still other cases, the estimate and/or prediction might not be based on a baseline estimate of the patient's compensatory reserve established when the patient is euvolemic.

Figure 3B:
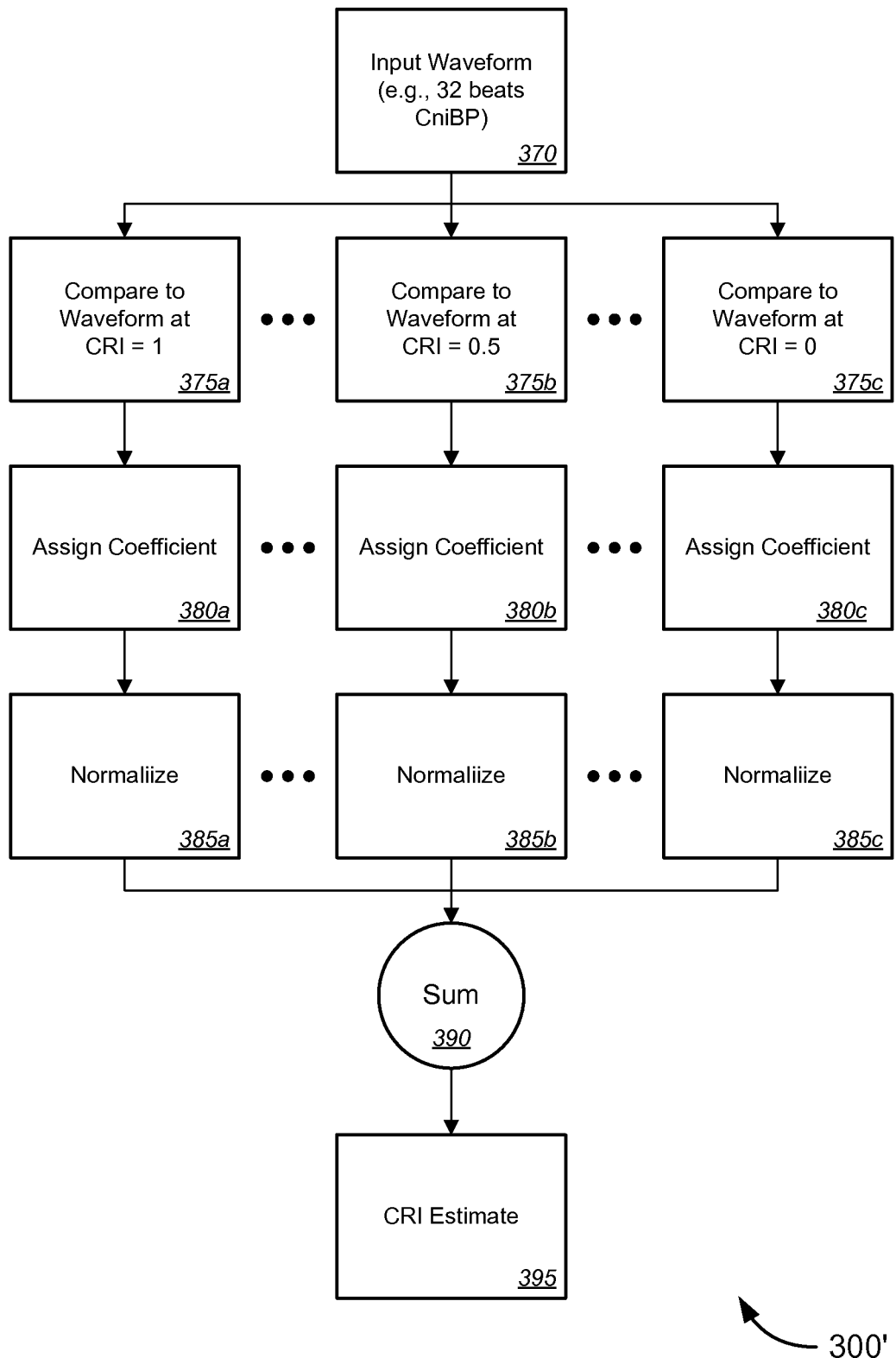
FIG. 3B illustrates a technique for estimating and/or predicting a patient's compensatory reserve index, in accordance with various embodiments.

Merely by way of example, FIG. 3B illustrates one technique 300' for deriving an estimate of CRI in accordance with some embodiments similar to the technique 200' described above with respect to FIG. 2B for deriving an assessment of hydration effectiveness and/or deriving an assessment of CPR effectiveness (e.g., before, during, and/or after resuscitation) directly from sensor data (and, in fact, CRI can be derived as described herein, and that derived value can be used, alone or with raw sensor data, to assess such effectiveness). The illustrated technique comprises sampling waveform data (e.g., any of the data described herein and in the Related Applications, including, without limitation, arterial waveform data, such as continuous PPG waveforms and/or continuous noninvasive blood pressure waveforms) for a specified period, such as 32 heartbeats (block 370). That sample is compared with a plurality of waveforms of reference data corresponding to different CRI values (block 375). (These reference waveforms might be derived using the algorithms described in the Related Applications, might be the result of experimental data, and/or the like). Merely by way of example, the sample might be compared with waveforms corresponding to a CRI of 1 (block 375a), a CRI of 0.5 (block 375b), and a CRI of 0 (block 375c), as illustrated. From the comparison, a similarity coefficient is calculated (e.g., using a least squares or similar analysis) to express the similarity between the sampled waveform and each of the reference waveforms (block 380). These similarity coefficients can be normalized (if appropriate) (block 385), and the normalized coefficients can be summed (block 390) to produce an estimated value of the patient's CRI (block 395).

Returning to FIG. 3A, the method 300 can comprise estimating and/or predicting a patient's dehydration state (block 330). The patient's state of dehydration can be expressed in a number of ways. For instance, the state of dehydration might be expressed as a normalized value (for example, with 1.0 corresponding to a fully hydrated state and 0.0 corresponding to a state of morbid dehydration). In other cases, the state of dehydration might be expressed as a missing volume of fluid or as a volume of fluid present in the patient's system, or using any other appropriate metric.

A number of techniques can be used to model dehydration state. Merely by way of example, as noted above (and described in further detail below), the relationship between a patient's compensatory reserve and level of dehydration can be modeled. Accordingly, in some embodiments, estimating a dehydration state of the patient might comprise estimating the compensatory reserve (e.g., CRI) of the patient, and then, based on that estimate and the known relationship, estimating the dehydration state. Similarly, a predicted value of compensatory reserve at some point in the future can be used to derive a predicted dehydration state at that point in the future. Other techniques might use a parameter other than CRI to model dehydration state.

The method 300 might further comprise normalizing the results of the analysis (block 335), such as the compensatory reserve, dehydration state, probability of bleeding, and/or effectiveness of CPR, to name a few examples. Merely by way of example, the estimated/predicted compensatory reserve of the patient can be normalized relative to a normative normal blood volume value corresponding to euvolemia, a normative excess blood volume value corresponding to circulatory overload, and a normative minimum blood volume value corresponding to cardiovascular collapse. Any values can be selected as the normative values. Merely by way of example, in some embodiments, the normative excess blood volume value is >1, the normative normal blood volume value is 1, and the normative minimum blood volume value is 0. As an alternative, in other embodiments, the normative excess blood volume value might be defined as 1, the normative normal blood volume value might be defined as 0, and the normative minimum blood volume value at the point of cardiovascular collapse might be defined as −1. As can be seen from these examples, different embodiments might use a number of different scales to normalize CRI and other estimated parameters.

In an aspect, normalizing the data can provide benefits in a clinical setting, because it can allow the clinician to quickly make a qualitative judgment of the patient's condition, while interpretation of the raw estimates/predictions might require additional analysis. Merely by way of example, with regard to the estimate of the compensatory reserve of the patient, that estimate might be normalized relative to a normative normal blood volume value corresponding to euvolemia and a normative minimum blood volume value corresponding to cardiovascular collapse. Once again, any values can be selected as the normative values. For example, if the normative normal blood volume is defined as 1, and the normative minimum blood volume value is defined as 0, the normalized value, falling between 0.0 and 1.0 can quickly apprise a clinician of the patient's location on a continuum between euvolemia and cardiovascular collapse. Similar normalizing procedures can be implemented for other estimated data (such as probability of bleeding, dehydration, effectiveness of CPR, and/or the like).

The method 300 might further comprise displaying data with a display device (block 340). Such data might include an estimate and/or prediction of the compensatory reserve of the patient and/or an estimate and/or prediction of the patient's dehydration state. A variety of techniques can be used to display such data. Merely by way of example, in some cases, displaying the estimate of the compensatory reserve of the patient might comprise displaying the normalized estimate of the compensatory reserve of the patient. Alternatively and/or additionally, displaying the normalized estimate of the compensatory reserve of the patient might comprise displaying a graphical plot showing the normalized excess blood volume value, the normalized normal blood volume value, the normalized minimum blood volume value, the normalized estimate of the compensatory reserve (e.g., relative to the normalized excess blood volume value, the normalized normal blood volume value, the normalized minimum blood volume value), and the normalized value indicative of CPR effectiveness.

In some cases, the method 300 might comprise repeating the operations of monitoring physiological data of the patient, analyzing the physiological data, and estimating (and/or predicting) the compensatory reserve of the patient, to produce a new estimated (and/or predicted) compensatory reserve of the patient. Thus, displaying the estimate (and/or prediction) of the compensatory reserve of the patient might comprise updating a display of the estimate of the compensatory reserve to show the new estimate (and/or prediction) of the compensatory reserve, in order to display a plot of the estimated compensatory reserve over time. Hence, the patient's compensatory reserve can be repeatedly estimated and/or predicted on any desired interval (e.g., after every heartbeat), on demand, before fluid resuscitation, during fluid resuscitation, after fluid resuscitation, etc., or a combination of one or more of these.

In further embodiments, the method 300 can comprise determining a probability that the patient is bleeding, and/or displaying, with the display device, an indication of the probability that the patient is bleeding (block 345). For example, some embodiments might generate a model based on data that removes fluid from the circulatory system (such as LBNP, dehydration, etc.). Another embodiment might generate a model based on fluid removed from a subject voluntarily, e.g., during a blood donation, based on the known volume (e.g., 500 cc) of the donation. Based on this model, using techniques similar to those described above, a patient's physiological data can be monitored and analyzed to estimate a probability that the patient is bleeding (e.g., internally). In some cases, bleeding or blood loss (e.g., a state of hypovolemia) may be a contributing factor for cardiac arrest.

In some cases, the probability that the patient is bleeding can be used to adjust the patient's estimated CRI. Specifically, give a probability of bleeding expressed as Pr_Bleed at a time t, the adjusted value of CRI can be expressed as:

$$CRI_{Adjusted}(t)=1-((1-CRI(t))\times Pr\_Bleed(t)) \qquad (Eq.\ 13)$$

Given this relationship, the estimated CRI can be adjusted to produce a more accurate diagnosis of the patient's condition at a given point in time.

The method 300 might comprise selecting, with the computer system, a recommended treatment option for the patient, and/or displaying, with the display device, the recommended treatment option (block 355). The recommended treatment option can be any of a number of treatment options, including, without limitation, optimizing hemodynamics of the patient, a ventilator adjustment, an intravenous fluid adjustment, transfusion of blood or blood products to the patient, infusion of volume expanders to the patient, a change in medication administered to the patient, a change in patient position, and surgical therapy, or the like.

In a specific, non-limiting, example, the method 300 might comprise controlling operation of hemodialysis equipment (block 360), based at least in part on the estimate of the patient's compensatory reserve. Merely by way of example, a computer system that performs the monitoring and estimating functions might also be configured to adjust an ultra-filtration rate of the hemodialysis equipment in response to the estimated CRI values of the patient. In other embodiments, the computer system might provide instructions or suggestions to a human operator of the hemodialysis equipment, such as instructions to manually adjust an ultra-filtration rate, etc.

In some embodiments, the method 300 might include assessing the tolerance of an individual to blood loss, general volume loss, and/or dehydration (block 365). For example, such embodiments might include estimating a patient's CRI based on the change in a patient's position (e.g., from lying prone to standing, from standing to lying prone, from lying prone to sitting, from sitting to lying prone, from standing to sitting, and/or from sitting to standing). Based on changes to the patient's CRI in response to these maneuvers, the patient's sensitivity to blood loss, volume loss, and/or dehydration can be measured. In an aspect, this measurement can be performed using a CRI model generated as described above; the patient can be monitored using one or more of the sensors described above, and the changes in the sensor output when the subject changes position can be analyzed according to the model (as described above, for example) to assess the tolerance of the individual to volume loss. Such monitoring and/or analysis can be performed in real time.

Returning to FIG. 2, based on the analysis of the data (whether data collected directly by sensors or derived data, such as CRI, or both) against a model (which might include multiple sub-models, such as a model of $CPR_{eff}$ against raw data and a model of $CPR_{eff}$ against CRI), the method 200 can include assessing the effectiveness of CPR in resuscitating the patient (block 220), based on analysis of the patient's physiological data against the model. As noted above, assessing the effectiveness of CPR can include estimating or predicting a number of values, such as the estimated effectiveness, $CPR_{eff}$, of the CPR effort, the volume, V, of fluid necessary for effective hydration or cardiopulmonary resuscitation, the probability, $P_f$, that the patient needs fluids, and/or the like.

In some cases, the assessment of the effectiveness of CPR will be based on the analysis of a plurality of measured (or derived) values of a particular physiological parameter (or plurality of parameters). Hence, in some cases, the analysis of the data might be performed on a continuous waveform, either during or after measurement of the waveform with a sensor (or both), and the assessment of the effectiveness of CPR can be updated as resuscitation efforts continue and/or as hydration or other efforts continue. Further, the amount of fluids added to the patient's blood volume can be measured directly, and these direct measurements can be fed back into the model to update the model (at block 225) and thereby improve performance of the algorithms in the model (e.g., by refining the weights given to different parameters in terms of estimative or predictive value). The updated model can then be used to continue assessing the treatment (in the instant patient and/or in a future patient), as shown by the broken lines on FIG. 2A.

Figure 6:
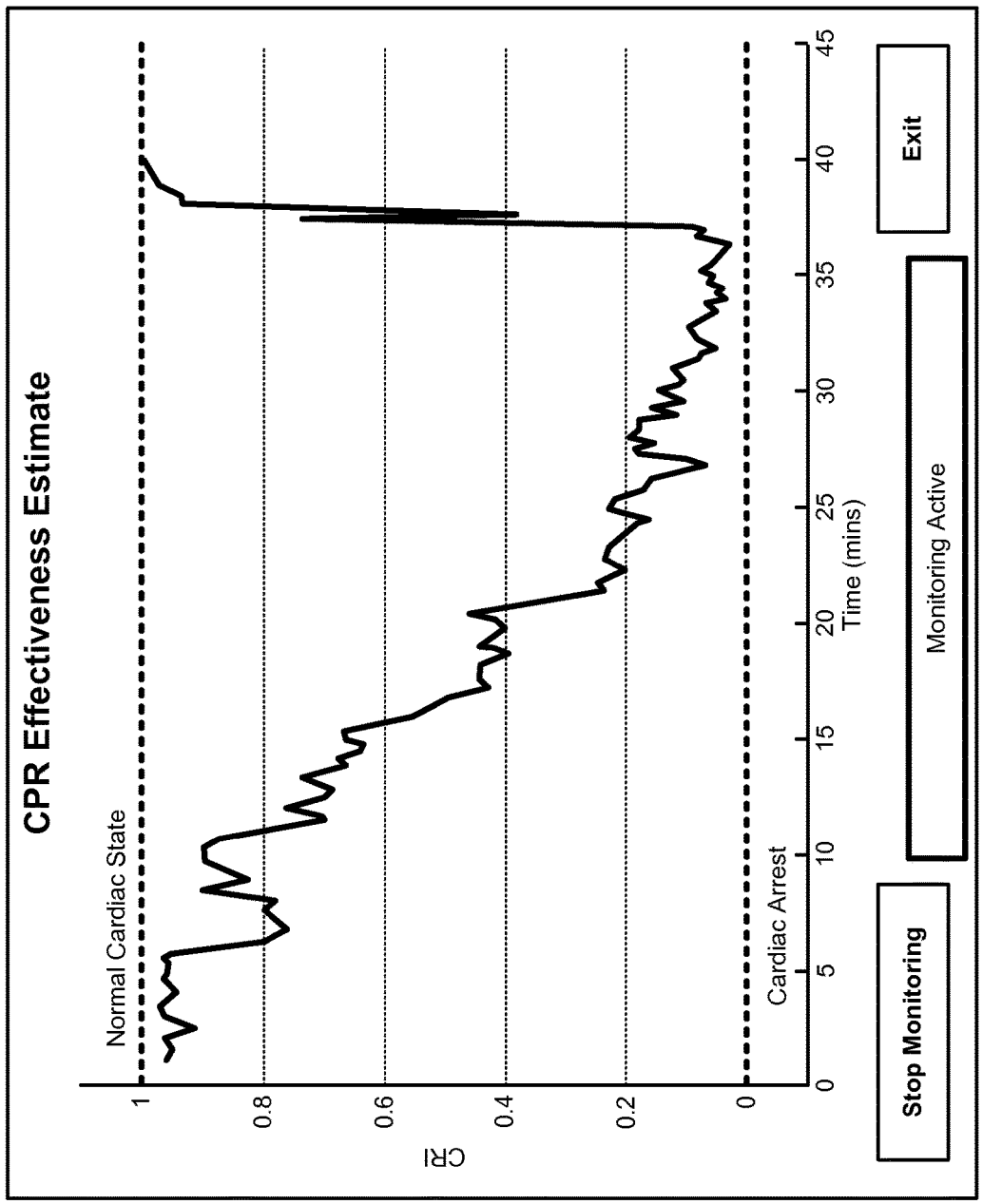
FIGS. 6-8 are exemplary screen captures illustrating display features of a compensatory reserve monitor showing assessments of CPR based on CRI values estimated or obtained before, during, and/or after CPR is performed, in accordance with various techniques.

In some cases, the method 200 comprises displaying data (block 230) indicating the assessment of the effectiveness of CPR. In some cases, the data might be displayed on a display of a sensor device (such as the device 105 illustrated by FIG. 1B). Alternatively and/or additionally the data might be displayed on a dedicated machine, such as a compensatory reserve monitor, or on a monitor of a generic computer system. The data might be displayed alphanumerically, graphically, or both. FIGS. 6-8, described below, illustrate several possible exemplary displays of assessments of the effectiveness of CPR and/or CRI. There are many different ways that the data can be displayed, and any assessments, estimates or predictions generated by the method 200 can be displayed in any desired way, in accordance with various embodiments.

In certain embodiments, the method 200 can include selecting and/or displaying treatment options for the patient (block 235) and/or controlling a therapeutic device (block 240), based on the assessment of the blood loss of the patient. For example, a display might indicate to a clinician or the patient him or herself that the patient is losing (or has lost) blood, that fluid resuscitation therapy should be initiated or continued, an estimated volume of fluid to drink, infuse, or otherwise consume, a drip rate for an IV drip, a flow rate for an IV pump or infuser, that CPR efforts are effectively or ineffectively being performed, or the like. Similarly, the system might be configured to control operation of a therapeutic device, such as dispensing a fluid to drink from an automated dispenser, activating or adjusting the flow rate of an IV pump or infuser, adjusting the drip rate of an IV drip, and/or the like, based, e.g., on the assessment of the effectiveness of hydration, or the like. As another example, certain embodiments might include a water bladder (e.g., a backpack-based hydration pack, such as those available from Camelbak Products LLC) or a water bottle, and the hydration monitor could communicate with and/or control operation of such a dispensing device (e.g., to cause the device to dispense a certain amount of fluid, to cause the device to trigger an audible alarm, etc.).

Further, in certain embodiments, the method 200 can include functionality to help a clinician (or other entity) to monitor hydration, fluid resuscitation, blood volume status, and/or CPR effectiveness. For example, in some cases, any measure of effectiveness outside of the normal range (such as a value of $P_f$ higher than a certain threshold value, a value of $CPR_{\it{eff}}$ lower than a threshold value, etc.) would set off various alarm conditions, such as an audible alarm, a message to a physician, a message to the patient, an update written automatically to a patient's chart, etc. Such messaging could be accomplished by electronic mail, text message, etc., and a sensor device or monitoring computer could be configured with, e.g., an SMTP client, text messaging client, or the like to perform such messaging.

In some cases, feedback and/or notifications might be sent to a third party, regardless of whether any alarm condition were triggered. For example, a hydration monitor might be configured to send monitoring results (e.g., any of the assessments, estimates and/or predictions described herein) to another device or computer, either for personal monitoring by the patient or for monitoring by another. Examples could include transmitting such alarms or data (e.g., by Bluetooth, NFC, WiFi, etc.) to a wireless phone, wearable device (e.g., smart watch or glasses) or other personal device of the patient, e.g., for inclusion in a health monitoring application. Additionally and/or alternatively, such information could be sent to a specified device or computer (e.g., via any available IP connection), for example to allow a parent to monitor a child's (or a child to monitor an elderly parent's) hydration remotely, to allow a coach to monitor a player's hydration remotely, and/or to allow a superior officer to monitor a soldier's hydration remotely, or the like. In some cases (e.g., for a coach or superior officer), an application might aggregate results from a plurality of hydration monitors, to allow the supervisor to view (e.g., in a dashboard-type configuration), hydration effectiveness and/or blood loss (and/or any other data, such as CRI, blood pressure, etc.) for a group of people. Such a display might employ, for example, a plurality of "fuel gauge" displays, one (or more) for each person in the group, allowing the supervisor to quickly ascertain any unusual results (e.g., based on the color of the gauge, etc.).

Similarly, if an alarm condition were met for another physiological parameter (such as blood pressure, which can be estimated as described in the '171 application, for example), that alarm could trigger an assessment of hydration effectiveness via the method 200, to determine whether the first alarm condition has merit or not. If not, perhaps there could be an automated silencing of the original alarm condition, since all is well at present. More generally, the assessment techniques could be added to an ecosystem of monitoring algorithms (including, without limitation, those described in the Related Applications), which would inform one another or work in combination, to inform one another about how to maintain optimal physiological stability.

Figure 4:
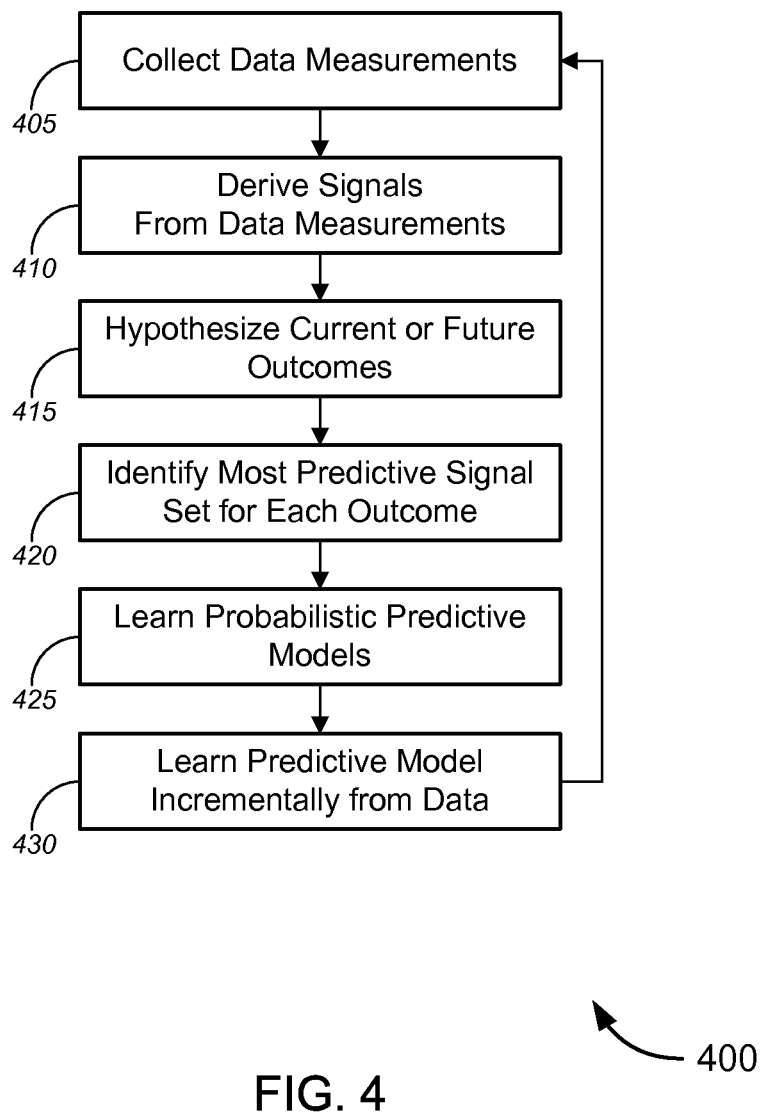
FIG. 4 is a process flow diagram illustrating a method of generating a model of a physiological state, in accordance with various embodiments.

FIG. 4 illustrates a method 400 of employing such a self-learning predictive model (or machine learning) technique, according to some embodiments. In particular, the method 400 can be used to correlate physiological data received from a subject sensor with a measured physiological state. More specifically, with regard to various embodiments, the method 400 can be used to generate a model for assessing, predicting and/or estimating various physiological parameters, such as blood loss volume, effectiveness of hydration or fluid resuscitation efforts, estimated and/or predicted blood pressure, CRI, the probability that a patient is bleeding, a patient's dehydration state, effectiveness of CPR, and/or the like, from one or more of a number of different physiological parameters, including without limitation those described above and in the Related Applications.

The method 400 begins at block 405 by collecting raw data measurements that may be used to derive a set of D data signals $s_1, \ldots, s_D$ as indicated at block 410 (each of the data signals s being, in a particular case, input from one or many different physiological sensors). Embodiments are not constrained by the type of measurements that are made at block 405 and may generally operate on any data set. For example, data signals can be retrieved from a computer memory and/or can be provided from a sensor or other input device. As a specific example, the data signals might correspond to the output of the sensors described above (which measure the types of waveform data described above, such as continuous, non-invasive PPG data and/or blood pressure waveform data).

A set of K current or future outcomes $\vec{o}=(o_1, \ldots, o_K)$ is hypothesized at block 415 (the outcomes o being, in this case, past and/or future physiological states, such as probability that fluids are needed, volume of fluid needed for effective CPR, $CPR_{\it{eff}}$, CRI, dehydration state, probability of bleeding, etc.). The method autonomously generates a predictive model M that relates the derived data signals $\vec{s}$ with the outcomes $\vec{o}$. As used herein, "autonomous" means "without human intervention."

As indicated at block 420, this is achieved by identifying the most predictive set of signals $S_k$, where $S_k$ contains at least some (and perhaps all) of the derived signals $s_1, \ldots, s_D$ for each outcome $o_k$, where $k \in \{1, \ldots, K\}$. A probabilistic predictive model $\hat{o}_k = M_k(S_k)$ is learned at block 425, where $\hat{o}_k$ is the prediction of outcome $o_k$ derived from the model $M_k$ that uses as inputs values obtained from the set of signals $S_k$, for all $k \in \{1, \ldots, K\}$. The method 400 can learn the predictive models $\hat{o}_k = M_k(S_k)$ incrementally (block 430) from data that contains example values of signals $s_1, \ldots, s_D$ and the corresponding outcomes $o_1, \ldots, o_K$. As the data become available, the method 400 loops so that the data are added incrementally to the model for the same or different sets of signals $S_k$, for all $k \in \{1, \ldots, K\}$.

While the description above outlines the general characteristics of the methods, additional features are noted. A linear model framework may be used to identify predictive variables for each new increment of data. In a specific embodiment, given a finite set of data of signals and outcomes $\{(\vec{s}_1, \vec{o}_1), (\vec{s}_2, \vec{o}_2), \ldots\}$, a linear model may be constructed that has the form, for all $k \in \{1, \ldots, K\}$, $$\hat{o}_k = f_k(a_0 + \Sigma_{i=1}^{d} a_i s_i) \qquad (\text{Eq. 14})$$

where $f_k$ is any mapping from one input to one output, and $a_0, a_1, \ldots, a_d$ are the linear model coefficients. The framework used to derive the linear model coefficients may estimate which signals $s, s_1, \ldots, s_d$ are not predictive and accordingly sets the corresponding coefficients $a_0, a_1, \ldots, a_d$ to zero. Using only the predictive variables, the model builds a predictive density model of the data, $\{(\vec{s}_1, \vec{o}_1), (\vec{s}_2, \vec{o}_2), \ldots\}$. For each new increment of data, a new predictive density models can be constructed.

In some embodiments, a prediction system can be implemented that can predict future results from previously analyzed data using a predictive model and/or modify the predictive model when data does not fit the predictive model. In some embodiments, the prediction system can make predictions and/or to adapt the predictive model in real-time. Moreover, in some embodiments, a prediction system can use large data sets not only to create the predictive model, but also predict future results as well as adapt the predictive model.

In some embodiments, a self-learning, prediction device can include a data input, a processor, and an output. Memory can include application software that when executed can direct the processor to make a prediction from input data based on a predictive model. Any type of predictive model can be used that operates on any type of data. In some embodiments, the predictive model can be implemented for a specific type of data. In some embodiments, when data is received the predictive model can determine whether it understands the data according to the predictive model. If the data is understood, a prediction is made and the appropriate output provided based on the predictive model. If the data is not understood when received, then the data can be added to the predictive model to modify the model. In some embodiments, the device can wait to determine the result of the specified data and can then modify the predictive model accordingly. In some embodiments, if the data is understood by the predictive model and the output generated using the predictive model is not accurate, then the data and the outcome can be used to modify the predictive model. In some embodiments, modification of the predictive model can occur in real-time.

Particular embodiments can employ the tools and techniques described in the Related Applications in accordance with the methodology described herein perform the functions of a cardiac reserve monitor, a wrist-wearable sensor device, and/or a monitoring computer, as described herein (the functionality of any or all of which can be combined in a single, integrated device, in some embodiments). These functions include, but are not limited to, assessing fluid resuscitation of a patient, assessing hydration of a patient, monitoring, estimating and/or predicting a subject's (including, without limitation, a patient's) current or future blood pressure and/or compensatory reserve, estimating and/or determining the probability that a patient is bleeding (e.g., internally) and/or has been bleeding, determining effectiveness of CPR, recommending treatment options for such conditions, and/or the like. Such tools and techniques include, in particular, the systems (e.g., computer systems, sensors, therapeutic devices, etc.) described in the Related Applications, the methods (e.g., the analytical methods for generating and/or employing analytical models, the diagnostic methods, etc.), and the software programs described herein and in the Related Applications, which are incorporated herein by reference.

Figure 5:
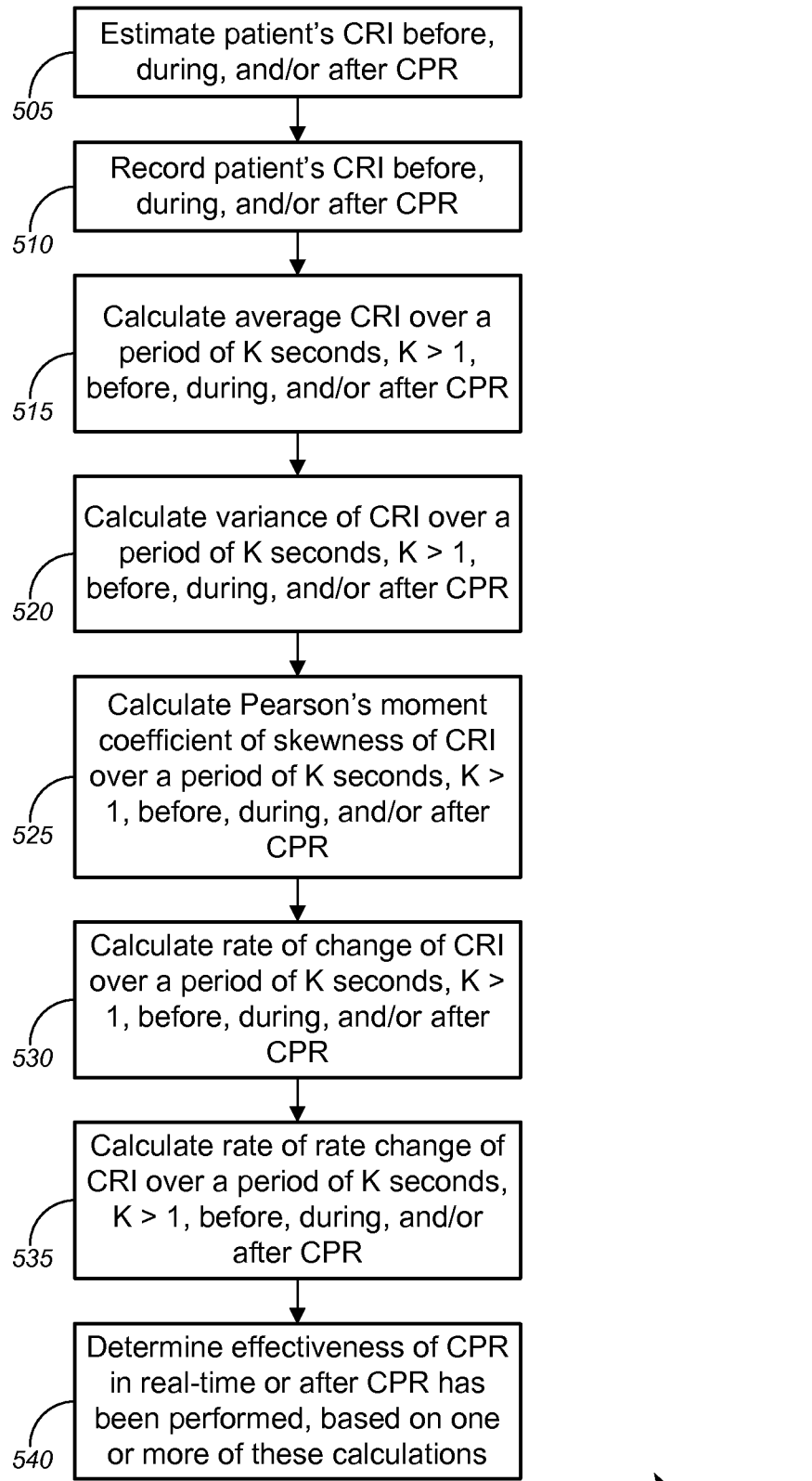
FIG. 5 is a process flow diagram illustrating a method of implementing estimation of CRI values before, during, and after CPR is performed, in accordance with various embodiments.

FIG. 5 illustrates a method 500 of implementing estimation of CRI values before, during, and after CPR is performed, in accordance with various embodiments. In the embodiment of FIG. 5, method 500, at block 505, comprises estimating a patient's CRI before, during, and/or after resuscitation (e.g., CPR, or the like). Estimation of the patient's CRI may be performed, for example, using the techniques described above with respect to FIGS. 3A and 3B, or using other techniques described above.

At block 510, method 500 might comprise recording the patient's CRI, before, during, and/or after CPR is performed. In some instances, the CRI may be recorded or stored on one or more of a data storage device that is part of processing unit 145 and/or a memory device that is part of the monitoring computer 100 of FIG. 1, or the like. Method 500 might further comprise calculating an average CRI over a period of K seconds (where K>1), before, during, and/or after CPR is performed (block 515), calculating a standard deviation or variance of CRI over a period of K seconds (where K>1), before, during, and/or after CPR is performed (block 520), calculating Pearson's moment coefficient of skewness of CRI over a period of K seconds (where K>1), before, during, and/or after CPR is performed (block 525), calculating a rate of change of CRI over a period of K seconds (where K>1), before, during, and/or after CPR is performed (block 530), calculating a rate of rate change of CRI (also referred to herein as "acceleration of CRI") over a period of K seconds (where K>1), before, during, and/or after CPR is performed (block 535).

According to some embodiments, method 500 might further comprise, at block 540, determining effectiveness of CPR in real-time or after CPR has been performed, based on one or more of the calculations in blocks 515-535 (which may be referred to herein as "CRI variation results"). In other words, the CRI variation results might be used to assess effectiveness of the CPR. For example, one embodiment might provide feedback in the form of a classification (such as "very good," "good," or "poor") of the effectiveness of CPR. Other embodiments might provide feedback indicating a number within a range (e.g., between 0 to 100) indicating the effectiveness of the CPR.

In some embodiments, the following definitions might be used for (i) CRI value sample, (ii) a set of values of CRI, (iii) average CRI, (iv) median CRI, (v) standard deviation of CRI, (vi) rate of change of CRI, (vii) rate of change of rate change of CRI, and (viii) skewness of CRI:

(i) A specific CRI value at time t:

$$\text{CRI}(t); \tag{Eq. 15}$$

(ii) A set of CRI values at times $\{t_1, t_2, \ldots, t_K\}$:

$$\text{CRI}=\{\text{CRI}(t_1), \text{CRI}(t_2), \ldots, \text{CRI}(t_K)\}; \tag{Eq. 16}$$

(iii) Average CRI value over a specific set of times $\{t_1, t_2, \ldots, t_K\}$:

$$\overline{\text{CRI}}_K = \Sigma_{k=1}^{K} \text{CRI}(t_k); \tag{Eq. 17}$$

(iv) Median CRI value over a specific set of times $\{t_1, t_2, \ldots, t_K\}$:

$$\text{CRI}_K^{Med} = \text{Median}\{\text{CRI}(t_1), \text{CRI}(t_2), \ldots, \text{CRI}(t_K)\}; \tag{Eq. 18}$$

(v) A measure of deviation of CRI over a specific set of times $\{t_1, t_2, \ldots, t_K\}$, perhaps variance, or standard deviation defined by:

$$SD(\text{CRI}_K) = \sqrt{\frac{\sum_{k=1}^{K}(\text{CRI}(t_k) - \overline{\text{CRI}}_K)^2}{K}}; \tag{Eq. 19}$$

(vi) Rate of change of CRI, denoted by $m_K$, over a set of CRI values $\{\text{CRI}(t_1), \text{CRI}(t_2), \ldots, \text{CRI}(t_K)\}$, where the rate of change measures some increase or decrease of CRI over a specific period of time, and, for example, may be calculated as a slope of the line:

$$\begin{bmatrix} m_K \\ b \end{bmatrix} = (A^t A)^{-1} A^t \begin{bmatrix} \text{CRI}(t_1) \\ \vdots \\ \text{CRI}(t_K) \end{bmatrix}, \tag{Eq. 20}$$

where A is a matrix defined by:

$$A = \begin{bmatrix} t_1 & 1 \\ \vdots & \vdots \\ t_K & 1 \end{bmatrix};$$ (Eq. 21)

(vii) Rate of change of rate change of CRI, denoted by $r_K$, over a set of CRI values $\{CRI(t_1), CRI(t_2), \ldots, CRI(t_K)\}$, where the rate of change of rate change measures some rate of change of increase or decrease of CRI over a specific period of time, and, for example, may be calculated as a second order increase or decrease of a curve:

$$\begin{bmatrix} r_K \\ m_K \\ b \end{bmatrix} = (B^t B)^{-1} B^t \begin{bmatrix} CRI(t_1) \\ \vdots \\ CRI(t_K) \end{bmatrix},$$ (Eq. 22)

where B is a matrix defined by:

$$B = \begin{bmatrix} (t_1)^2 & t_1 & 1 \\ \vdots & \vdots & \vdots \\ (t_K)^2 & t_K & 1 \end{bmatrix};$$ (Eq. 23)

(viii) Some measure of skewness, denoted by $S_K$, over a set of CRI values $\{CRI(t_1), CRI(t_2), \ldots, CRI(t_K)\}$, where $S_K$ is possibly a variant of the Fisher-Pearson coefficient of skewness:

$$S_K = \frac{1}{(SD(CRI_K))^3} \left[ \frac{\sum_{k=1}^{K} (CRI(t_k) - \overline{CRI}_K)^3}{K} \right],$$ (Eq. 24)

and/or $S_K$ is some other measure of skewness, possibly Galton skewness (or Bowley's skewness), as defined as:

$$S_K = \frac{Q_1 + Q_3 - 2Q_2}{Q_3 - Q_1}.$$ (Eq. 25)

A method for assessing whether CPR being performed or that was performed can be classified as "very good" or "good" might include, but is not limited to, one of the following calculations or a combination of two or more such calculations, perhaps within a statistical and/or machine learning framework, or the like: (1) Average of CRI during CPR ("$\overline{CRI}_{DR}$")>CPRG1; (2) Average of CRI after CPR ("$\overline{CRI}_{AR}$")>CPRG2; (3) standard deviation or variance of CRI during CPR ("$[SD(CRI)]_{DR}$")<CPRG3; (4) standard deviation or variance of CRI after CPR ("$[SD(CRI)]_{AR}$")<CPRG4; (5) moment coefficient of skewness of CRI (positive or negative) during CPR ("$S_{DR}$")<CPRG5; (6) moment coefficient of skewness of CRI (positive or negative) after CPR ("$S_{AR}$")<CPRG6; (7) rate of change of CRI during CPR ("$m_{DR}$")>CPRG7; (8) rate of change of CRI after CPR ("$m_{AR}$")>CPRG8; (9) rate of rate change of CRI during CPR ("$r_{DR}$")>CPRG9; (10) rate of rate change of CRI after CPR ("$r_{AR}$")>CPRG10; and/or the like. In some cases, each of, or one or more of, CPRG1 through CPRG10 might either be estimated experimentally or set by the user. Herein, the number K>0 may be different in each instance of the calculations (1) through (10), may be chosen by the user, or may be experimentally determined.

With reference to (1) the average CRI during CPR, $CRI_{DR} = \{CRI(t_1), CRI(t_2), \ldots, CRI(t_K)\}$ may be any set of points sampled at times during CPR, and $\overline{CRI}_{DR}$ may be the average value of those points. Accordingly, a classification of good or very good CPR may be made by choosing a threshold, either experimentally or user set, denoted by $^G\overline{CRI}_{DR}$ (e.g., CPRG1 above), and classifying good or very good CPR may be determined if:

$$\overline{CRI}_{DR} > {}^G\overline{CRI}_{DR}.$$ (Eq. 26)

Referring to (2) the average CRI after CPR, $CRI_{AR} = \{CRI(t_1), CRI(t_2), \ldots, CRI(t_K)\}$ may be any set of points sampled at times after CPR, and $\overline{CRI}_{AR}$ may be the average value of those points. Accordingly, a classification of good or very good CPR may be made by choosing a threshold, either experimentally or user set, denoted by $^G\overline{CRI}_{AR}$ (e.g., CPRG2 above), and classifying good or very good CPR may be determined if:

$$\overline{CRI}_{AR} > {}^G\overline{CRI}_{AR}.$$ (Eq. 27)

With reference to (3) the variance of CRI during CPR, $CRI_{DR} = \{CRI(t_1), CRI(t_2), \ldots, CRI(t_K)\}$ may be any set of points sampled at times during CPR, and $[SD(CRI)]_{DR}$ may be the variation of those values (perhaps the standard deviation as defined above). Accordingly, a classification of good or very good CPR may be made by choosing a threshold, either experimentally or user set, denoted by $^G[SD(CRI)]_{DR}$ (e.g., CPRG3 above), and classifying good or very good CPR may be determined if:

$$[SD(CRI)]_{DR} < {}^G[SD(CRI)]_{DR}.$$ (Eq. 28)

Referring to (4) the variance of CRI after CPR, $CRI_{AR} = \{CRI(t_1), CRI(t_2), \ldots, CRI(t_K)\}$ may be any set of points sampled at times after CPR, and $[SD(CRI)]_{AR}$ may be the variation of those values (perhaps the standard deviation as defined above). Accordingly, a classification of good or very good CPR may be made by choosing a threshold, either experimentally or user set, denoted by $^G[SD(CRI)]_{AR}$ (e.g., CPRG4 above), and classifying good or very good CPR may be determined if:

$$[SD(CRI)]_{AR} < {}^G[SD(CRI)]_{AR}.$$ (Eq. 29)

With reference to (5) the skewness of CRI during CPR, $CRI_{DR} = \{CRI(t_1), CRI(t_2), \ldots, CRI(t_K)\}$ may be any set of points sampled at times during CPR, and $S_{DR}$ may be a measure of skewness of those points (perhaps as defined above). Accordingly, a classification of good or very good CPR may be made by choosing a threshold, either experimentally or user set, denoted by $^GS_{DR}$ (e.g., CPRG5 above), and classifying good or very good CPR may be determined if:

$$|S_{DR}| < {}^GS_{DR}.$$ (Eq. 30)

Referring to (6) the skewness of CRI after CPR, $CRI_{AR} = \{CRI(t_1), CRI(t_2), \ldots, CRI(t_K)\}$ may be any set of points sampled at times after CPR, and $S_{AR}$ may be a measure of skewness of those points (perhaps as defined above). Accordingly, a classification of good or very good CPR may be made by choosing a threshold, either experimentally or user set, denoted by $^GS_{AR}$ (e.g., CPRG6 above), and classifying good or very good CPR may be determined if:

$$|S_{AR}| < {}^GS_{AR}.$$ (Eq. 31)

With reference to (7) the rate of change of CRI during CPR, $CRI_{DR}=\{CRI(t_1), CRI(t_2), \ldots, CRI(t_K)\}$ may be any set of points sampled at times during CPR, and $m_{DR}$ may be a measure of rate of change of those points (perhaps as defined above). Accordingly, a classification of good or very good CPR may be made by choosing a threshold, either experimentally or user set, denoted by $^G m_{DR}$ (e.g., CPRG7 above), and classifying good or very good CPR may be determined if:

$$m_{DR} > ^G m_{DR}. \qquad (Eq.\ 32)$$

Referring to (8) the rate of change of CRI after CPR, $CRI_{AR}=\{CRI(t_1), CRI(t_2), \ldots, CRI(t_K)\}$ may be any set of points sampled at times after CPR, and $m_{AR}$ may be a measure of rate of change of those points (perhaps as defined above). Accordingly, a classification of good or very good CPR may be made by choosing a threshold, either experimentally or user set, denoted by $^G m_{AR}$ (e.g., CPRG8 above), and classifying good or very good CPR may be determined if:

$$m_{AR} > ^G m_{AR}. \qquad (Eq.\ 33)$$

With reference to (9) the rate of rate change of CRI during CPR, $CRI_{DR}=\{CRI(t_1), CRI(t_2), \ldots, CRI(t_K)\}$ may be any set of points sampled at times during CPR, and $r_{DR}$ may be a measure of rate of rate change of those points (perhaps as defined above). Accordingly, a classification of good or very good CPR may be made by choosing a threshold, either experimentally or user set, denoted by $^G r_{DR}$ (e.g., CPRG9 above), and classifying good or very good CPR may be determined if:

$$r_{DR} > ^G r_{DR}. \qquad (Eq.\ 34)$$

Referring to (10) the rate of rate change of CRI after CPR, $CRI_{AR}=\{CRI(t_1), CRI(t_2), \ldots, CRI(t_K)\}$ may be any set of points sampled at times after CPR, and $r_{AR}$ may be a measure of rate of rate change of those points (perhaps as defined above). Accordingly, a classification of good or very good CPR may be made by choosing a threshold, either experimentally or user set, denoted by $^G r_{AR}$ (e.g., CPRG10 above), and classifying good or very good CPR may be determined if:

$$r_{AR} > ^G r_{AR}. \qquad (Eq.\ 35)$$

Similarly, in some instances, a method for assessing whether CPR being performed or that was performed can be classified as "poor" or "bad" might include, but is not limited to, one of the following calculations or a combination of two or more such calculations, perhaps within a statistical and/or machine learning framework, or the like: (1) Average of CRI during CPR ("$\overline{CRI}_{DR}$")<CPRB1; (2) Average of CRI after CPR ("$\overline{CRI}_{AR}$")<CPRB2; (3) standard deviation or variance of CRI during CPR ("$[SD(CRI)]_{DR}$")>CPRB3; (4) standard deviation or variance of CRI after CPR ("$[SD(CRI)]_{AR}$")>CPRB4; (5) moment coefficient of skewness of CRI (positive or negative) during CPR ("$S_{DR}$")>CPRB5; (6) moment coefficient of skewness of CRI (positive or negative) after CPR ("$S_{AR}$")>CPRB6; (7) rate of change of CRI during CPR ("$m_{DR}$")<CPRB7; (8) rate of change of CRI after CPR ("$m_{AR}$")<CPRB8; (9) rate of rate change of CRI during CPR ("$r_{DR}$")<CPRB9; (10) rate of rate change of CRI after CPR ("$r_{AR}$")<CPRB10; and/or the like. In some cases, each of, or one or more of, CPRB1 through CPRB10 might either be estimated experimentally or set by the user. Herein, the number K>0 may be different in each instance of the calculations (1) through (10), may be chosen by the user, or may be experimentally determined.

With reference to (1) the average CRI during CPR, $CRI_{DR}=\{CRI(t_1), CRI(t_2), \ldots, CRI(t_K)\}$ may be any set of points sampled at times during CPR, and $\overline{CRI}_{DR}$ may be the average value of those points. Accordingly, a classification of poor or bad CPR may be made by choosing a threshold, either experimentally or user set, denoted by $^B \overline{CRI}_{DR}$ (e.g., CPRB1 above), and classifying poor or bad CPR may be determined if:

$$\overline{CRI}_{DR} < ^B \overline{CRI}_{DR}. \qquad (Eq.\ 36)$$

Referring to (2) the average CRI after CPR, $CRI_{AR}=\{CRI(t_1), CRI(t_2), \ldots, CRI(t_K)\}$ may be any set of points sampled at times after CPR, and $\overline{CRI}_{AR}$ may be the average value of those points. Accordingly, a classification of poor or bad CPR may be made by choosing a threshold, either experimentally or user set, denoted by $^B \overline{CRI}_{AR}$ (e.g., CPRB2 above), and classifying poor or bad CPR may be determined if:

$$\overline{CRI}_{AR} < ^B \overline{CRI}_{AR}. \qquad (Eq.\ 37)$$

With reference to (3) the variance of CRI during CPR, $CRI_{DR}=\{CRI(t_1), CRI(t_2), \ldots, CRI(t_K)\}$ may be any set of points sampled at times during CPR, and $[SD(CRI)]_{DR}$ may be the variation of those values (perhaps the standard deviation as defined above). Accordingly, a classification of poor or bad CPR may be made by choosing a threshold, either experimentally or user set, denoted by $^B[SD(CRI)]_{DR}$ (e.g., CPRB3 above), and classifying poor or bad CPR may be determined if:

$$[SD(CRI)]_{DR} > ^B[SD(CRI)]_{DR}. \qquad (Eq.\ 38)$$

Referring to (4) the variance of CRI after CPR, $CRI_{AR}=\{CRI(t_1), CRI(t_2), \ldots, CRI(t_K)\}$ may be any set of points sampled at times after CPR, and $[SD(CRI)]_{AR}$ may be the variation of those values (perhaps the standard deviation as defined above). Accordingly, a classification of poor or bad CPR may be made by choosing a threshold, either experimentally or user set, denoted by $^B[SD(CRI)]_{AR}$ (e.g., CPRB4 above), and classifying poor or bad CPR may be determined if:

$$[SD(CRI)]_{AR} > ^B[SD(CRI)]_{AR}. \qquad (Eq.\ 39)$$

With reference to (5) the skewness of CRI during CPR, $CRI_{DR}=\{CRI(t_1), CRI(t_2), \ldots, CRI(t_K)\}$ may be any set of points sampled at times during CPR, and $S_{DR}$ may be a measure of skewness of those points (perhaps as defined above). Accordingly, a classification of poor or bad CPR may be made by choosing a threshold, either experimentally or user set, denoted by $^B S_{DR}$ (e.g., CPRB5 above), and classifying poor or bad CPR may be determined if:

$$|S_{DR}| > ^B S_{DR}. \qquad (Eq.\ 40)$$

Referring to (6) the skewness of CRI after CPR, $CRI_{AR}=\{CRI(t_1), CRI(t_2), \ldots, CRI(t_K)\}$ may be any set of points sampled at times after CPR, and $S_{AR}$ may be a measure of skewness of those points (perhaps as defined above). Accordingly, a classification of poor or bad CPR may be made by choosing a threshold, either experimentally or user set, denoted by $^B S_{AR}$ (e.g., CPRB6 above), and classifying poor or bad CPR may be determined if:

$$|S_{AR}| > ^B S_{AR}. \qquad (Eq.\ 41)$$

With reference to (7) the rate of change of CRI during CPR, $CRI_{DR}=\{CRI(t_1), CRI(t_2), \ldots, CRI(t_K)\}$ may be any set of points sampled at times during CPR, and $m_{DR}$ may be a measure of rate of change of those points (perhaps as defined above). Accordingly, a classification of poor or bad CPR may be made by choosing a threshold, either experimentally or user set, denoted by $^B m_{DR}$ (e.g., CPRB7 above), and classifying poor or bad CPR may be determined if:

$$m_{DR} < {}^B m_{DR}. \tag{Eq. 42}$$

Referring to (8) the rate of change of CRI after CPR, $CRI_{AR} = \{CRI(t_1), CRI(t_2), \ldots, CRI(t_K)\}$ may be any set of points sampled at times after CPR, and $m_{AR}$ may be a measure of rate of change of those points (perhaps as defined above). Accordingly, a classification of poor or bad CPR may be made by choosing a threshold, either experimentally or user set, denoted by $^B m_{AR}$ (e.g., CPRB8 above), and classifying poor or bad CPR may be determined if:

$$m_{AR} < {}^B m_{AR}. \tag{Eq. 43}$$

With reference to (9) the rate of rate change of CRI during CPR, $CRI_{DR} = \{CRI(t_1), CRI(t_2), \ldots, CRI(t_K)\}$ may be any set of points sampled at times during CPR, and $r_{DR}$ may be a measure of rate of rate change of those points (perhaps as defined above). Accordingly, a classification of poor or bad CPR may be made by choosing a threshold, either experimentally or user set, denoted by $^B r_{DR}$ (e.g., CPRB9 above), and classifying poor or bad CPR may be determined if:

$$r_{DR} < {}^B r_{DR}. \tag{Eq. 44}$$

Referring to (10) the rate of rate change of CRI after CPR, $CRI_{AR} = \{CRI(t_1), CRI(t_2), \ldots, CRI(t_K)\}$ may be any set of points sampled at times after CPR, and $r_{AR}$ may be a measure of rate of rate change of those points (perhaps as defined above). Accordingly, a classification of poor or bad CPR may be made by choosing a threshold, either experimentally or user set, denoted by $^B r_{AR}$ (e.g., CPRB10 above), and classifying poor or bad CPR may be determined if:

$$r_{AR} < {}^B r_{AR}. \tag{Eq. 45}$$

Likewise, in some instances, a method for estimating a value within a range (e.g., 0 to 100) that corresponds to a spectrum or continuum between worse and better CPR effectiveness (e.g., with lower values indicating worse CPR effectiveness and higher values indicating better CPR effectiveness) might include, but is not limited to, one of the above calculations or a combination of two or more such calculations, perhaps within a statistical and/or machine learning framework, or the like, to estimate the value corresponding to level of effectiveness of CPR. In some cases, the method might include, without limitation, empirical estimations of probability density functions, cumulative distribution functions using graphical and/or nonparametric models, and/or the like. Other methods might include, but are not limited to: (i) probability of effective CPR being proportional to the number of times the good or very good CPR threshold is achieved; (ii) probability of effective CPR being proportional to the number of times the poor CPR threshold is achieved; (iii) probability of effective CPR being proportional to the number of times the good or very good CPR threshold is achieved minus the number of times the poor CPR threshold is achieved; (iv) probability of effective CPR being expressed as $$Pr(CPR_{eff}) = f(\overline{CRI}_{DR}, \overline{CRI}_{AR}, [SD(CRI)]_{DR}, [SD(CRI)]_{AR}, S_{DR}, S_{AR}, m_{DR}, m_{AR}, r_{DR}, r_{AR}), \tag{Eq. 46}$$

In some embodiments, estimated CRI values might include, but are not limited to, one or more of CRI values estimated or measured after every heartbeat, CRI values averaged over the preceding or last N seconds (where N>1), and/or the median value of CRI over the preceding or last N seconds (where N>1), or the like. According to some embodiments, the calculations described above with respect to blocks 515-535 might utilize these estimated CRI values.

According to some embodiments, instead of using CRI measurements, a method might use all or some of the calculations above that replace CRI values with values corresponding to measurements related to any measure of compensatory reserve, or derivative thereof, using one or more of the sensor types described above.

FIGS. 6-8 illustrate exemplary screen captures from a display device of a compensatory reserve monitor, showing various features that can be provided by one or more embodiments. Similar screens could be shown by other monitoring devices, such as a display of a wrist-wearable sensor device, a display of a monitoring computer, and/or the like. While FIGS. 6-8 use $CPR_{eff}$ or CRI as an example condition for illustrative purposes, other embodiments might also display values for the volume, V, the volume of fluid necessary for effective hydration, or the probability, $P_f$, that the patient needs fluid (including additional fluid, if hydration efforts already are underway).

FIG. 6 illustrates an exemplary display 600 of a compensatory reserve monitor implementation where a normalized CRI estimate of "1" implies that normal cardiac state of the patient is reached and that CPR is certainly effective, and "0" implies that cardiac arrest is severe and that CPR up to this point has certainly not been effective. Values in between "0" and "1" imply a continuum of (relative, or higher/lower) effectiveness of CPR.

Figure 7A:
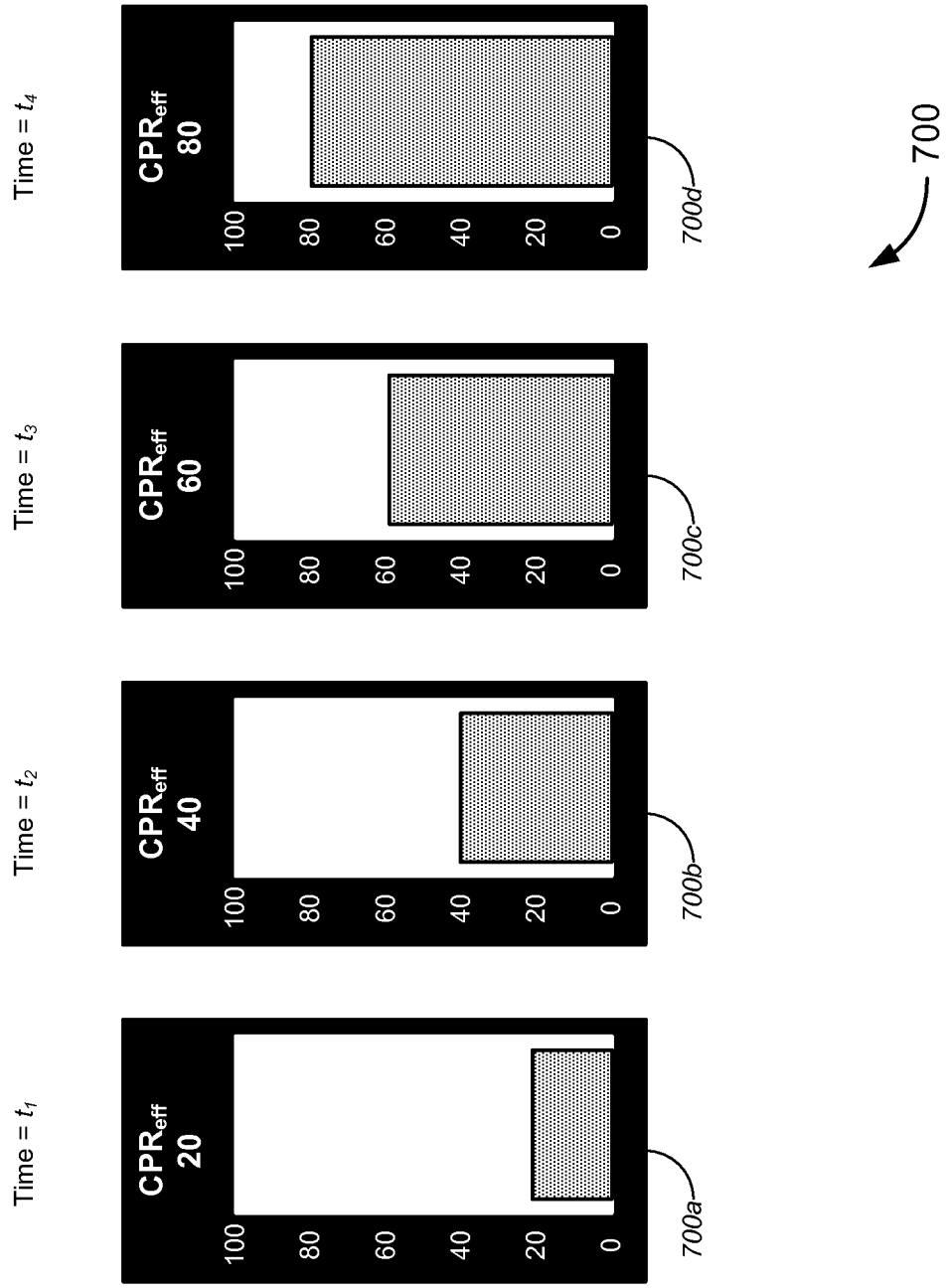
Figure 8:
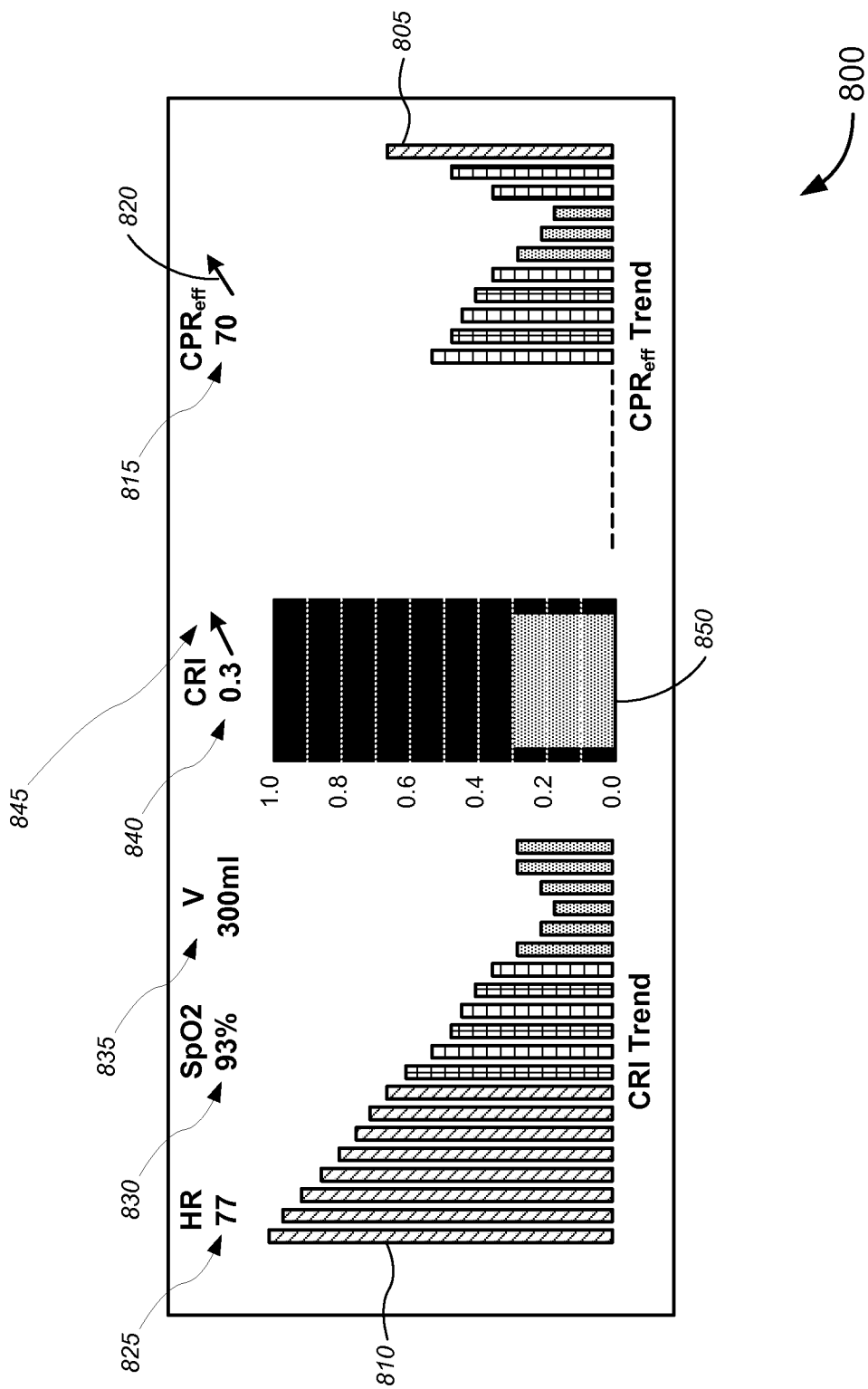
Figure 9A:
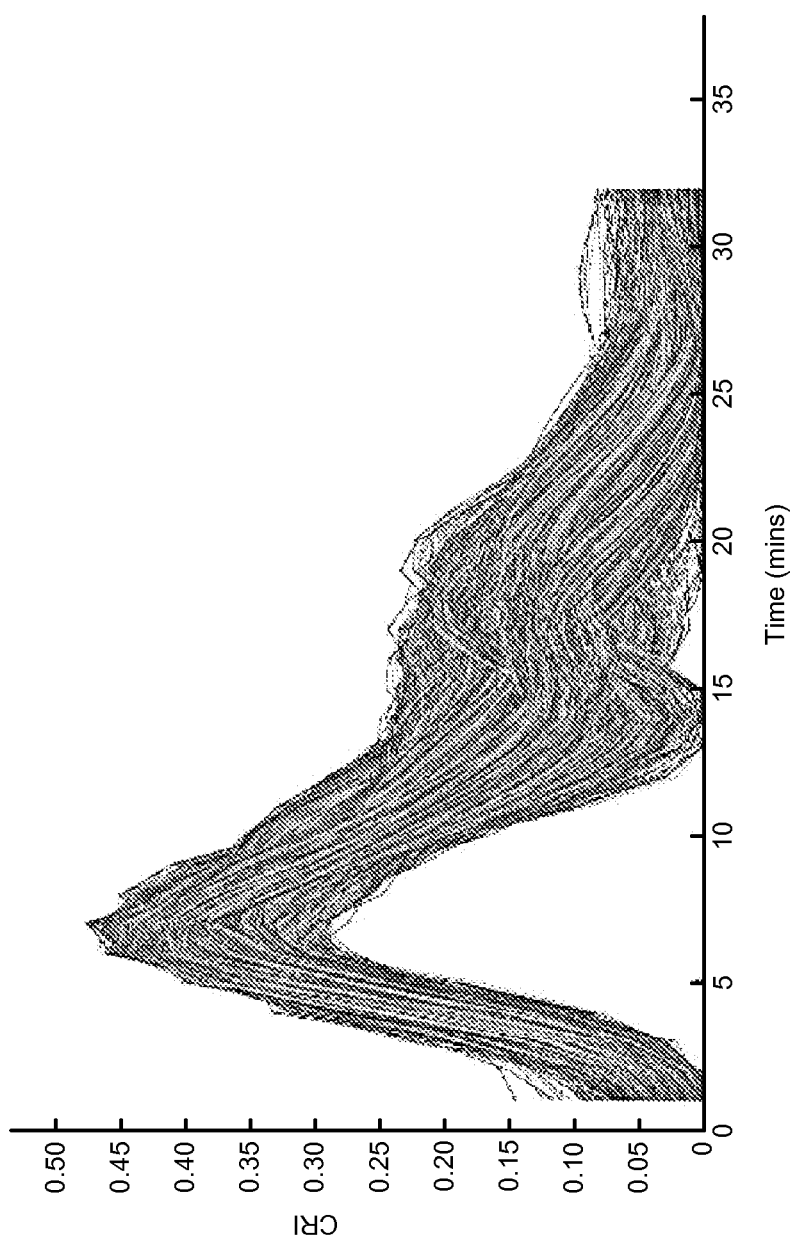
FIGS. 9A-9F are graphical diagrams illustrating an example set of clusters of arterial waveforms, each cluster of arterial waveform representing one waveform type, in accordance with various embodiments.
Figure 9B:
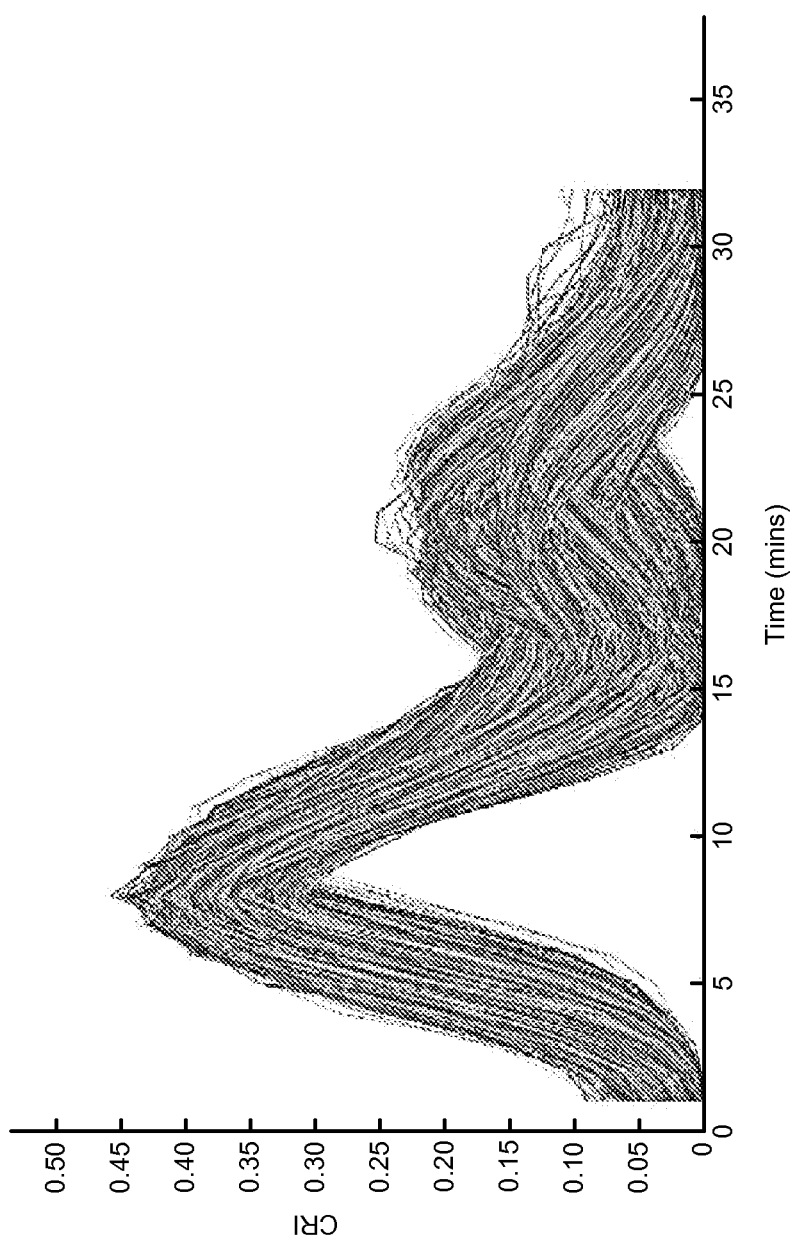
Figure 9C:
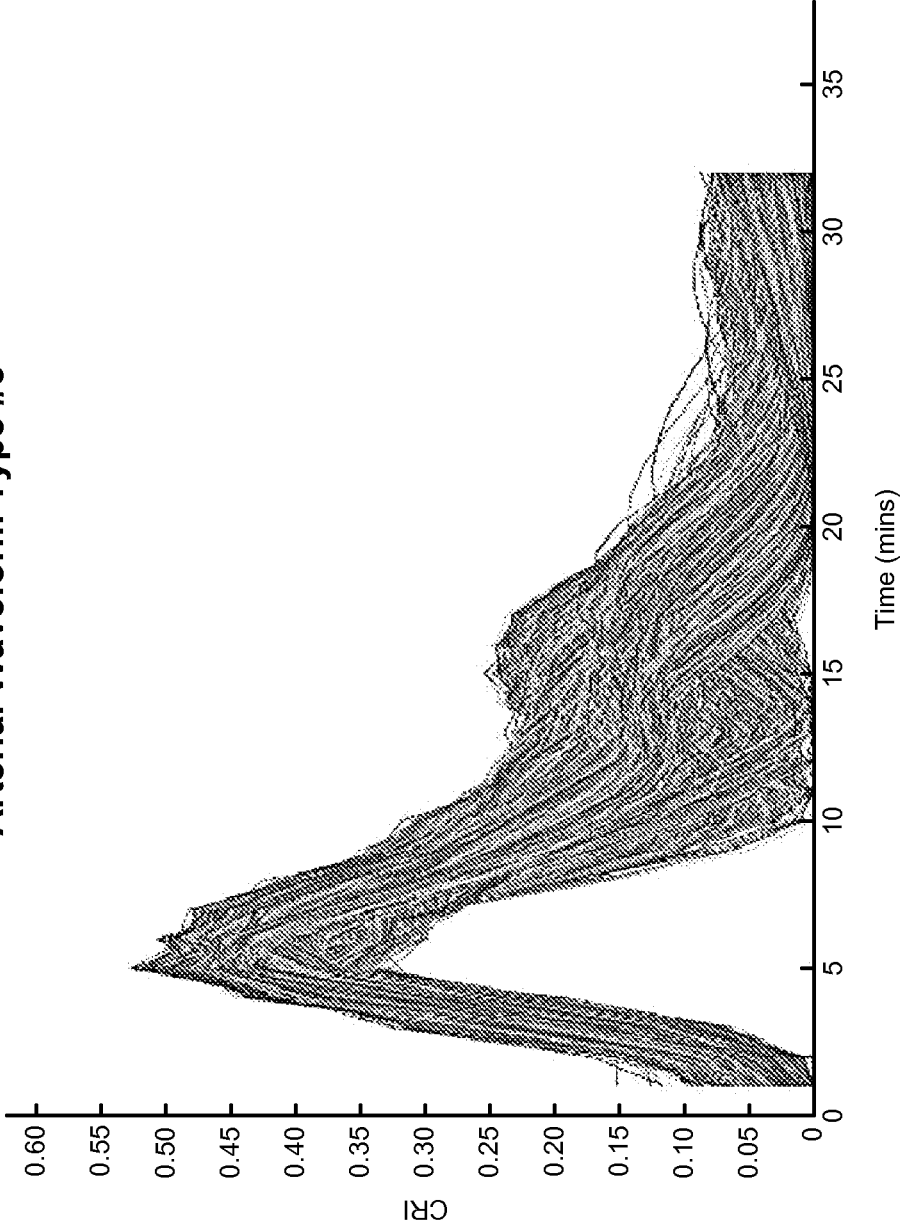
Figure 9D:
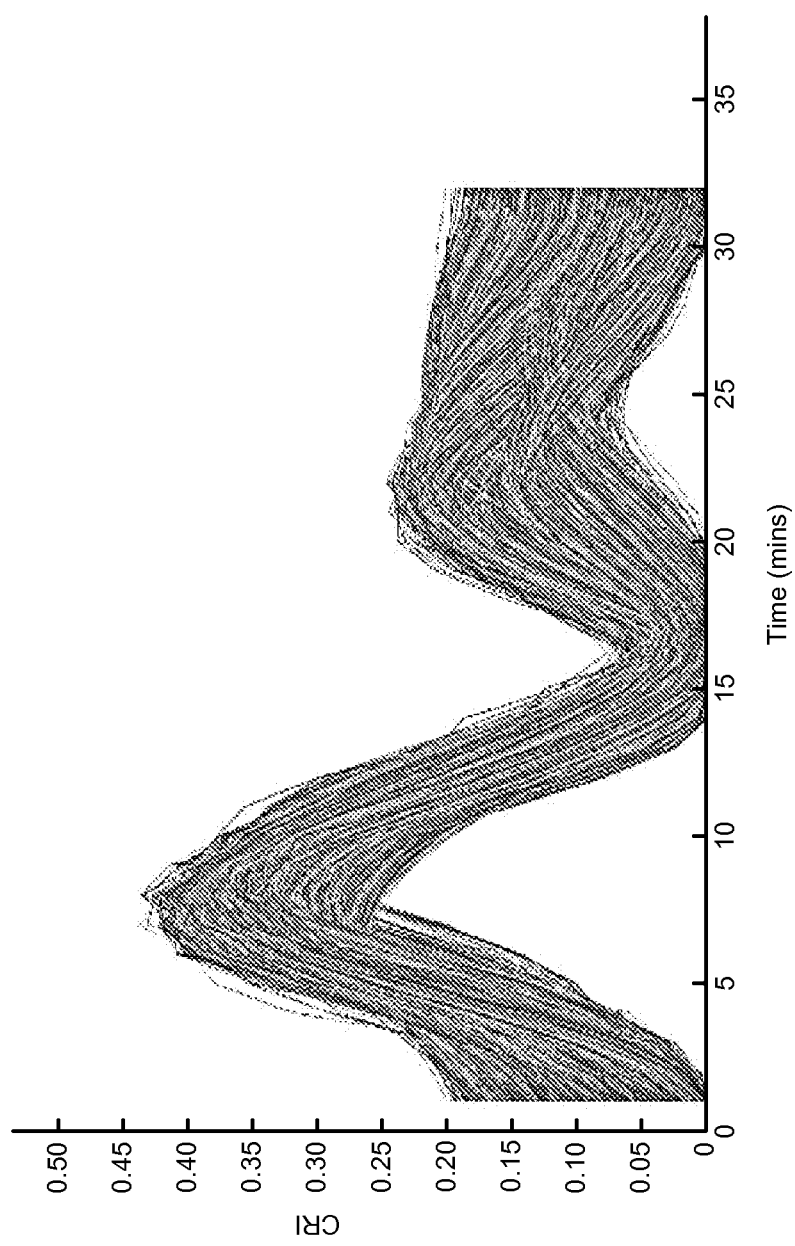
Figure 9E:
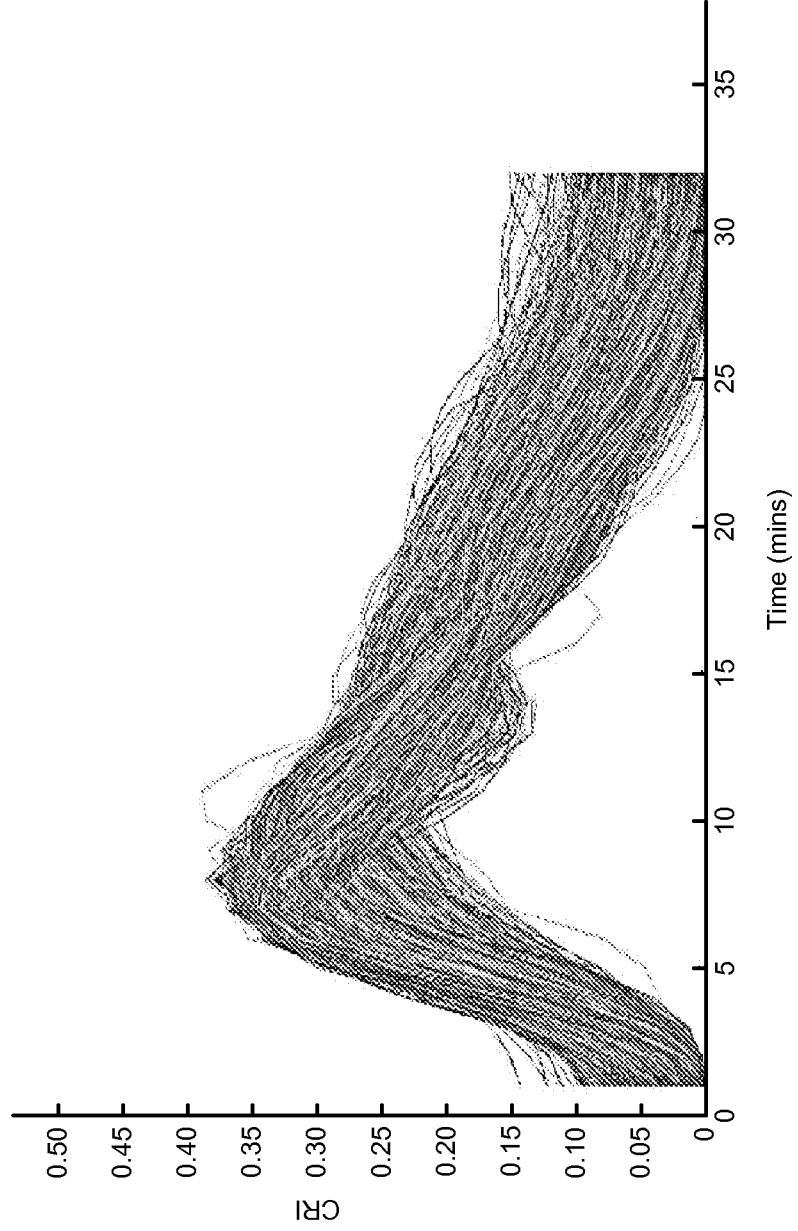
Figure 9F:
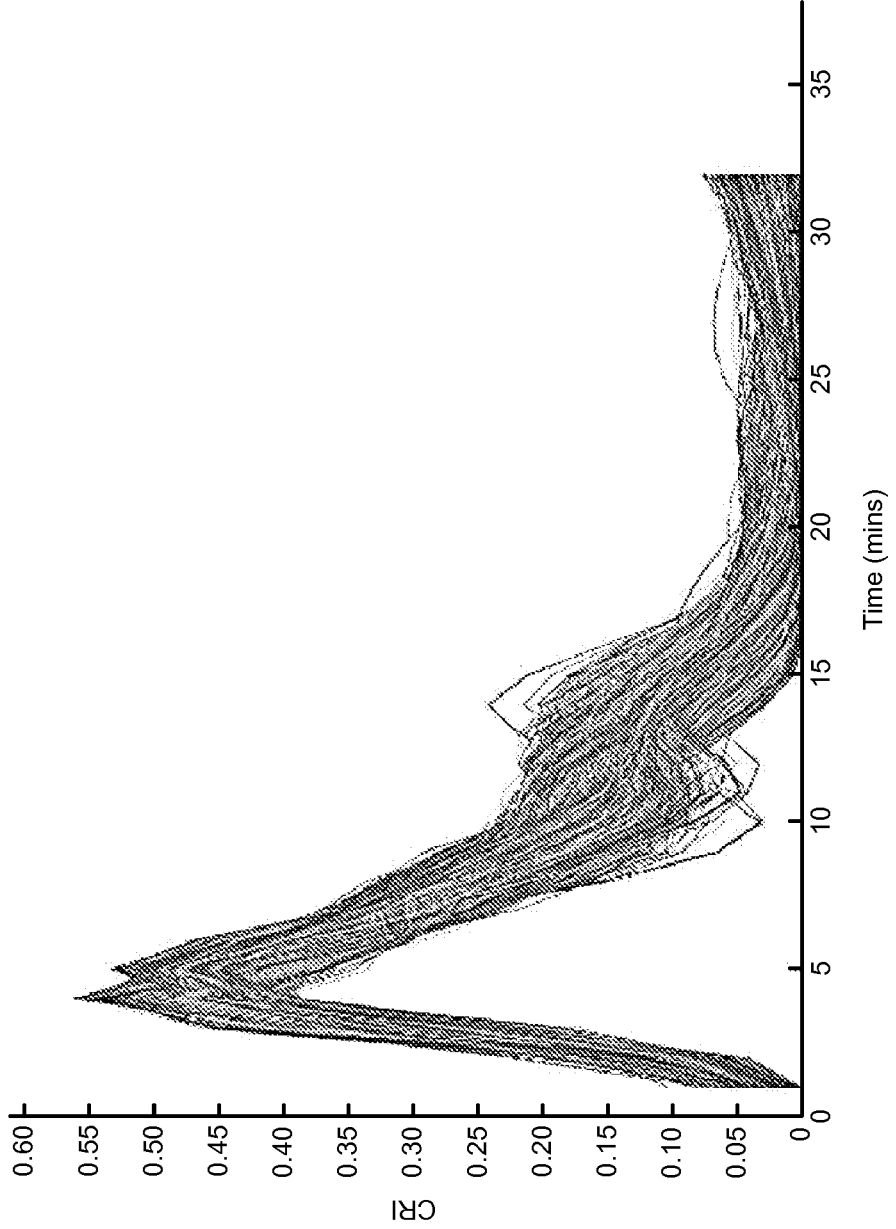

FIG. 7A illustrates four screen captures 700 of a display of a compensatory reserve monitor implementation that displays $CPR_{eff}$ as a "fuel gauge" type bar graph for a person undergoing central volume blood loss and subsequent hydration efforts, or for a person who is undergoing cardiac arrest and is about to, is undergoing, or has undergone CPR efforts. While FIG. 6 illustrates a trace of CRI over time, the bar graphs of FIG. 7A provide snapshots of CRI at the time of each screen capture corresponding to the CRI of FIG. 6. (In the illustrated implementation, the bar graphs are continuously and/or periodically updated, such that each bar graph could correspond to a particular position on the X-axis of FIG. 6.)

Figure 7B:
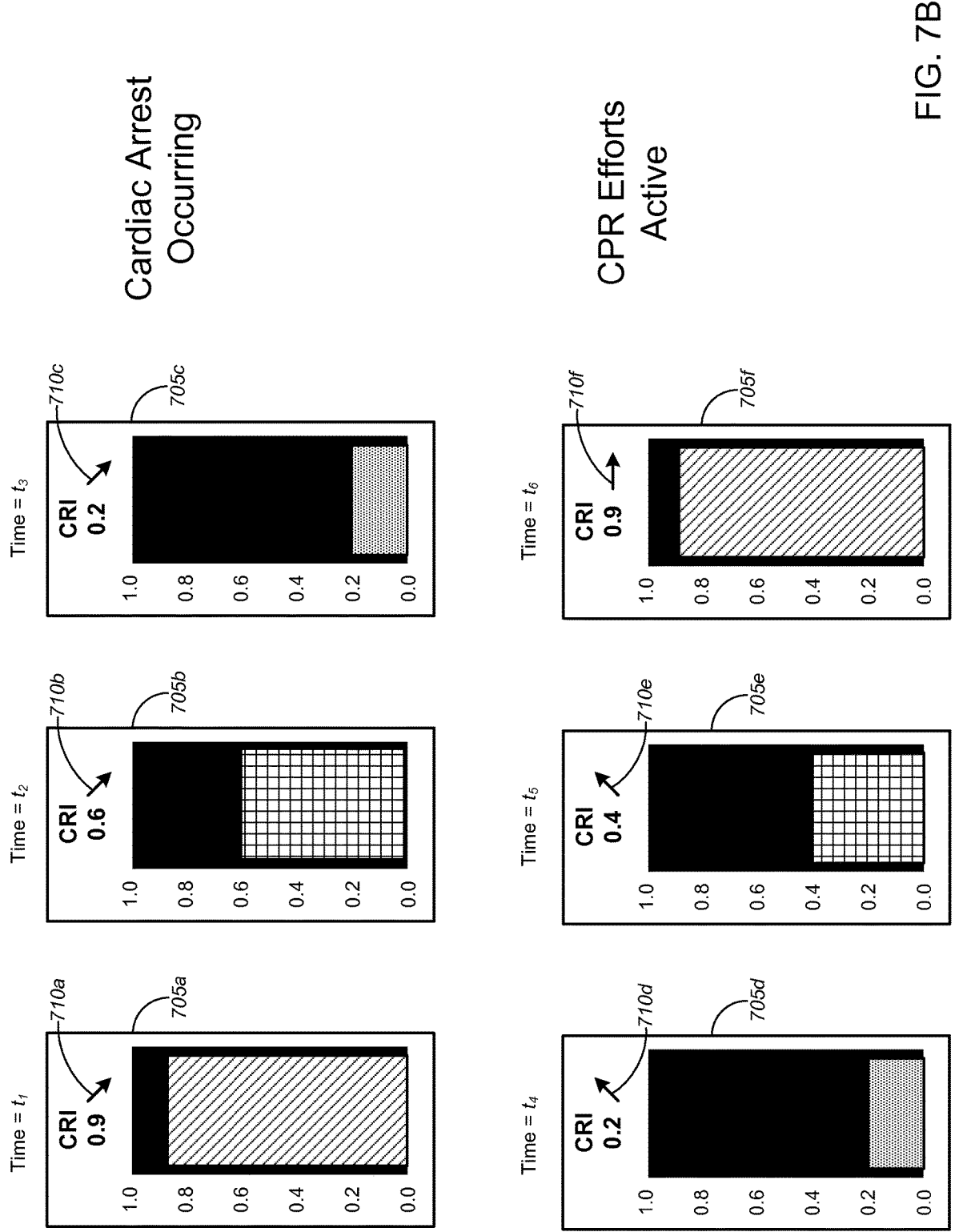

A variety of additional features are possible. Merely by way of example FIG. 7B illustrates similar "fuel gauge" type displays, but the displays feature bars of different colors—for example, green (illustrated by diagonal cross-hatching), yellow (illustrated by a checked pattern) and red illustrated by gray shading) corresponding to different levels of CRI, along with arrows 710 indicating trending in the CRI values (e.g., rising, declining, or remaining stable), the CRI values and trends being indicative of cardiac arrest occurring and/or CPR efforts being active.

In some embodiments, such a "fuel gauge" display (or other indicator of $CPR_{eff}$ or CRI and/or different physiological parameters) can be incorporated in a more comprehensive user interface. Merely by way of example, FIG. 8 illustrates an exemplary display 800 of a monitoring system. The display 800 includes a historical display 805 of recent $CPR_{eff}$ values, along with a historical display 810 of recent CRI estimates; in this example, each bar on each of, or one of, the historical displays 805 and 810 might correspond to an estimate performed every minute, but different estimate frequencies are possible, and in some embodiments, the operator can be given the option to specify a different frequency. As shown in FIG. 8, the zero value $CPR_{eff}$ bars of the historical display 810 indicate that CPR has not yet been administered, while the subsequent $CPR_{eff}$ values indicate that CPR efforts initially decline, but eventually become more effective, which is also reflected in the eventual upward trend of the CRI values. In the illustrated embodiment, the display 800 also includes numerical display 815 of the current $CPR_{eff}$ values as well as a trend indicator 820 (similar to that indicated above).

In particular embodiments, the display 800 can include additional information (and, in some cases, the types of information displayed and/or the type of display can be configured by the operator). For instance, the exemplary display 800 includes an indicator 825 of the patient's current heart rate and an indicator 830 of the patient's blood oxygen saturation level (SpO2). The exemplary display 800 also includes an indicator of the estimated volume, V, necessary for effective hydration, as well as an numerical indicator 840, a trend indicator 845, and a similar color coded "fuel gauge" display 850 of the current CRI. Other monitored parameters might be displayed as well, such as an ECG tracing, blood pressure, probability of bleeding estimates, and/or the like.

FIGS. 9A-9F (collectively, "FIG. 9") are graphical diagrams illustrating an example set of clusters of arterial waveforms, each cluster of arterial waveform representing one waveform type 900, in accordance with various embodiments.

Healthy arterial waveforms obtained from invasive and/or non-invasive blood pressure sensors, of any sensors—including, but not limited to, PPG sensors—that reflect the flow of blood by the heart, have specific shapes. These can be clustered based on shapes of a single heartbeat, either by hand or via automated and/or semi-automated clustering techniques, into specific groups. One example set of clusters is represented by FIGS. 9A-9F, each cluster representing one waveform type.

Using techniques for measuring the similarity between or among complex shapes, including, but not limited to, those defined in "Semi-supervised learning of a markovian," *SIAM Conference on Data Mining* (2008) by Bijral et al. ("Bijral 2008"), "Mixture of watson distributions: A generative model for hyperspherical embeddings," *AI and Statistics* (2007) by Bijral et al. ("Bijral 2007"), "Clustering through ranking on manifolds," *International Conference on Machine Learning (ICML)* (2005) by Breitenbach et al. ("Breitenbach 2005"), "Topological mapping with multiple visual manifolds," *Robotics: Science and Systems Conference* (2005) by Grudic et al. ("Grudic 2005"), "Outdoor path labeling using polynomial mahalanobis distance," *Robotics: Science and Systems Conference* (2006) by Grudic et al. ("Grudic 2006"), and "Topological mapping from image sequences," *IEEE Workshop on Learning in Computer Vision and Pattern Recognition (with CVPRO5)* (2005) by Mulligan et al. ("Mulligan 2005") (the disclosure of each of which is hereby incorporated by reference in their entirety for all purposes), one can calculate the distance from any waveform to clusters of waveforms.

With w(t) as a sample of a waveform of a single heartbeat at time t, a set of waveform values at times $\{t_1, t_2, \ldots, t_K\}$ may be defined by $$W=\{w(t_1), w(t_2), \ldots, w(t_K)\}. \quad \text{(Eq. 47)}$$

With $C_i$ as cluster i of representative healthy heartbeats, where the total number of clusters is I, where I is either experimentally determined, user specified, or autonomously/semi-autonomously determined using techniques from machine learning and statistics (one possible example is defined in Grudic 2005), thus $I \in \{1, 2, \ldots, I\}$. Thereafter, a distance between w(t) and $C_i$ may be defined, using techniques including, but not limited to, the techniques described in Bijral 2008, Bijral 2007, Breitenbach 2005, Grudic 2005, Grudic 2006, and Mulligan 2006, which may be represented by:

$$D(w(t), C_i) = \text{distance between } w(t) \text{ and } C_i. \quad \text{(Eq. 48)}$$

The minimum distance may be defined to be:

$$D_{min} = \min\{D(w(t), C_i), \ldots, D(w(t), C_1)\}. \quad \text{(Eq. 49)}$$

The maximum distance may be defined to be:

$$D_{max} = \max\{D(w(t), C_i), \ldots, D(w(t), C_1)\}. \quad \text{(Eq. 50)}$$

The total distance may be defined to be:

$$D_{total} = \Sigma_{i=1}^{I} D(w(t), C_i). \quad \text{(Eq. 51)}$$

The minimum distance to a set of waveforms may be defined as:

$$D_{min}^{W} = \Sigma_{k=1}^{K} \min\{D(t_k), C_i), \ldots, D(w(t_k), C_1)\}. \quad \text{(Eq. 52)}$$

The maximum distance to a set of waveforms may be defined as:

$$D_{max}^{W} = \Sigma_{k=1}^{K} \max\{D(w(t_k), C_i), \ldots, D(w(t_k), C_1)\}. \quad \text{(Eq. 53)}$$

The total distance to a set of waveforms may be defined as:

$$D_{total}^{W} = \Sigma_{k=1}^{K} \Sigma_{i=1}^{I} D(w(t_k), C_i). \quad \text{(Eq. 54)}$$

Measuring CPR Effectiveness Using Wave Shape

The effectiveness of CPR can be defined, after each heartbeat, using, but not limited to, one or more of the following measures: (1) $D_{min}$: Smaller values of this measure represent more effective CPR; (2) $D_{max}$: Smaller values of this measure represent more effective CPR; (3) $D_{total}$: Smaller values of this measure represent more effective CPR; (4) Some function, linear or nonlinear, of $D_{min}$, $D_{max}$, and/or $D_{total}$, denoted by $f(D_{min}, D_{max}, D_{total})$, which can either be a measure of a probability of effective CPR, or a number between, for example, 0 and 100, where a higher number indicates more effective CPR; and (5) Some function, linear or nonlinear, of all or some of the elements in $\{D(w(t), C_i), \ldots, D(w(t), C_1)\}$, denoted by $f(D(w(t), C_i), \ldots, D(w(t), C_1))$, which can either be a measure of a probability of effective CPR, or a number between, for example, 0 and 100, where a higher number indicates more effective CPR.

The effectiveness of CPR over a set of heartbeats $W=\{w(t_1), w(t_2), \ldots, w(t_K)\}$ can be defined, using, but not limited to, one or more of the following measures: (1) $D_{min}^{W}$: Smaller values of this measure represent more effective CPR; (2) $D_{max}^{W}$: Smaller values of this measure represent more effective CPR; (3) $D_{total}^{W}$: Smaller values of this measure represent more effective CPR; (4) Some function, linear or nonlinear, of $D_{min}^{W}$, $D_{max}^{W}$, and/or $D_{total}^{W}$, denoted by $f(D_{min}^{W}, D_{max}^{W}, D_{total}^{W})$, which can either be a measure of a probability of effective CPR, or a number between, for example, 0 and 100, where a higher number indicates more effective CPR; and (5) Some function, linear or nonlinear, of all or some of the elements in $\{\{D(w(t_1), C_i), \ldots, D(w(t_1), C_1)\}, \ldots, \{D(w(t_k), C_i), \ldots, D(w(t_k), C_1)\}\}$, denoted by $f(\{D(w(t_1), C_i), \ldots, D(w(t_1), C_1)\}, \ldots, \{D(w(t_k), C_1), \ldots, D(w(t_k), C_1)\})$, which can either be a measure of a probability of effective CPR, or a number between, for example, 0 and 100, where a higher number indicates more effective CPR.

Exemplary System and Hardware Implementation

FIG. 10 is a block diagram illustrating an exemplary computer or system hardware architecture, in accordance with various embodiments. FIG. 10 provides a schematic illustration of one embodiment of a computer system 1000 that can perform the methods provided by various other embodiments, as described herein, and/or can function as a monitoring computer, a CRI monitor, a processing unit of a sensor device, and/or the like, as described above. It should be noted that FIG. 10 is meant only to provide a generalized illustration of various components, of which one or more (or none) of each may be utilized as appropriate. FIG. 10, therefore, broadly illustrates how individual system elements may be implemented in a relatively separated or relatively more integrated manner.

The computer or hardware system 1000 is shown comprising hardware elements that can be electrically coupled via a bus 1005 (or may otherwise be in communication, as appropriate). The hardware elements may include one or more processors 1010, including, without limitation, one or more general-purpose processors and/or one or more special-purpose processors (such as digital signal processing chips, graphics acceleration processors, and/or the like); one or more input devices 1015, which can include, without limitation, a mouse, a keyboard and/or the like; and one or more output devices 1020, which can include, without limitation, a display device, a printer, and/or the like.

The computer or hardware system 1000 may further include (and/or be in communication with) one or more storage devices 1025, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 1000 might also include a communications subsystem 1030, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 1030 may permit data to be exchanged with a network (such as the network described below, to name one example), with other computer or hardware systems, and/or with any other devices described herein. In many embodiments, the computer or hardware system 1000 will further comprise a working memory 1035, which can include a RAM or ROM device, as described above.

The computer or hardware system 1000 also may comprise software elements, shown as being currently located within the working memory 1035, including an operating system 1040, device drivers, executable libraries, and/or other code, such as one or more application programs 1045, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 1025 described above. In some cases, the storage medium might be incorporated within a computer system, such as the system 1000. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 1000 and/or might take the form of source and/or installable code, which, upon compilation and/or installation on the computer or hardware system 1000 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 1000) to perform methods in accordance with various embodiments of the invention. According to a set of embodiments, some or all of the procedures of such methods are performed by the computer or hardware system 1000 in response to processor 1010 executing one or more sequences of one or more instructions (which might be incorporated into the operating system 1040 and/or other code, such as an application program 1045) contained in the working memory 1035. Such instructions may be read into the working memory 1035 from another computer readable medium, such as one or more of the storage device(s) 1025. Merely by way of example, execution of the sequences of instructions contained in the working memory 1035 might cause the processor(s) 1010 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 1000, various computer readable media might be involved in providing instructions/code to processor(s) 1010 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 1025. Volatile media includes, without limitation, dynamic memory, such as the working memory 1035. In some alternative embodiments, a computer readable medium may take the form of transmission media, which includes, without limitation, coaxial cables, copper wire and fiber optics, including the wires that comprise the bus 1005, as well as the various components of the communication subsystem 1030 (and/or the media by which the communications subsystem 1030 provides communication with other devices). In an alternative set of embodiments, transmission media can also take the form of waves (including, without limitation, radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 1010 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 1000. These signals, which might be in the form of electromagnetic signals, acoustic signals, optical signals, and/or the like, are all examples of carrier waves on which instructions can be encoded, in accordance with various embodiments of the invention.

The communications subsystem 1030 (and/or components thereof) generally will receive the signals, and the bus 1005 then might carry the signals (and/or the data, instructions, etc. carried by the signals) to the working memory 1035, from which the processor(s) 1005 retrieves and executes the instructions. The instructions received by the working memory 1035 may optionally be stored on a storage device 1025 either before or after execution by the processor(s) 1010.

CONCLUSION

This document discloses novel tools and techniques for assessing effectiveness of CPR in patients undergoing cardiac arrest (e.g., before, during, and/or after resuscitation), compensatory reserve, and similar physiological states. While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method for non-invasively determining the effectiveness of cardiopulmonary resuscitation (CPR) on a patient, comprising:
   retrieving, by one or more computer systems, physiological data of the patient from one or more sensors monitoring the patient during CPR, wherein the physiological data is waveform data;
   transforming, by one or more computer systems, the physiological data from waveform data to one or more patient compensatory serve index ("CRI") values thereby transforming the waveform data to a numerical value, wherein transforming the physiological data to the one or more patient CRI values includes:
   accessing a data store and acquiring a plurality of reference waveforms from a model, wherein each waveform of the plurality of reference waveforms corresponds to a respective CRI value determined from a ratio of intravascular volume loss at time t and intravascular volume loss at hemodynamic decompensation;
   comparing the patient waveform data against the plurality of reference waveforms of the model;
   determining a similarity between patient waveform data and the plurality of reference waveforms of the model individually; and
   determining the one or more patient CRI values that corresponds to the patient waveform data based at least in part on respective similarities of the patient waveform data to each of the plurality of reference waveforms of the model;
   based at least in part on the one or more patient CRI values, estimating, by one or more computer systems, an effectiveness of CPR on the patient, wherein the one or more patient CRI values are compared against a CRI model configured to relate changes in CRI values to the effectiveness of CPR on the patient; and
   displaying, by one or more computer systems, the effectiveness of CPR on the patient on a user interface.

2. The method of claim 1, wherein the one or more patient CRI values are estimated based on physiological data that are at least one of received before, received during, or received after CPR.

3. The method of claim 1, wherein the one or more patient CRI values comprise a plurality of patient CRI values, and wherein estimating effectiveness of a CPR procedure on the patient further is based at least in part on an average value of CRI over a time period or a standard deviation of at least some of the plurality of patient CRI values, a skewness of at least some of the plurality of patient CRI values, a rate of change of at least two of the plurality of patient CRI values, or a difference between two of the plurality of values of CRI.

4. The method of claim 1, wherein the effectiveness of CPR on the patient is displayed as a number on a scale from 0 to 100.

5. The method of claim 1, wherein the plurality of reference waveforms of the model correspond to a state of hemodynamic decompensation or near hemodynamic decompensation, or a series of states progressing towards hemodynamic decompensation.

6. The method of claim 1, wherein determining the similarity further comprises:
producing, for each respective patient waveform of the patient waveform data, a respective similarity coefficient representing a similarity between a respective patient waveform and each of the plurality of reference waveforms of the model;
normalizing the produced, respective similarity coefficients;
summing each respective value of CRI, corresponding to each of the plurality of reference waveforms of the model, respectively weighted by the normalized respective similarity coefficient; and
determining an estimated CRI value for the patient based on the summed, weighted CRI values.

7. The method of claim 1, wherein at least one of the one or more sensors is selected from the group consisting of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, and an electronic stethoscope.

8. The method of claim 1, wherein the physiological data comprises data representing blood pressure waveforms, plethysmograph waveforms, or photoplethysmograph (PPG) waveforms.

9. The method of claim 1, wherein the plurality of reference waveforms are generated by inducing a test subject to enter one or more physiological states, and obtaining physiological data from the test subject while the test subject is in a respective physiological state of the one or more physiological states.

10. The method of claim 9, further comprising:
inducing a physiological state of reduced circulatory system volume in the test subject.

11. The method of claim 10, wherein inducing the physiological state comprises subjecting the test subject to lower body negative pressure ("LBNP").

12. The method of claim 11, wherein inducing the physiological state comprises subjecting the test subject to dehydration.

13. The method of claim 9, wherein the one or more physiological states comprises a state of cardiovascular collapse or near-cardiovascular collapse.

14. The method of claim 9, wherein the one or more physiological states comprises a state of euvolemia.

15. The method of claim 9, wherein the one or more physiological states comprises a state of hypervolemia.

16. The method of claim 9, wherein the one or more physiological states comprises a state of dehydration or hypovolemia.

17. The method of claim 9, further comprising correlating the physiological data of the test subject to the respective physiological state, wherein correlating the physiological data of the test subject with the respective physiological state of the test subject further comprises:
identifying a most predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter of the physiological data of the test subject, and wherein each of the one or more outcomes $o_k$ represents a physiological state measurement of the one or more physiological states respectively;
autonomously learning a set of probabilistic predictive models $\hat{o}_k = M_k(S_k)$, where $\hat{o}_k$ is a prediction of outcome $o_k$ derived from a model $M_k$ that uses as inputs values obtained from the set of signals $S_k$; and
repeating the operation of autonomously learning incrementally from data that contains examples of values of signals $s_1, s_2, \ldots, s_D$ and corresponding outcomes $o_1, o_2, \ldots, o_K$.

18. The method of claim 1, wherein the effectiveness of CPR on the patient is displayed as a qualitative indicator.

19. The method of claim 1, further including outputting instructions to control a therapeutic device.

20. A system for non-invasively assessing the health of a patient, comprising:
one or more sensors to obtain physiological data from the patient; and
a computer system in communication with the one or more sensors, the computer system comprising:
one or more processors; and
a non-transitory computer readable medium in communication with the one or more processors, the computer readable medium having encoded thereon a set of instructions executable by the one or more processors to cause the computer system to:
retrieve physiological data of the patient from one or more sensors monitoring the patient, wherein the physiological data is waveform data;
transform the physiological data from waveform data to one or more patient compensatory reserve index ("CRI") values thereby transforming the waveform data to a numerical value, wherein transforming the physiological data to the one or more patient CRI values includes:
accessing a data store and acquiring a plurality of reference waveforms from a model, wherein each waveform of the plurality of reference waveforms corresponds to a respective CRI value determined from a ratio of intravascular volume loss at time t and intravascular volume loss at hemodynamic decompensation;
comparing the patient waveform data against the plurality of reference waveforms of the model;
determining a similarity between patient waveform data and the plurality of reference waveforms of the model individually; and
determining the one or more patient CRI values that corresponds to the patient waveform data based at least in part on respective similarities of the patient waveform data to each of the plurality of reference waveforms of the model;
based at least in part on the one or more patient CRI values, estimate the health of the patient, wherein the one or more patient CRI values are compared against a CRI model configured to relate changes in CRI values to the health of the patient; and
display the health of the patient on a user interface.

21. The system of claim 20, wherein the one or more patient CRI values are estimated based on physiological data that are at least one of received before, received during, or received after CPR.

22. The system of claim 20, wherein the one or more patient CRI values comprise a plurality of patient CRI values, and wherein estimating effectiveness of a CPR procedure on the patient further is based at least in part on an average value of CRI over a time period or a standard deviation of at least some of the plurality of patient CRI values, a skewness of at least some of the plurality of patient CRI values, a rate of change of at least two of the plurality of patient CRI values, or a difference between two of the plurality of values of CRI.

23. The system of claim 20, further including displaying the effectiveness of CPR on the patient as a number on a scale from 0 to 100.

24. The system of claim 20, wherein the plurality of reference waveforms of the model correspond to a state of hemodynamic decompensation or near hemodynamic decompensation, or a series of states progressing towards hemodynamic decompensation.

25. The system of claim 20, wherein determining the similarity between patient waveform data and the plurality of reference waveforms of the model further comprises:
producing, for each respective patient waveform of the patient waveform data, a respective similarity coefficient representing the similarity between a respective patient waveform and each of the plurality of reference waveforms of the model;
normalizing the produced, respective similarity coefficients;
summing each respective value of CRI, corresponding to each of the plurality of reference waveforms of the model, respectively weighted by the normalized respective similarity coefficient; and
determining an estimated CRI value for the patient based on the summed, weighted CRI values.

26. The system of claim 20, wherein at least one of the one or more sensors is selected from the group comprising of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, and an electronic stethoscope.

27. The system of claim 20, wherein the physiological data comprises data representing blood pressure waveforms, plethysmograph waveforms, or photoplethysmograph (PPG) waveforms.

28. The method of claim 20, wherein the effectiveness of CPR on the patient is displayed as a qualitative indicator.

29. The method of claim 20, further including outputting instructions to control a therapeutic device.

30. A system for non-invasively determining the effectiveness of cardiopulmonary resuscitation (CPR) on a patient, comprising:
one or more sensors to obtain physiological data from the patient; and
a computer system in communication with the one or more sensors, the computer system comprising:
one or more processors; and
a non-transitory computer readable medium in communication with the one or more processors, the computer readable medium having encoded thereon a set of instructions executable by the one or more processors to cause the computer system to:
retrieve physiological data of the patient from one or more sensors monitoring the patient during CPR, wherein the physiological data is waveform data;
transform the physiological data from waveform data to one or more patient compensatory reserve index ("CRI") values thereby transforming the waveform data to a numerical value, wherein transforming the physiological data to the one or more patient CRI values includes:
accessing a data store and acquiring a plurality of reference waveforms from a model, wherein each waveform of the plurality of reference waveforms corresponds to a respective CRI value determined from a ratio of intravascular volume loss at time t and intravascular volume loss at hemodynamic decompensation;
comparing the patient waveform data against the plurality of reference waveforms of the model;
determining a similarity between patient waveform data and the plurality of reference waveforms of the model individually; and
determining the one or more patient CRI values that corresponds to the patient waveform data based at least in part on respective similarities of the patient waveform data to each of the plurality of reference waveforms of the model;
based at least in part on the one or more patient CRI values, estimate an effectiveness of CPR on the patient, wherein the one or more patient CRI values are compared against a CRI model configured to relate changes in CRI values to the effectiveness of CPR on the patient; and
display the effectiveness of CPR on the patient on a user interface.

31. The system of claim 30, wherein the one or more patient CRI values comprise a plurality of patient CRI values, and wherein estimating effectiveness of a CPR procedure on the patient further is based at least in part on an average value of CRI over a time period or a standard deviation of at least some of the plurality of patient CRI values, a skewness of at least some of the plurality of patient CRI values, a rate of change of at least two of the plurality of patient CRI values, or a difference between two of the plurality of values of CRI.

32. The system of claim 30, wherein determining the similarity between patient waveform data and the plurality of reference waveforms of the model further comprises:
producing, for each respective patient waveform of the patient waveform data, a respective similarity coefficient representing the similarity between a respective patient waveform and each of the plurality of reference waveforms of the model;
normalizing the produced, respective similarity coefficients;
summing each respective value of CRI, corresponding to each of the plurality of reference waveforms of the model, respectively weighted by the normalized respective similarity coefficient; and
determining an estimated CRI value for the patient based on the summed, weighted CRI values.

33. The system of claim 30, wherein at least one of the one or more sensors is selected from the group comprising of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, and an electronic stethoscope.

34. The system of claim 30, wherein the physiological data comprises data representing blood pressure waveforms, plethysmograph waveforms, or photoplethysmograph (PPG) waveforms.

35. The method of claim 1, further including outputting a recommended treatment option based on the one or more patient CRI values.

* * * * *